US012760348B2

(12) United States Patent
Wu et al.

(10) Patent No.: US 12,760,348 B2

(45) **Date of Patent: *Oct. 13, 2026**

(54) METHODS FOR ENZYMATIC PEPTIDE LIGATION

(71) Applicant: NANYANG TECHNOLOGICAL UNIVERSITY, Singapore (SG)

(72) Inventors: Bin Wu, Singapore (SG); Renliang Yang, Singapore (SG); Yee Hwa Wong, Singapore (SG); Julien Lescar, Singapore (SG); Chuan Fa Liu, Singapore (SG); James P Tam, Singapore (SG); Kien Truc Giang Nguyen, Singapore (SG); Ziqi Long, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 642 days.

This patent is subject to a terminal disclaimer.

(21) Appl. No.: 17/937,298

(22) Filed: Sep. 30, 2022

(65) Prior Publication Data

US 2023/0128192 A1 Apr. 27, 2023

Related U.S. Application Data

(63) Continuation of application No. 16/336,023, filed as application No. PCT/SG2017/050458 on Sep. 12, 2017, now Pat. No. 11,795,488.

(30) Foreign Application Priority Data

Sep. 23, 2016 (SG) ........................... 10201607951V

(51) Int. Cl.
*C12P 21/02* (2006.01)
*C07K 14/415* (2006.01)
*C12N 9/00* (2006.01)

(52) U.S. Cl.
CPC ............ *C12P 21/02* (2013.01); *C07K 14/415* (2013.01); *C12N 9/93* (2013.01)

(58) Field of Classification Search
CPC .......... C12P 21/02; C07K 14/415; C12N 9/93
See application file for complete search history.

(56) References Cited

U.S. PATENT DOCUMENTS 8,569,575 B2 * 10/2013 Molinero ............ C07K 14/415 800/278
2012/0244575 A1 * 9/2012 Poth .................... C07K 14/415 536/23.6

FOREIGN PATENT DOCUMENTS

WO 2015/163818 A1 10/2015
WO 2017/049362 A1 3/2017
WO 2017/054044 A1 4/2017

OTHER PUBLICATIONS

Conlan et al., Circular Micro-Proteins and Mechanisms of Cyclization, Current Pharmaceutical Design, 2011, vol. 17, p. 4318-4328 (Year: 2011).*
Uniprot Accession No. A0AON9JZ32, entry version 1, published Jan. 20, 2016, available from <https://rest.uniprot.org/unisave/A0AON9JZ32?format=txt&versions=1> (Year: 2016).*
Altschul et al., "Basic Local Alignment Search Tool," *Journal of Molecular Biology*, 215:403-410, 1990.
Altschul et al., "Gapped BLAST and PSI-BLAST: a new generation of protein database search programs," *Nucleic Acids Research*, 25(17):3389-3402, 1997.
Bernath-Levin et al., "Peptide Macrocyclization by a Bifunctional Endoprotease," *Chemistry & Biology*, 22:571-582, 2015. (13 pages).
Chen et al., "A general strategy for the evolution of bond-forming enzymes using yeast display," *PNAS*, 108(28): 11399-11404, 2011.
Chen et al., "Cloning, Isolation, and Characterization of Mammalian Legumain, an Asparaginyl Endopeptidase," *The Journal of Biological Chemistry*, 272(12):8090-8098, 1997. (10 pages).
Dall et al., "Mechanistic and structural studies on legumain explain its zymogenicity, distinct activation pathways, and regulation," *PNAS*, 110(27):10940-10945, 2013.
Dall et al., "Structure and function of legumain in health and disease," *Biochimie*, 122:126-150, 2016.
Dall et al., "Structure and Mechanism of an Aspartimide-Dependent Peptide Ligase in Human Legumain," *Angewandte Chemie International Edition*, 54:2917-2921, 2015.
Guimaraes et al., "Site-specific C-terminal and internal loop labeling of proteins using sortase-mediated reactions," *Nature Protocols*, 8(9):1787-1799, 2013.
Harris et al., "Efficient backbone cyclization of linear peptides by a recombinant asparaginyl endopeptidase," *Nature Communications*, 6(10199):1-10, 2015.
Ishii, "Legumain: Asparaginyl Endopeptidase," *Methods in Enzymology*, 244:604-615, 1994.
Nguyen et al., "Butelase 1 is an Asx-specific ligase enabling peptide macrocyclization and synthesis," *Nature Chemical Biology*, 10(9): 732-738, 2014. (42 pages).
Nguyen et al., "Butelase 1: A Versatile Ligase for Peptide and Protein Macrocyclization," *Journal of the American Chemical Society*, 137:15398-15401, 2015.
Nguyen et al., "Site-Specific N-Terminal Labeling of Peptides and Proteins using Butelase 1 and Thiodepsipeptide," *Angewandte Chemie International Edition*, 54:15694-15698, 2015.

(Continued)

*Primary Examiner* — David Steadman
*Assistant Examiner* — Scott E. Mulder
(74) *Attorney, Agent, or Firm* — Seed Intellectual Property Law Group LLP

(57) ABSTRACT

The present invention relates to a method of ligating a first peptide via its C-terminus to the N-terminus of a second peptide, wherein the reaction is catalyzed by an asparagine/aspartate (Asx) peptide ligase OaAEPI Cys247Ala having the amino acid sequence of SEQ ID NO: 1. Further encompassed are a method of preparing a dimer, oligomer, or multimer of one or more peptides of interest and a method of modifying or tagging the surface of a target cell by one or more peptides of interest. Also encompassed in the invention are the ligated peptides and/or tagged target cells obtainable according to any of the methods, the peptide ligase OaAEPI Cys247Ala having the amino acid sequence of SEQ ID NO: 1, as well as kits comprising said peptide ligase.

9 Claims, 52 Drawing Sheets

Specification includes a Sequence Listing.

(56) References Cited

OTHER PUBLICATIONS

Saska et al., "An Asparaginyl Endopeptidase Mediates in Vivo Protein Backbone Cyclization," *The Journal of Biological Chemistry*, 282(40):29721-29728, 2007. (9 pages).
Supplementary European Search Report corresponding to European Application No. EP 17853546.4, 7 pages, dated Mar. 23, 2020.
Swee et al., "Sortase-mediated modification of αDEC205 affords optimization of antigen presentation and immunization against a set of viral epitopes," *PNAS*, 110(4):1428-1433, 2013.
Theile et al., "Site-specific N-terminal labeling of proteins using sortase-mediated reactions," *Nature Protocols*, 8(9):1800-1807, 2013. (9 pages).
Wagner et al., "Bispecific antibody generated with sortase and click chemistry has broad antiinfluenza virus activity," *PNAS*, 111(47):16820-16825, 2014.
Witte et al., "Production of unnaturally linked chimeric proteins using a combination of sortase-catalyzed transpeptidation and click chemistry," *Nature Protocols*, 8(9):1808-1819, 2013.
Yang et al., "Engineering a Catalytically Efficient Recombinant Protein Ligase," *Journal of the American Chemical Society*, 139:5351-5358, 2017.
Zhao et al., "Structural analysis of asparaginyl endopeptidase reveals the activation mechanism and a reversible intermediate maturation stage," *Cell Research*, 24(3):344-358, 2014.

* cited by examiner

FIG. 2A
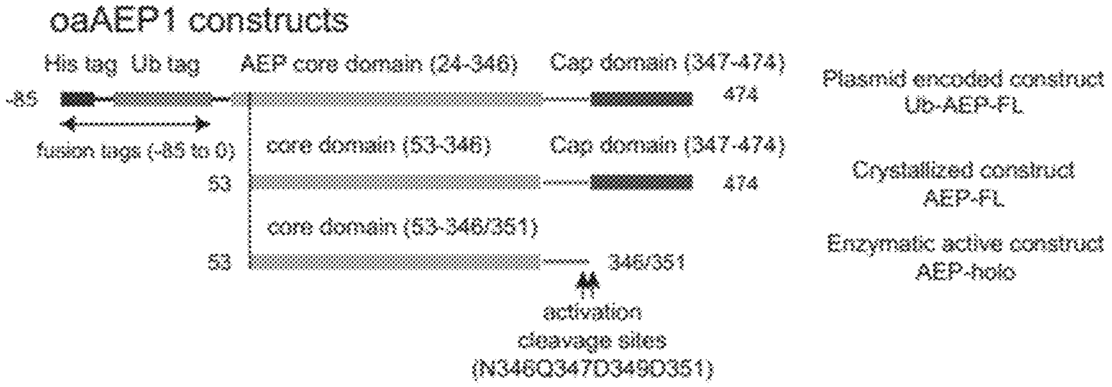
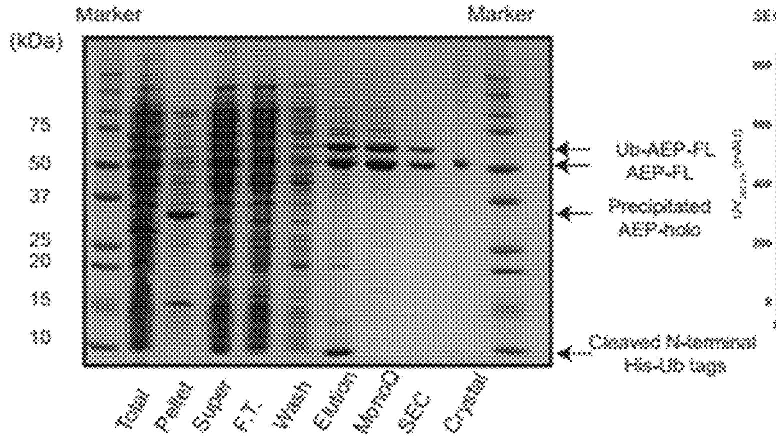
FIG. 2B
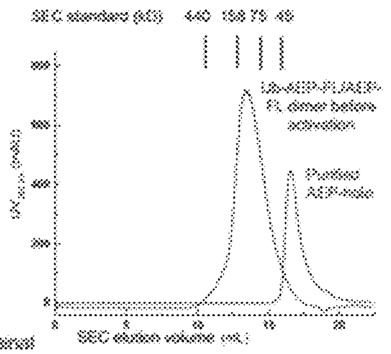
FIG. 2C
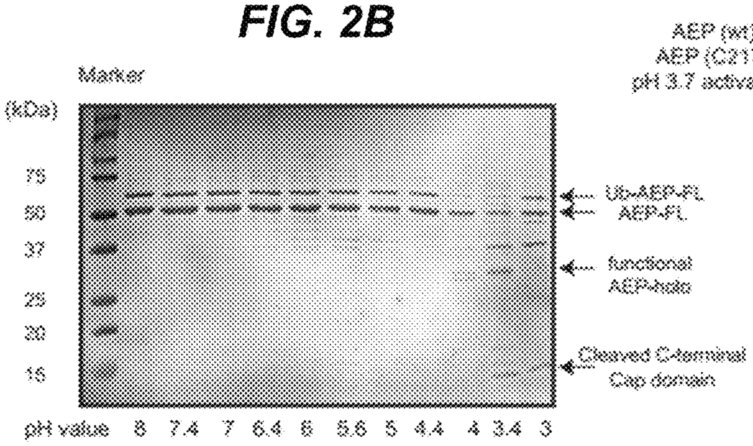
FIG. 2D
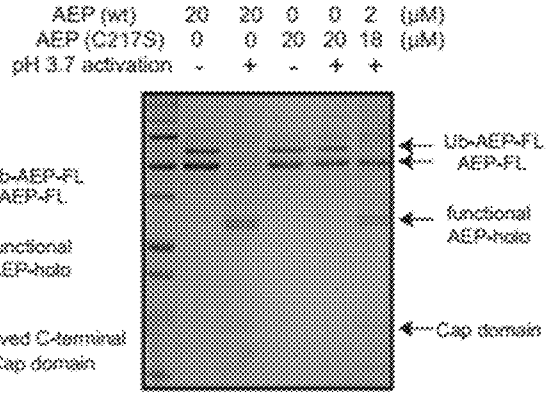
FIG. 2E FIG. 3A
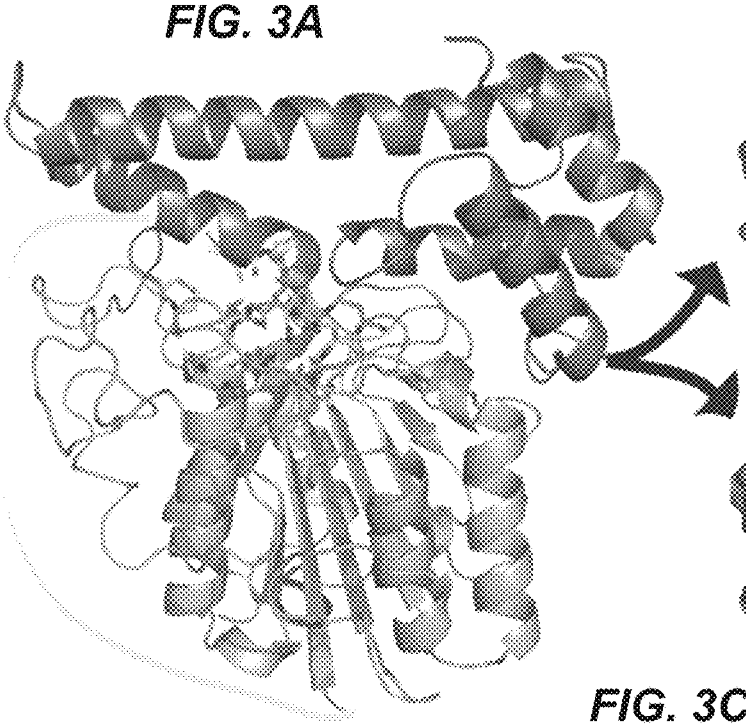
FIG. 3B
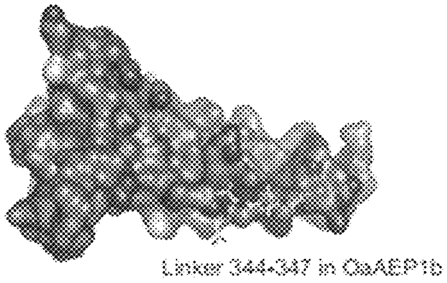
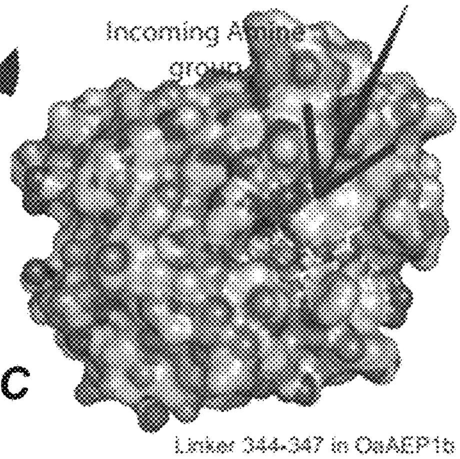
FIG. 3C
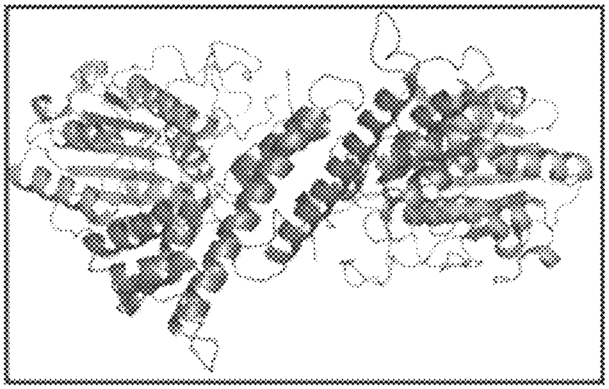
FIG. 3D
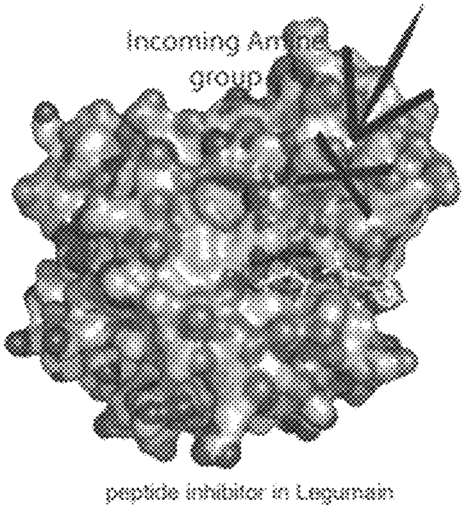
FIG. 3E

FIG. 5A
| Ligase | $k_{cat}(s^{-1})$ | $k_m(\mu M)$ | $k_{cat}/K_m(M^{-1}\ s^{-1})$ |
|---|---|---|---|
| WT AEP | 0.052 ± 0.008 | 245 ± 60 | 215 |
| AEP (Cys247Ala) | 13.9 ± 1.1 | 407 ± 49 | 34,209 |
| Butelase 1 | 4.83 ± 0.62 | 48.4 ± 14 | 99,793 |
FIG. 5B
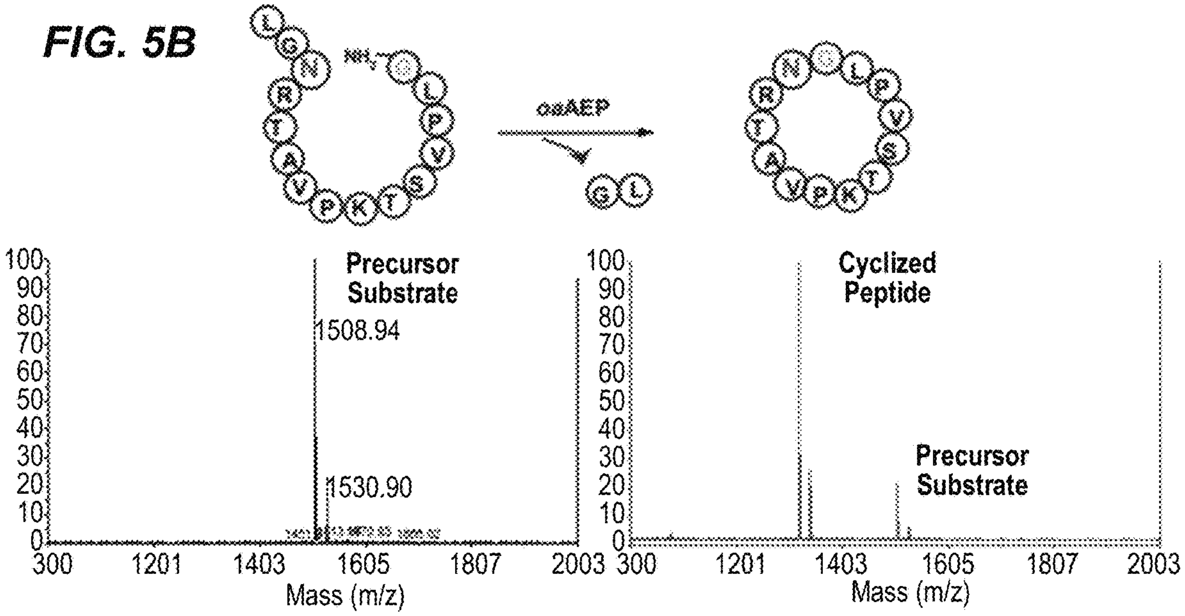
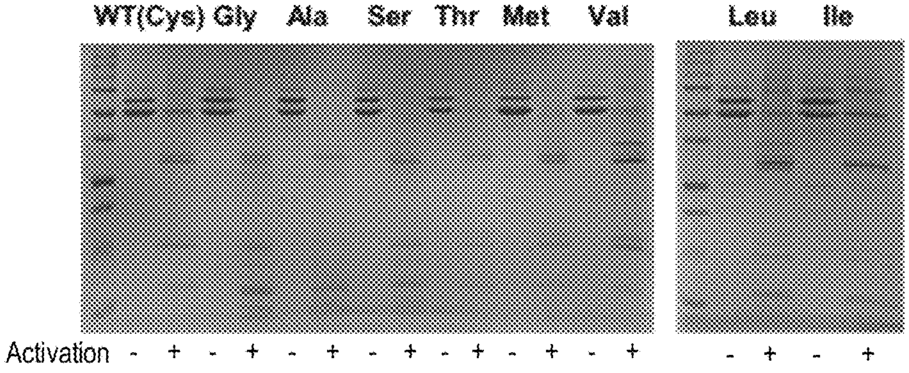
FIG. 5C
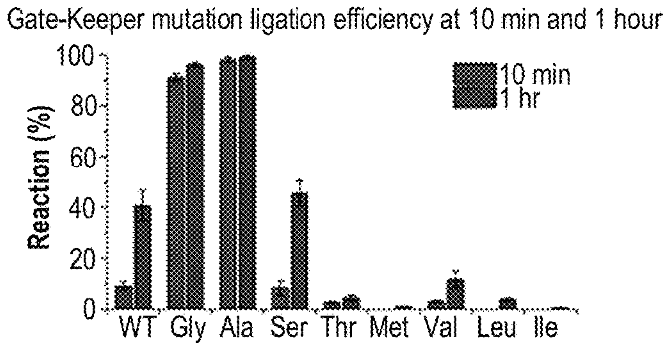
FIG. 5D

FIG. 7A

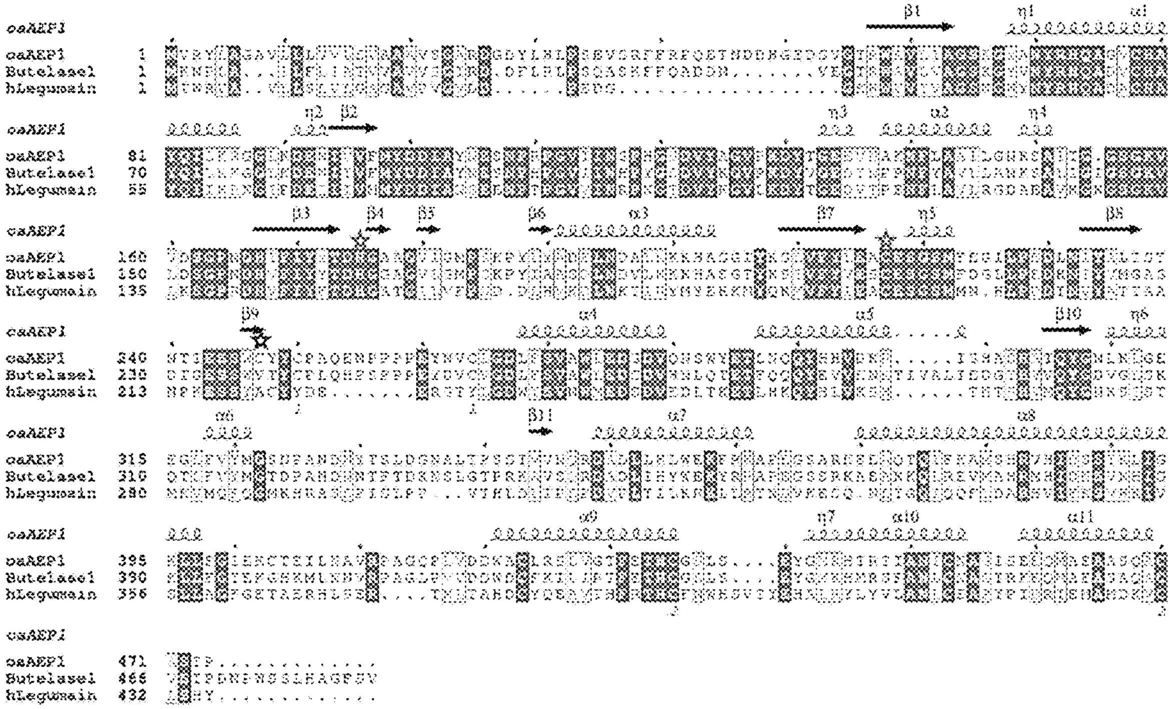

FIG. 7B

-85 MGMAHHHHHHMQIFVKTLTGKTITLEVEPSDTIENVKAKIQDKEGIPPDQQ
-36 RLIFAGKQLEDGRTLSDYNIQKESTLHLVLRLRGGARDGDYLHLPSEVSRF
40 FRPQETNDDHGEDSVGTRWAVLIAGSKGYANYRHQAGVCHAYQILKRGG
89 LKDENIVVFMYDDIAYNESNPRPGVIINSPHGSDVYAGVPKDYTGEEVNAK
140 NFLAAILGNKSAITGGSGKVVDSGPNDHIFIYYTDHGAAGVIGMPSKPYLY
191 ADELNDALKKKHASGTYKSLVFYLEACESGSMFEGILPEDLNIYALTSTNTT
243 ESSWCYYCPAQENPPPPEYNVCLGDLFSVAWLEDSDVQNSWYETLNQQY
292 HHVDKRISHASHATQYGNLKLGEEGLFVYMGSNPANDNYTSLDGNALTPS
342 SIVVNQRDADLLHLWEKFRKAPEGSARKEEAQTQIFKAMSHRVHIDSSIKL
393 IGKLLFGIEKCTEILNAVRPAGQPLVDDWACLRSLVGTFETHCGSLSEYGM
443 RHTRTIANICNAGISEEQMAEAASQACASIP

Expression Fusion tags (-85 to 0)

Core Domain (24 to 325)

Linker (326 to 347)

Cap Domain (348 to 474)

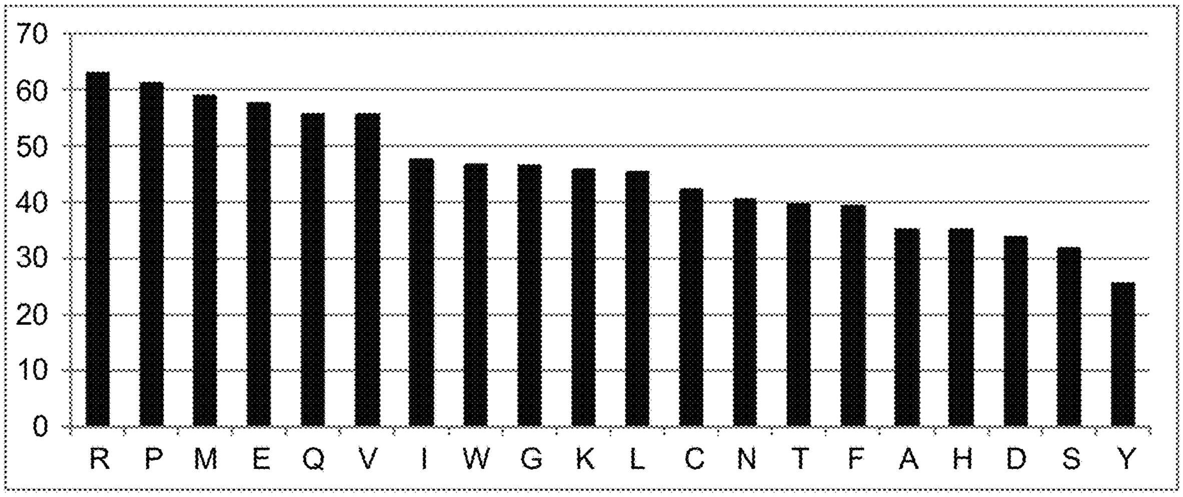
*FIG. 11C*
GLYRRGRLYRRNXL (J1-J20: NGL, NAL, NTL, NSL, NYL, NCL, NEL, NPL, NLL, NIL, NNL, NWL, NRL, NHL, NDL, NVL, NML, NKL, NQL, NFL, total 20 peptides)
Final – Shots 1000- LCFP3; Label J1
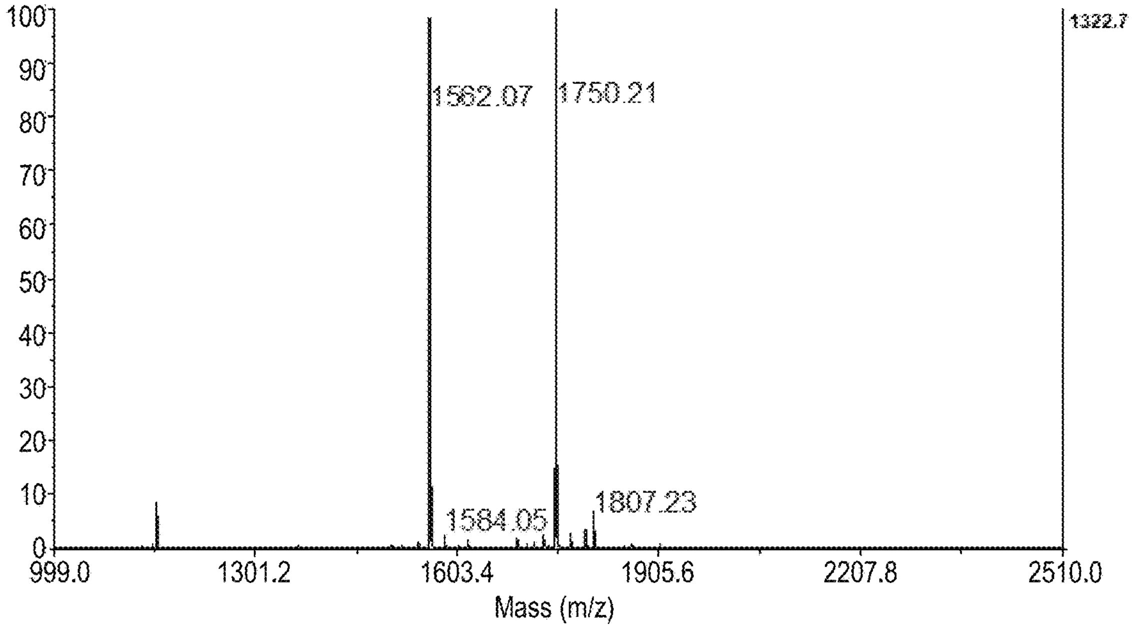
*FIG. 11D1*

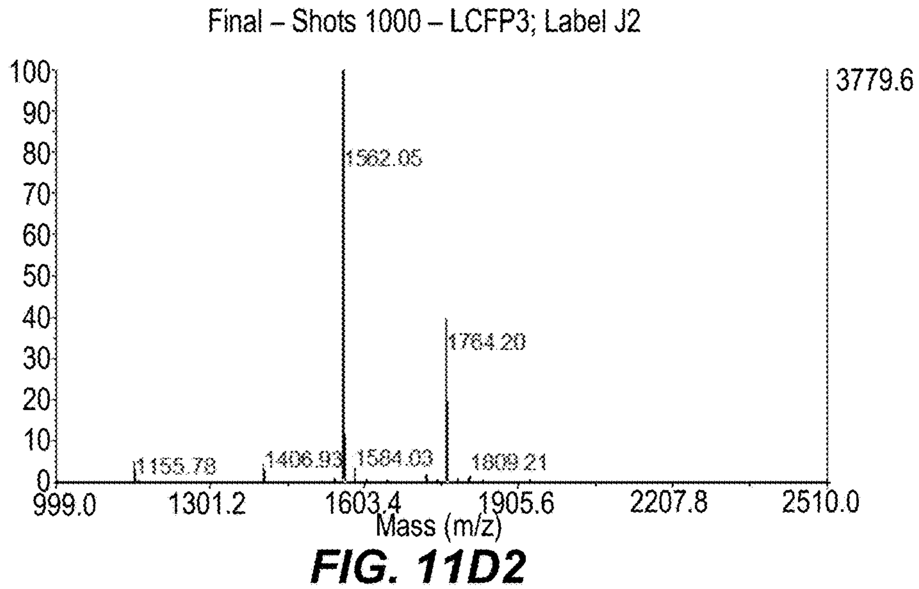
FIG. 11D2
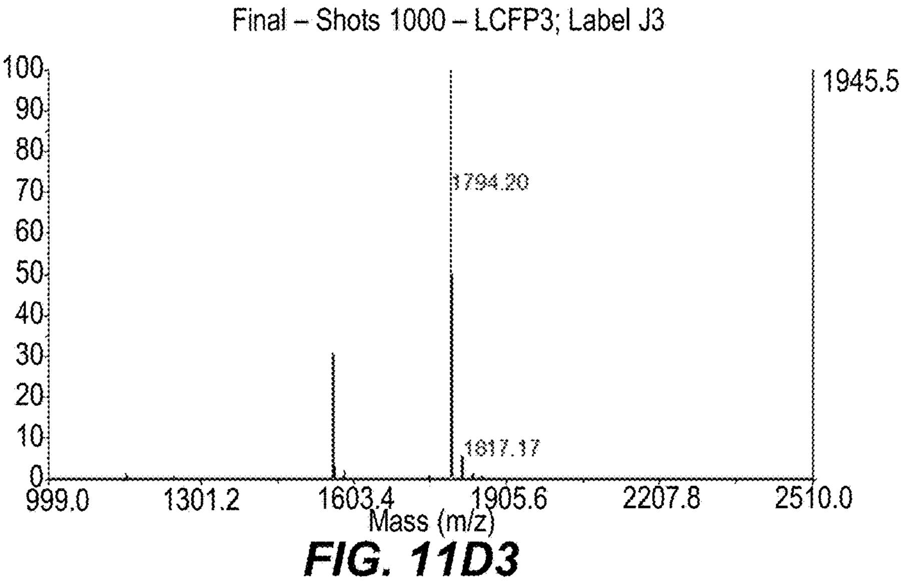
FIG. 11D3
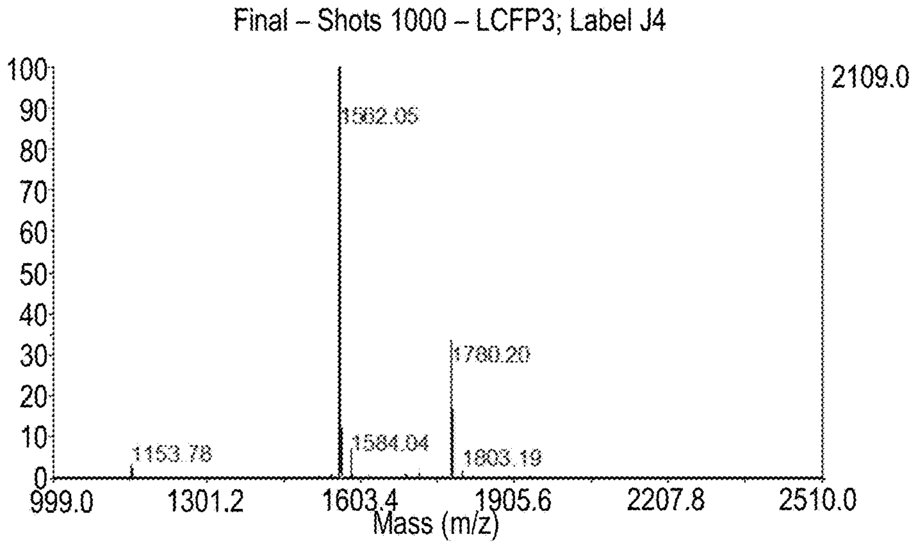
FIG. 11D4

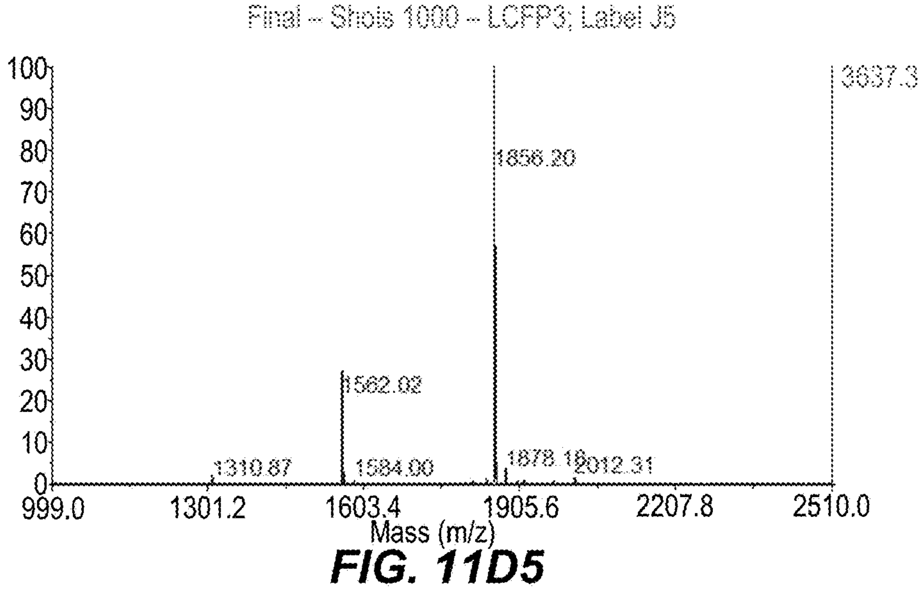
FIG. 11D5
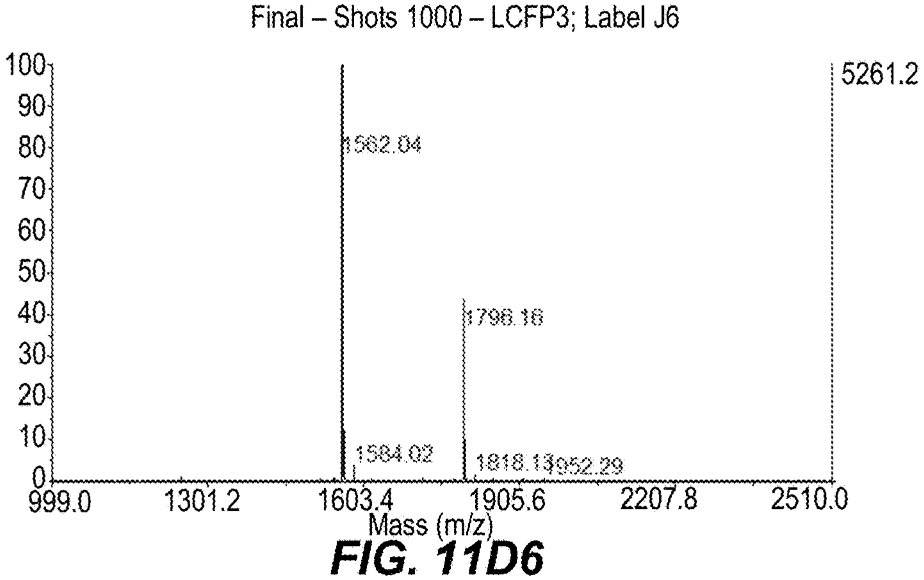
FIG. 11D6
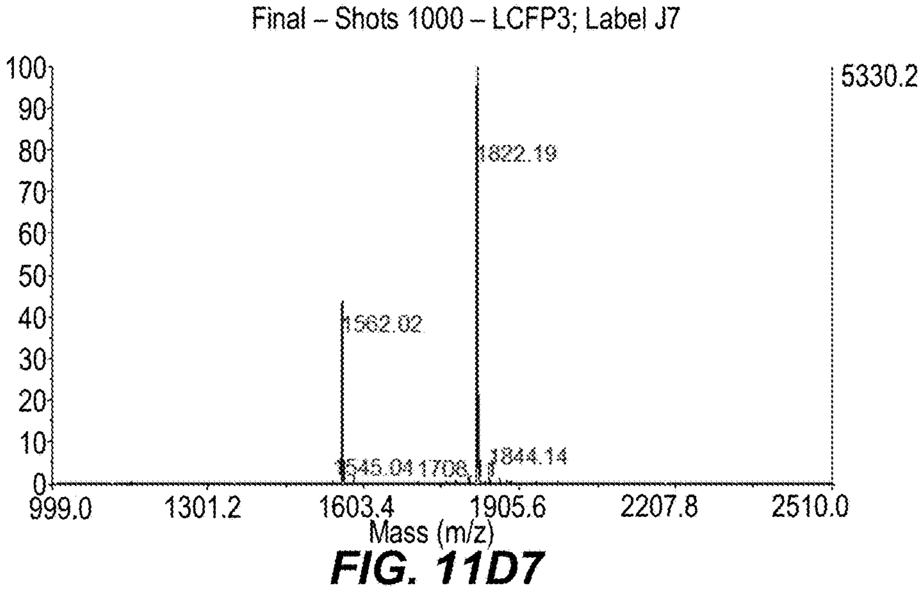
FIG. 11D7

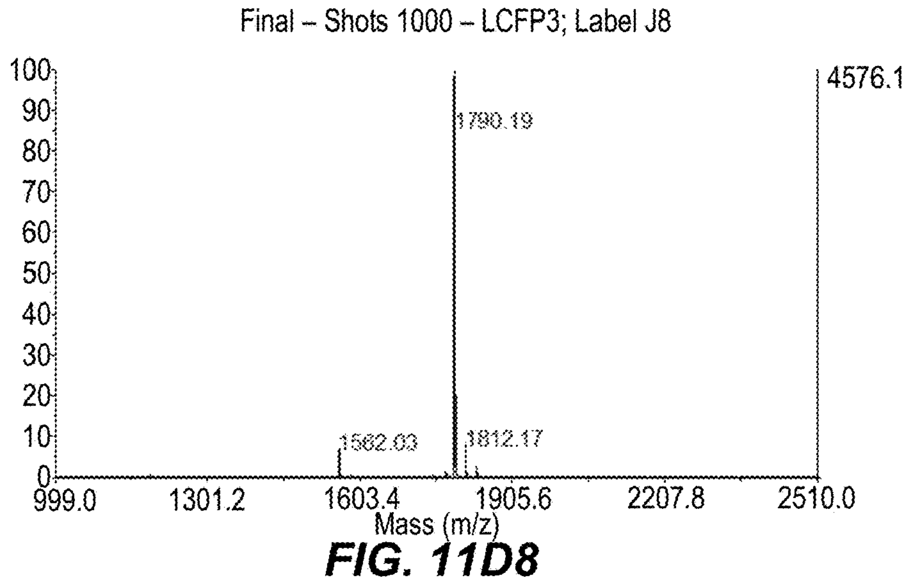
*FIG. 11D8*
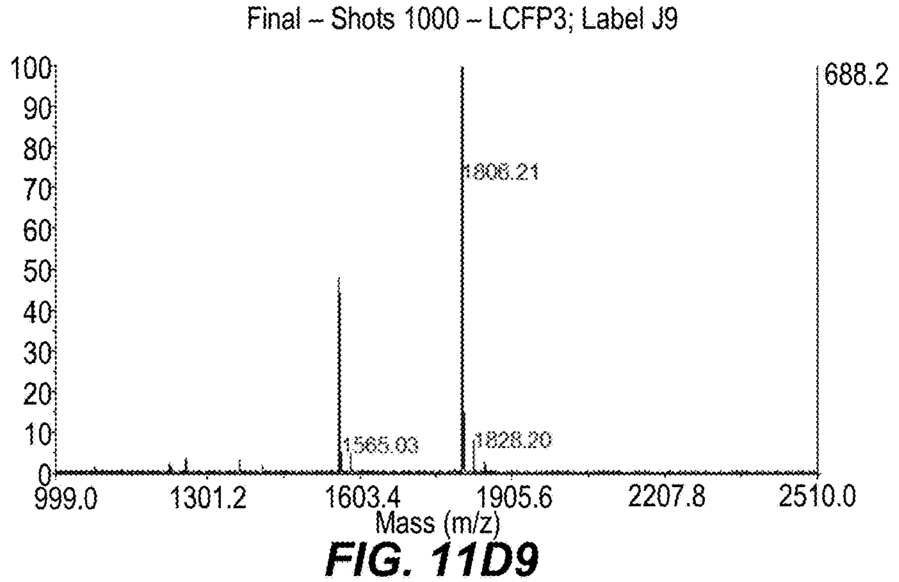
*FIG. 11D9*
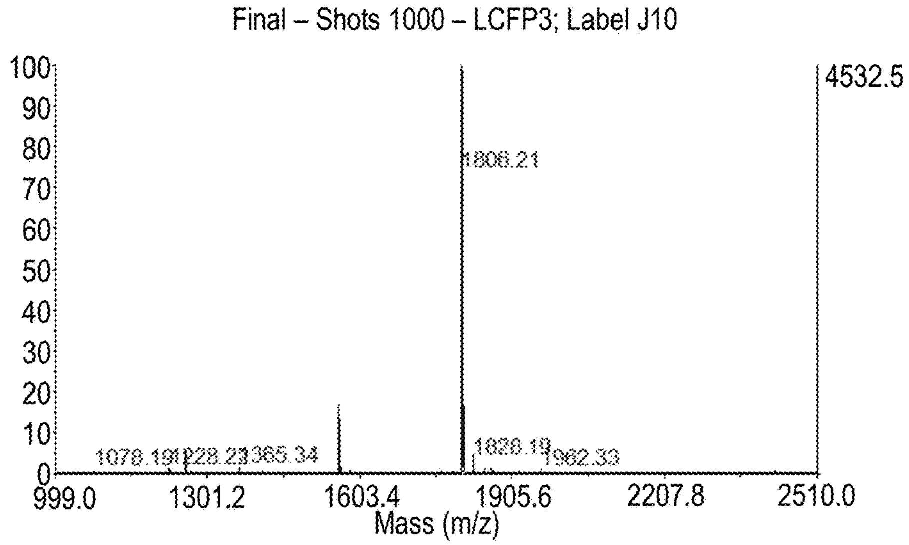
*FIG. 11D10*

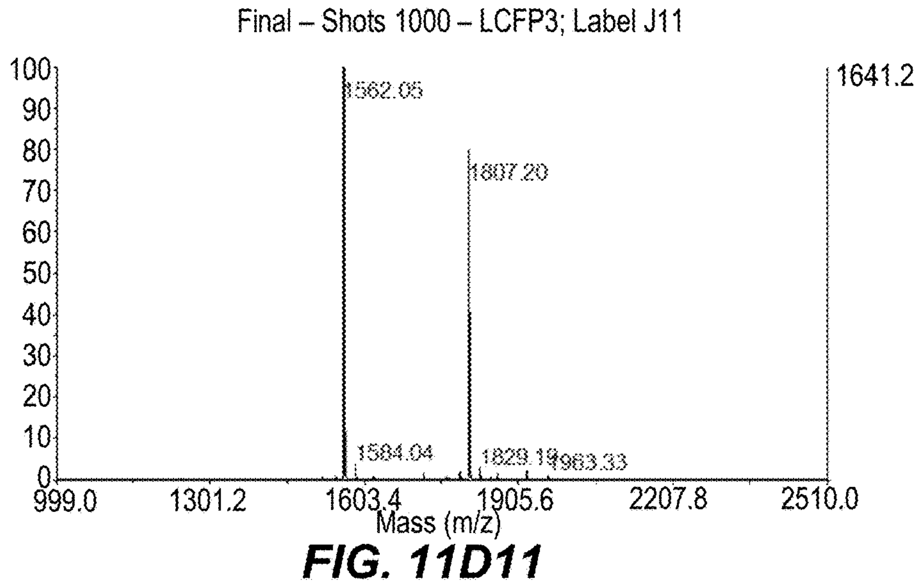
FIG. 11D11
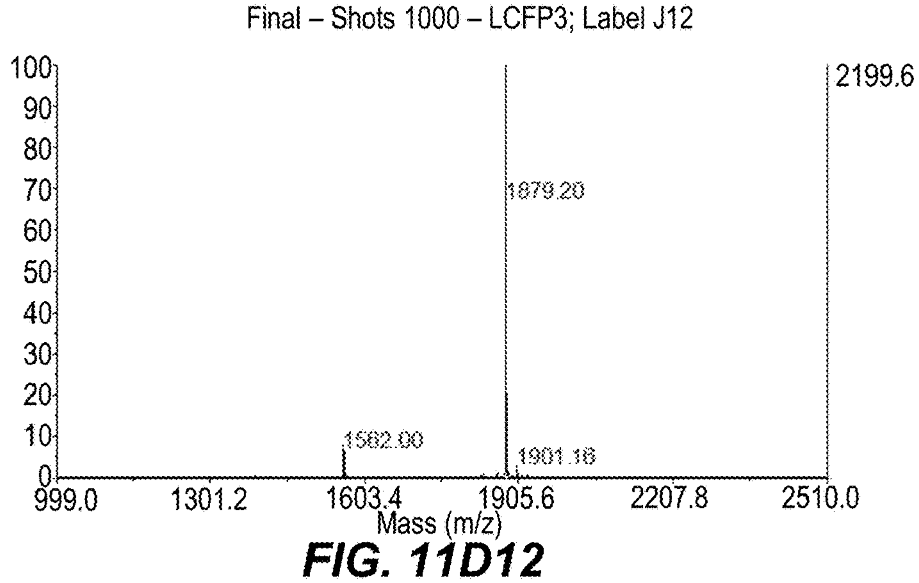
FIG. 11D12
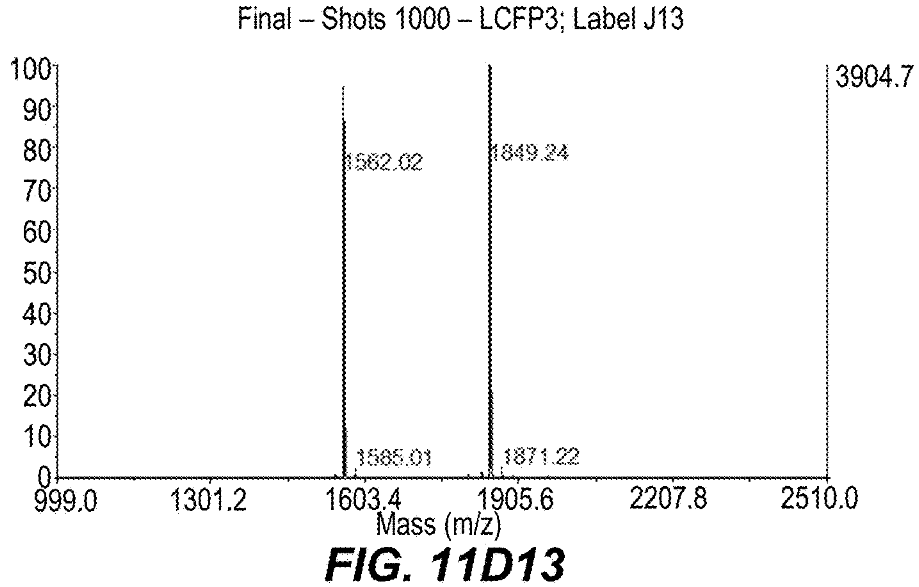
FIG. 11D13

Final – Shots 1000 – LCFP3; Label J14
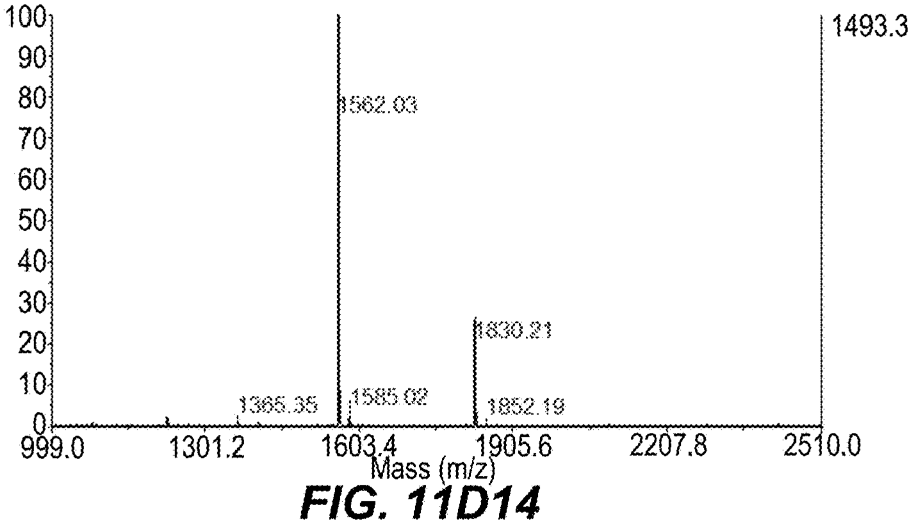
*FIG. 11D14*
Final – Shots 1000 – LCFP3; Label J15
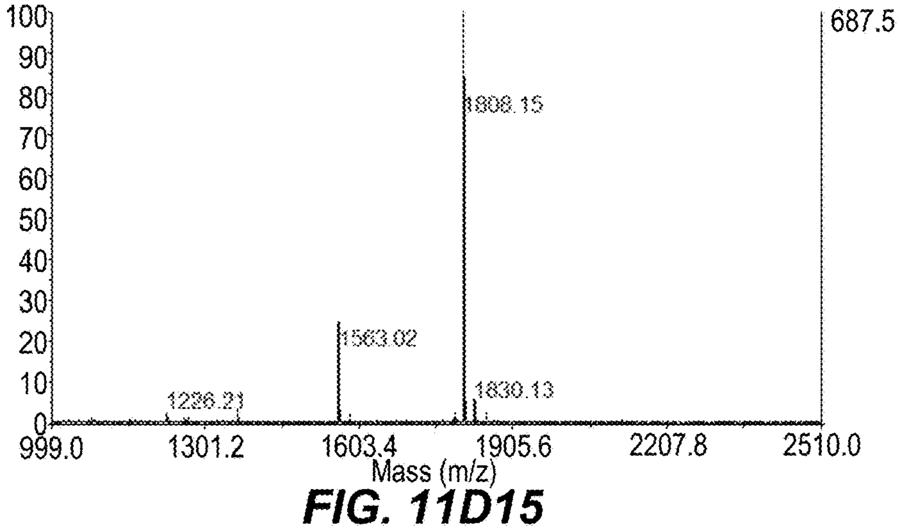
*FIG. 11D15*
Final – Shots 1000 – LCFP3; Label J16
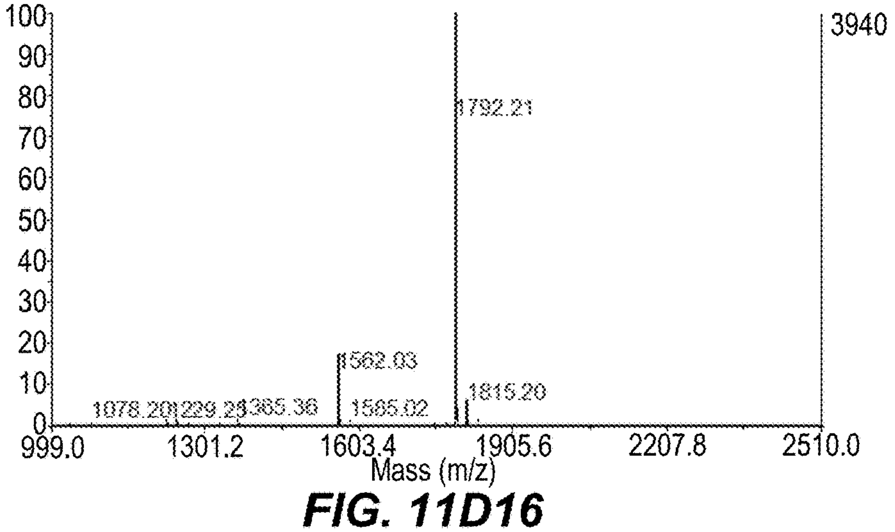
*FIG. 11D16*

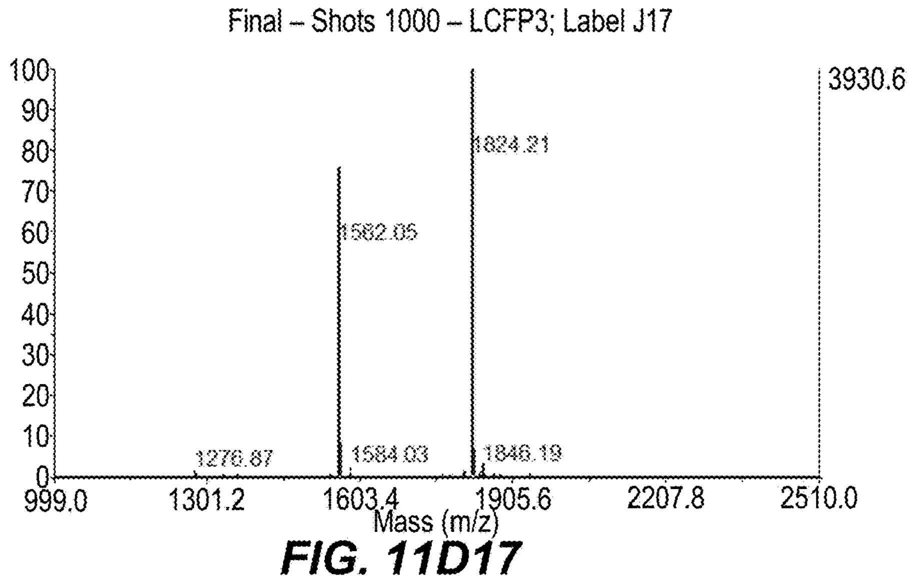
FIG. 11D17
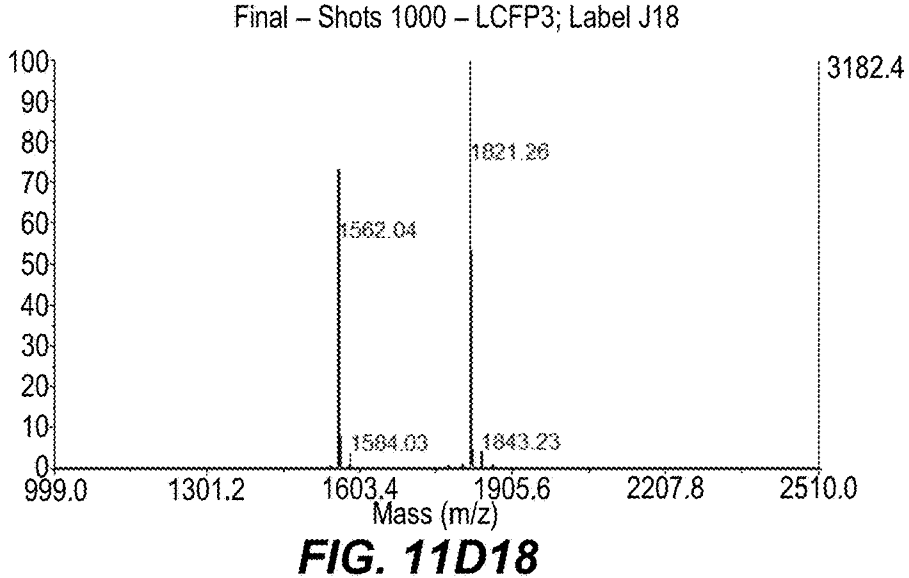
FIG. 11D18
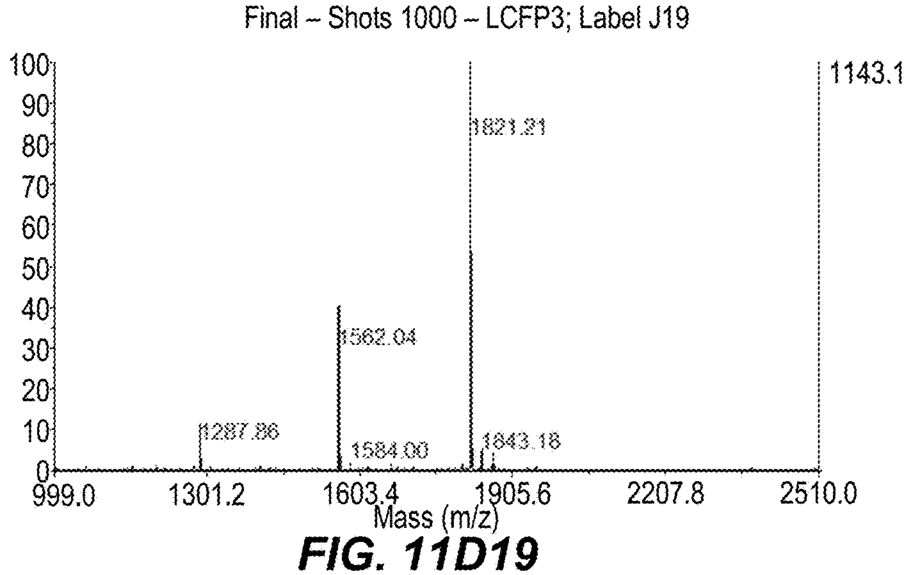
FIG. 11D19

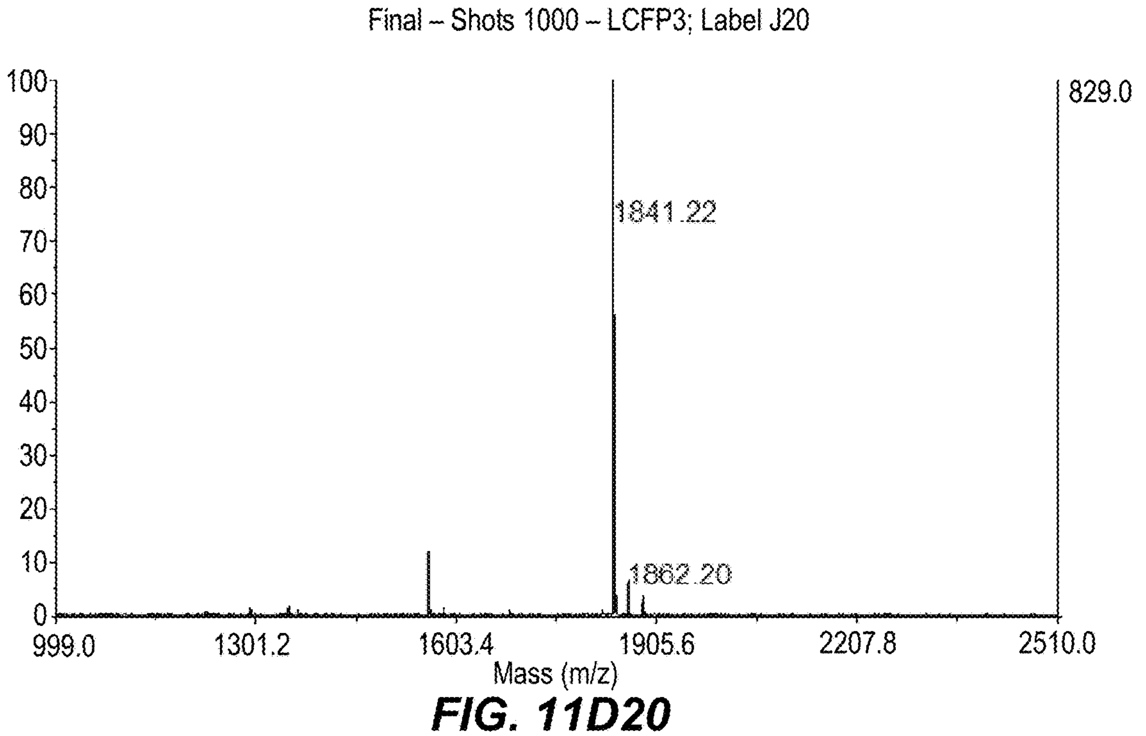
*FIG. 11D20*
GLYRRGRLYRRNGX (J21-L16: NGG, NGA, NGT, NGS, NGY, NGC, NGE, NGP, NGI, NGN, NGW, NGR, NGH, NGD, NGV, NGM, NGK, NGQ, NGF total 19 peptides, NGL is the same peptide as the first plot-J1)
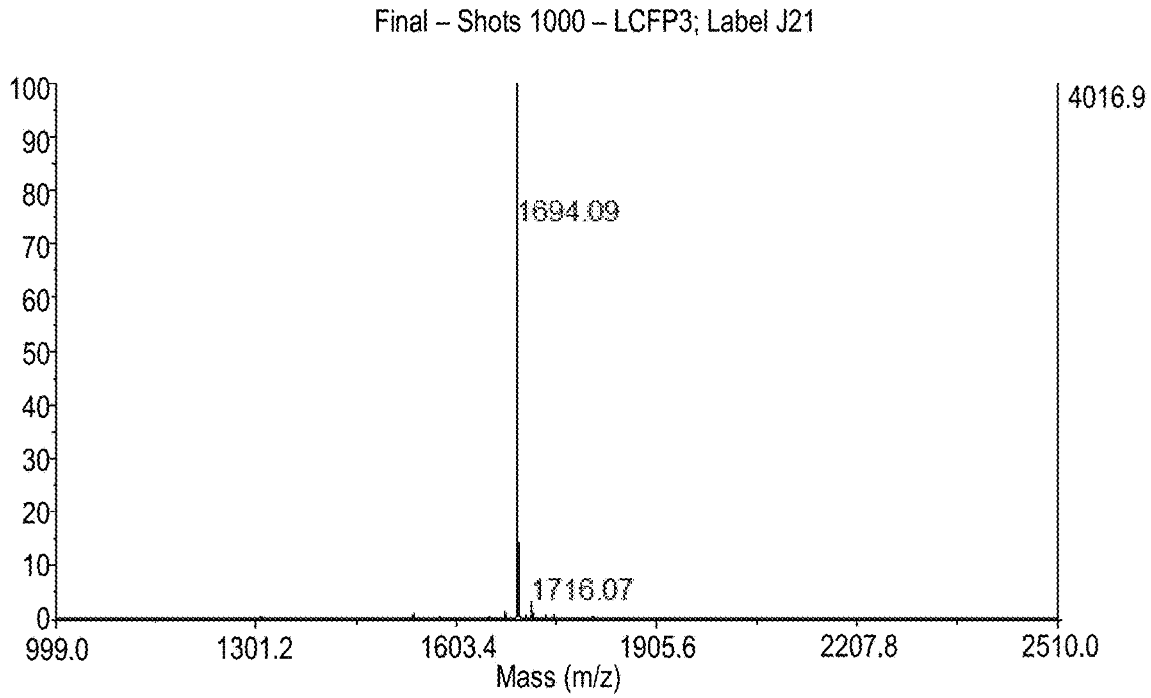
*FIG. 11D21*

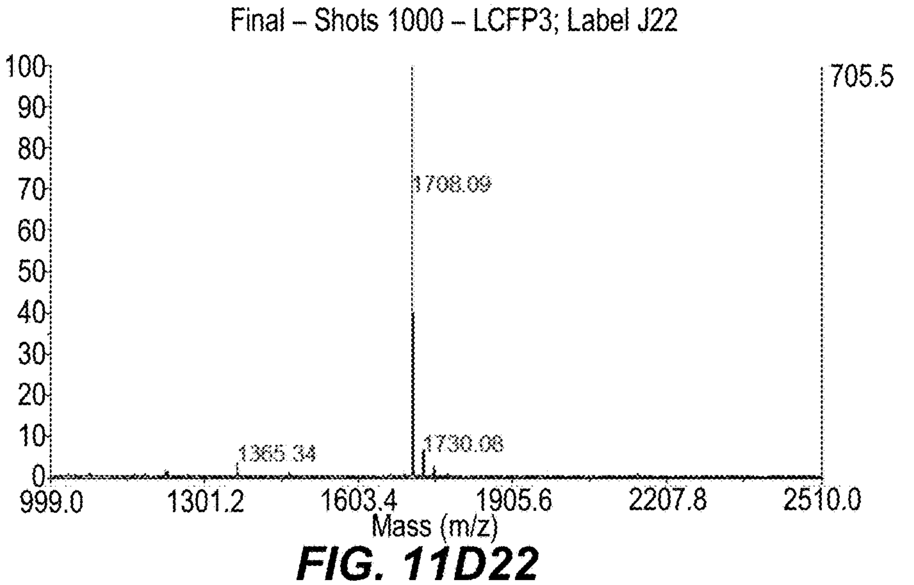
FIG. 11D22
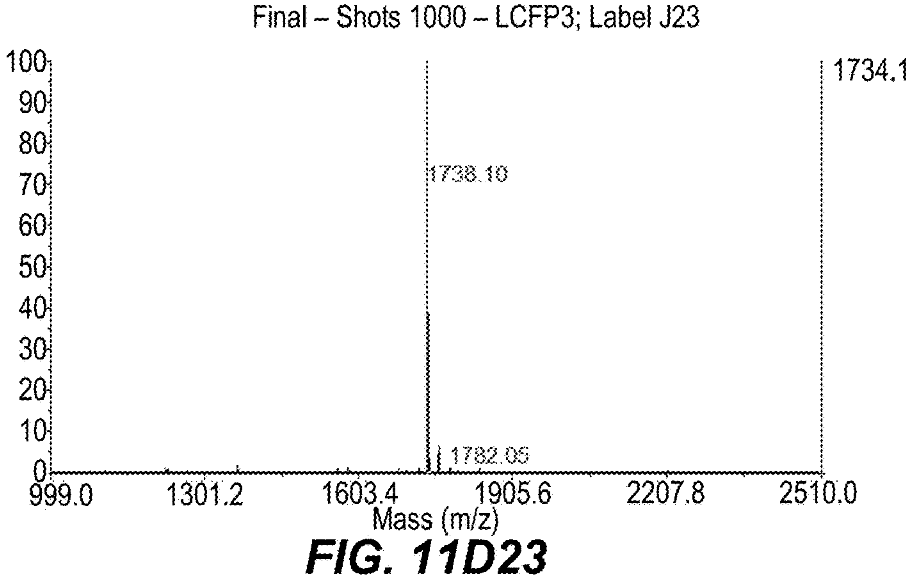
FIG. 11D23
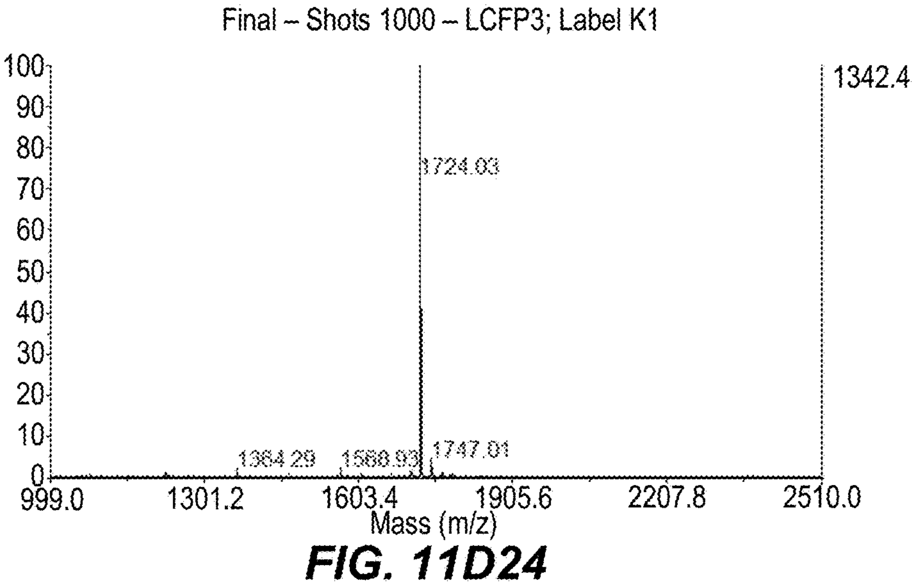
FIG. 11D24

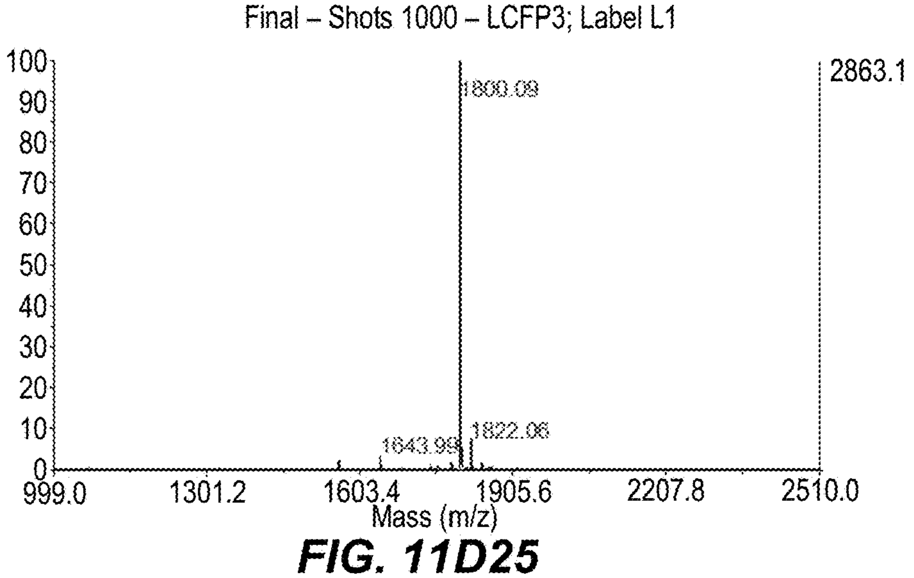
FIG. 11D25
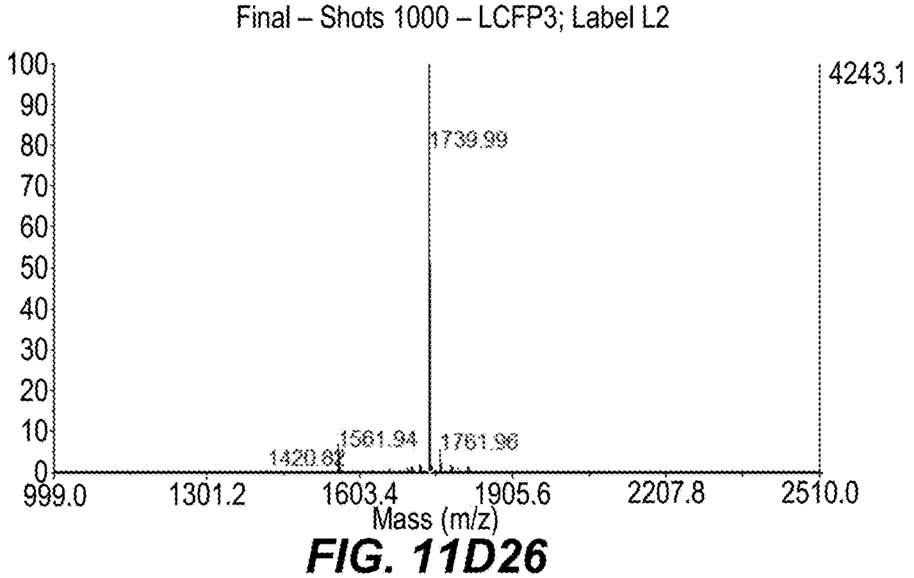
FIG. 11D26
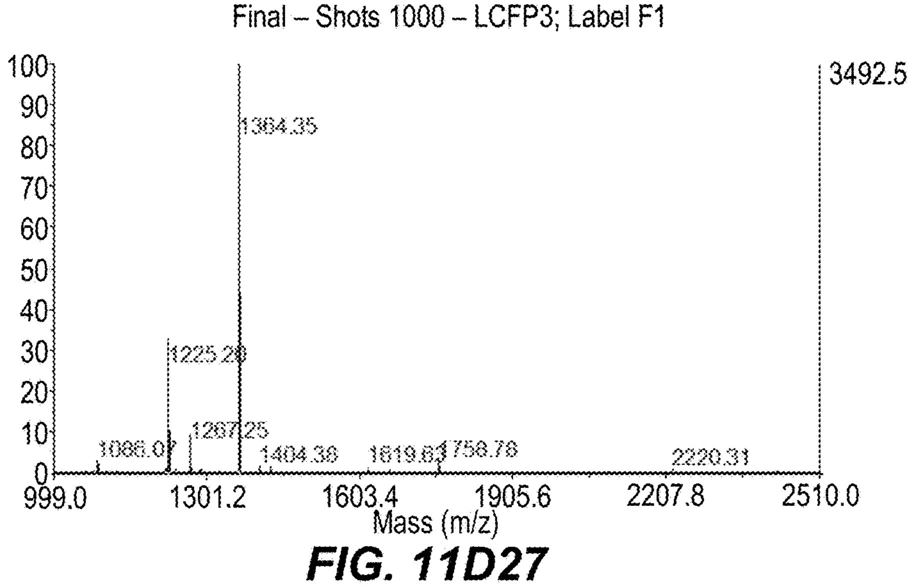
FIG. 11D27

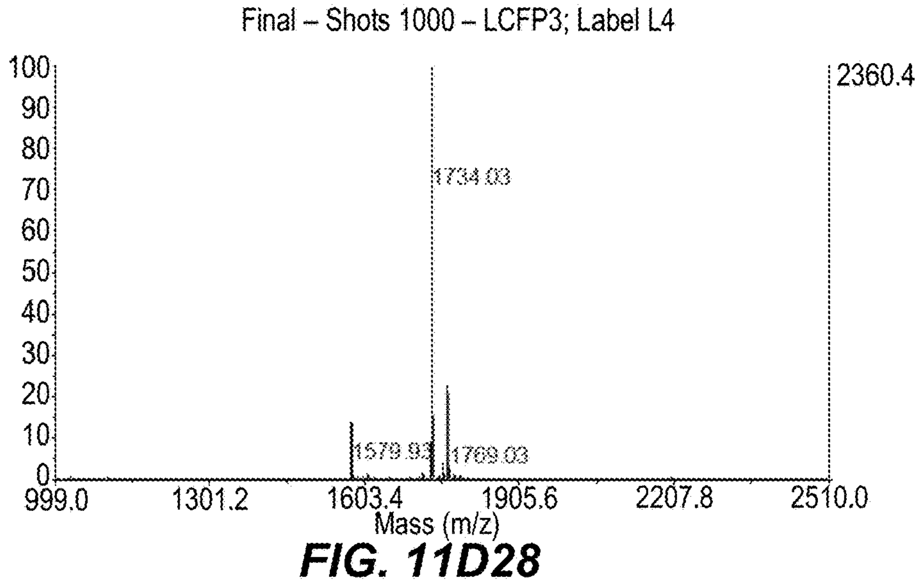
FIG. 11D28
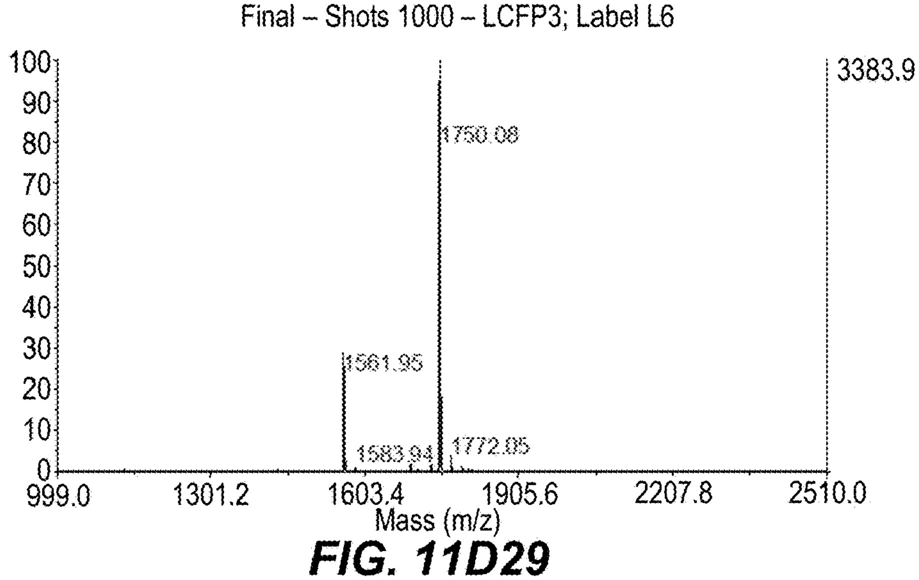
FIG. 11D29
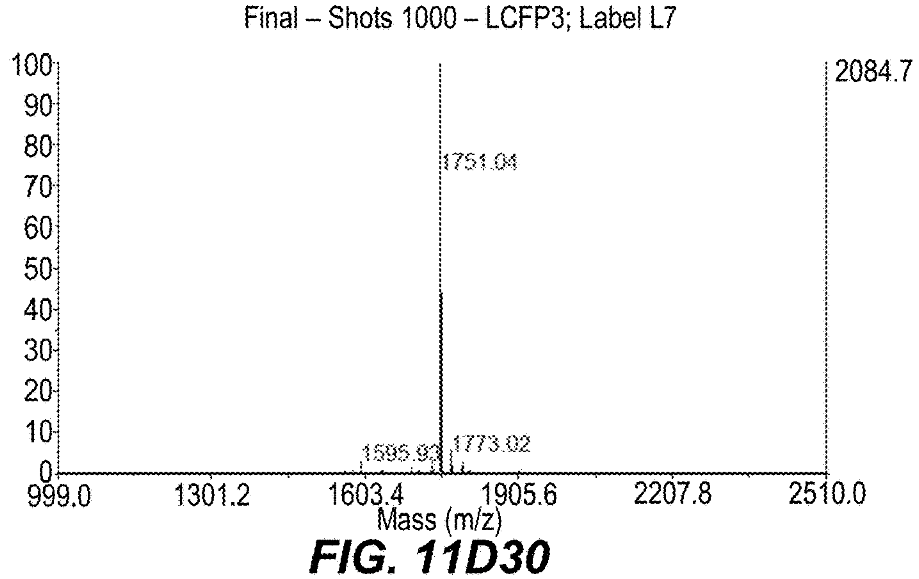
FIG. 11D30

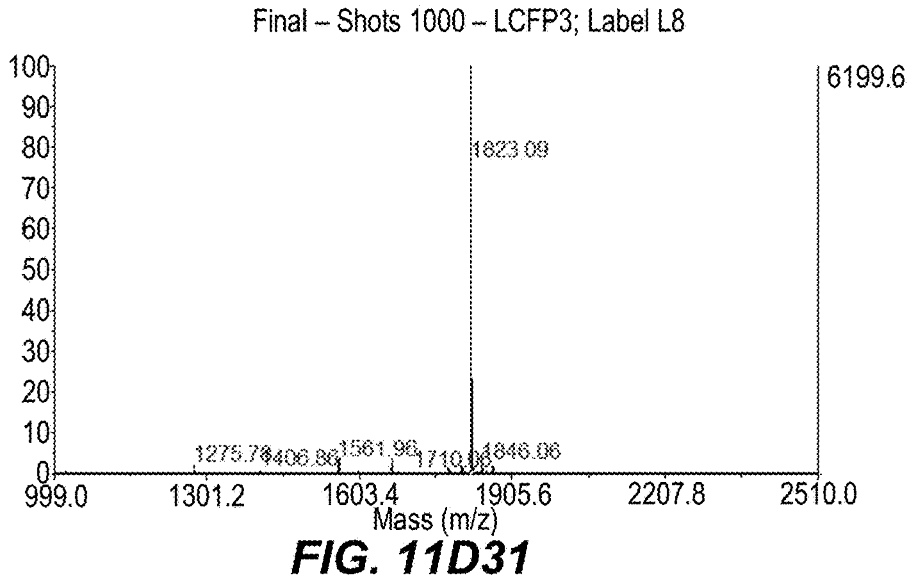
FIG. 11D31
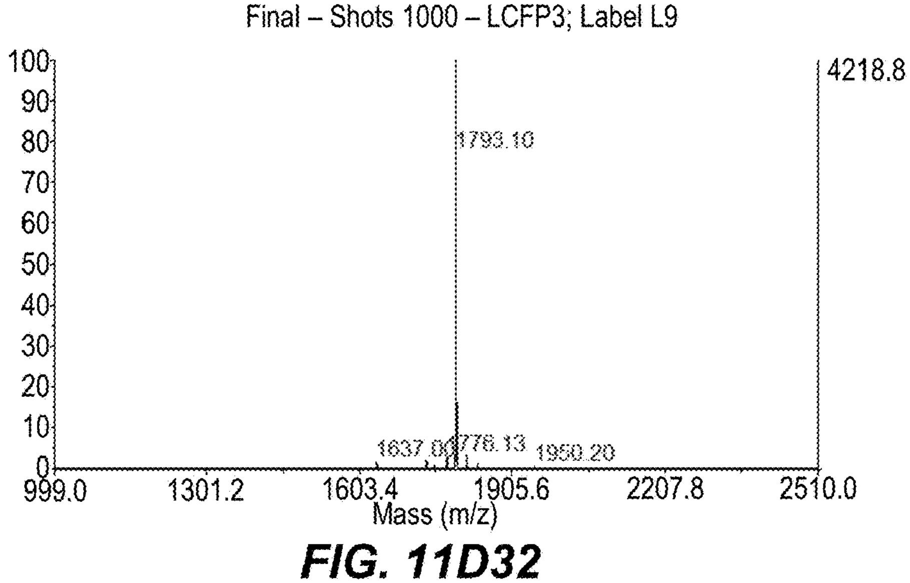
FIG. 11D32
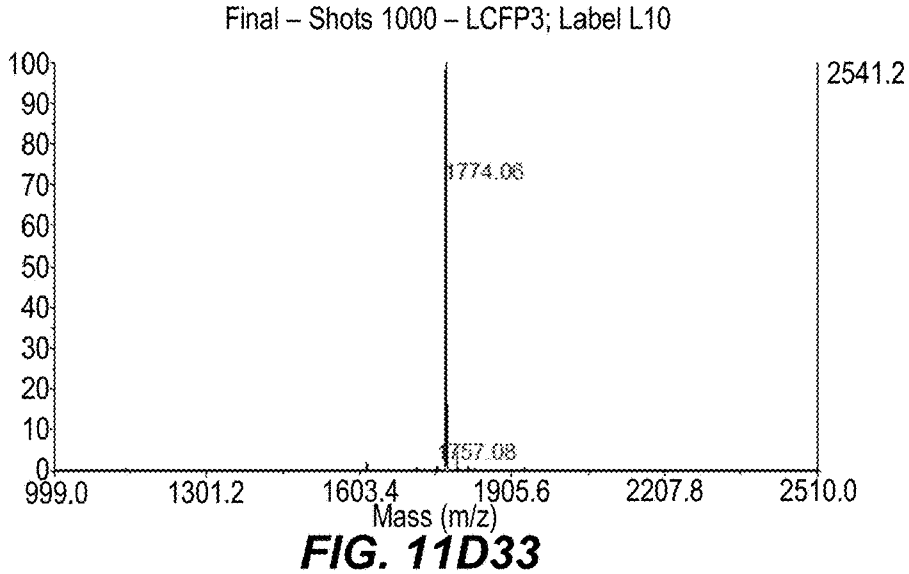
FIG. 11D33

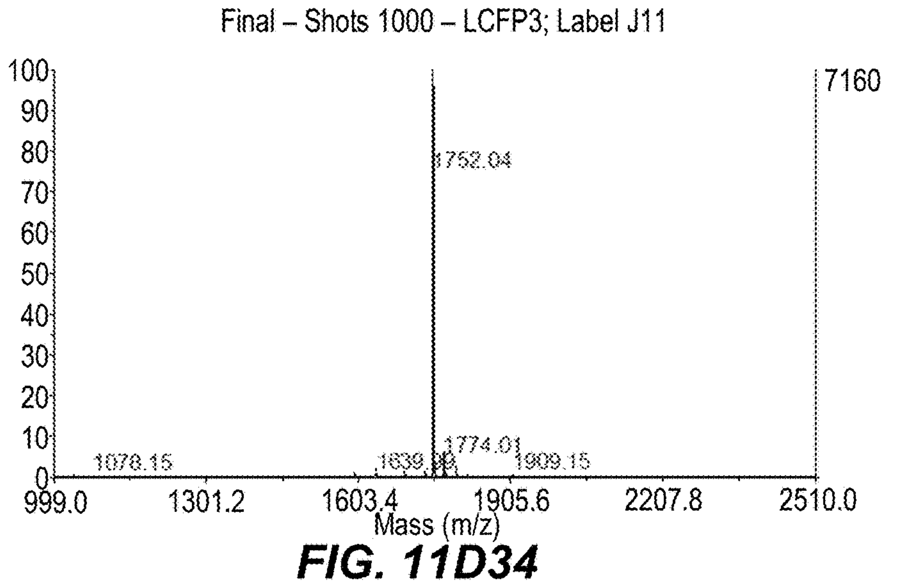
*FIG. 11D34*
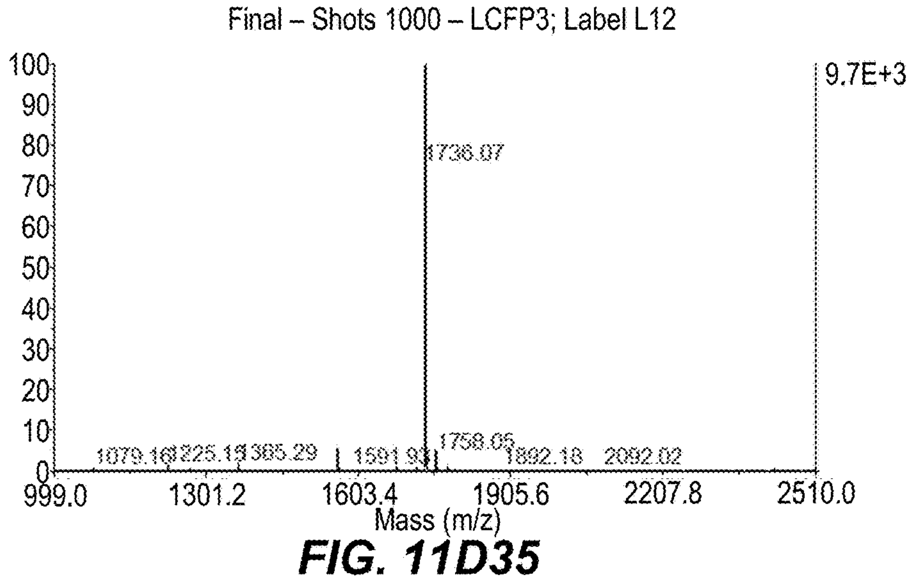
*FIG. 11D35*
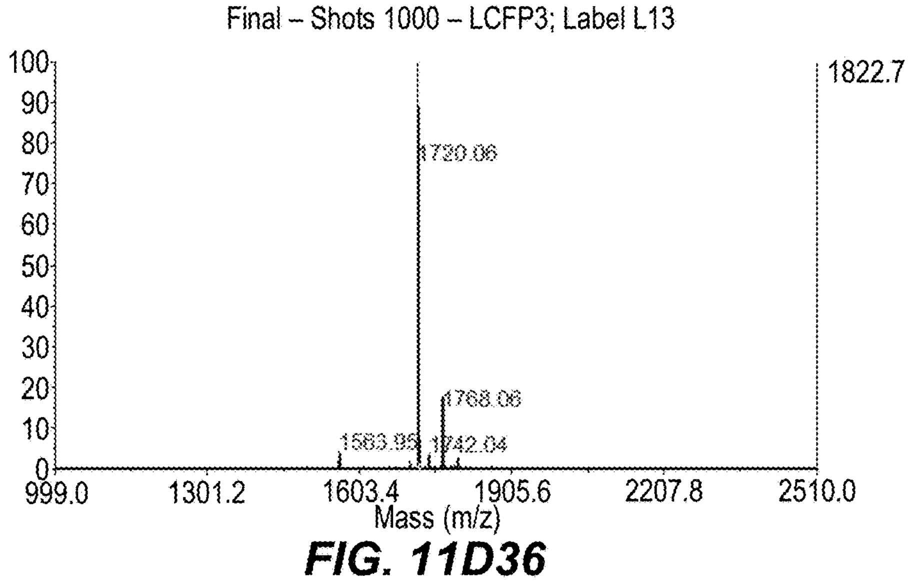
*FIG. 11D36*

Final – Shots 1000 – LCFP3; Label L14
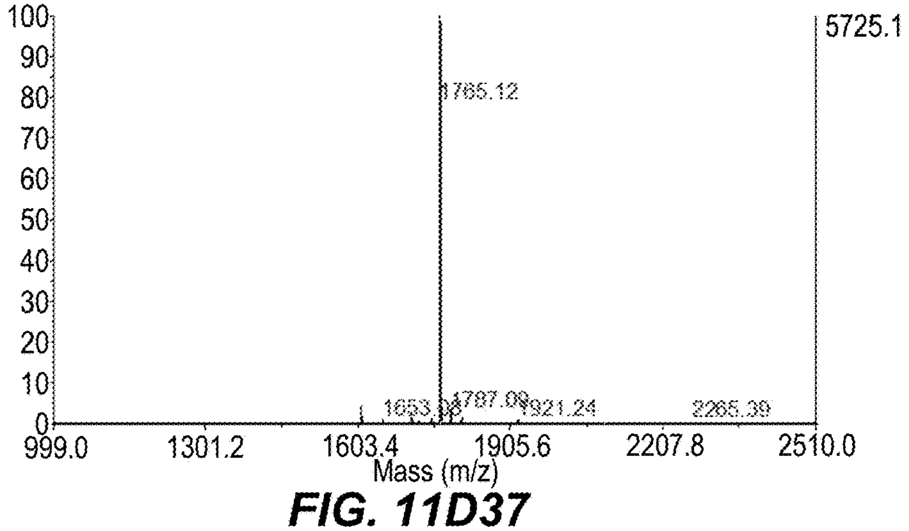
*FIG. 11D37*
Final – Shots 1000 – LCFP3; Label L15
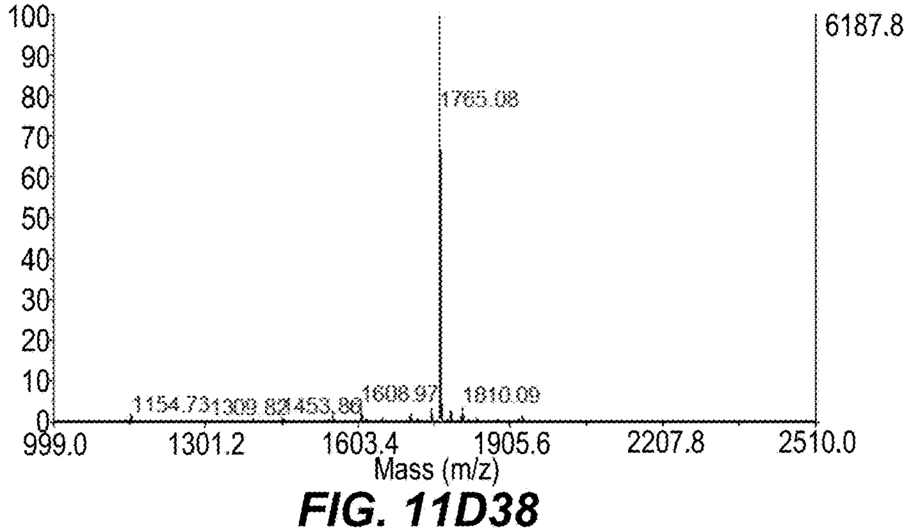
*FIG. 11D38*
Final – Shots 1000 – LCFP3; Label L16
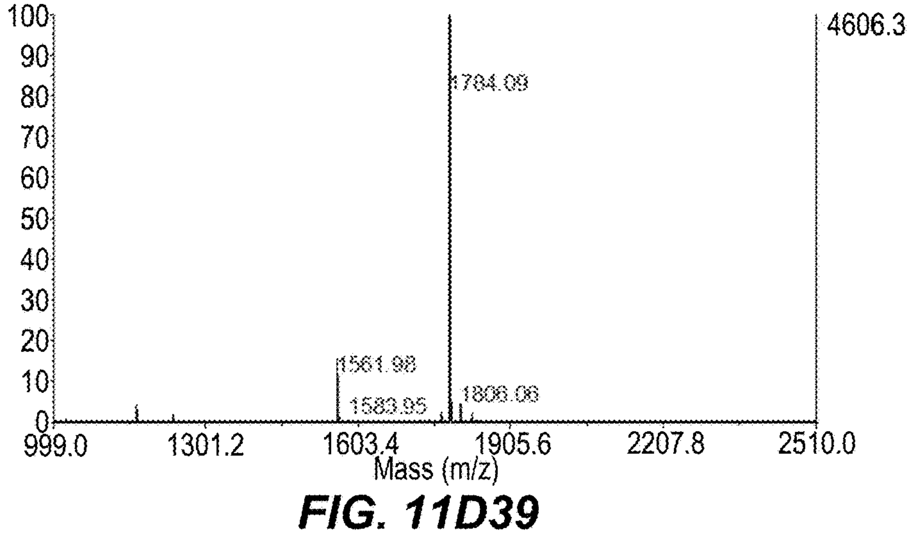
*FIG. 11D39*

GL PVSTKPVATRDAL cyclization for 5 min, when replacing the Asn in NAL sequence with Asp in DAL sequence. The ligation is less efficient but still robust enough.
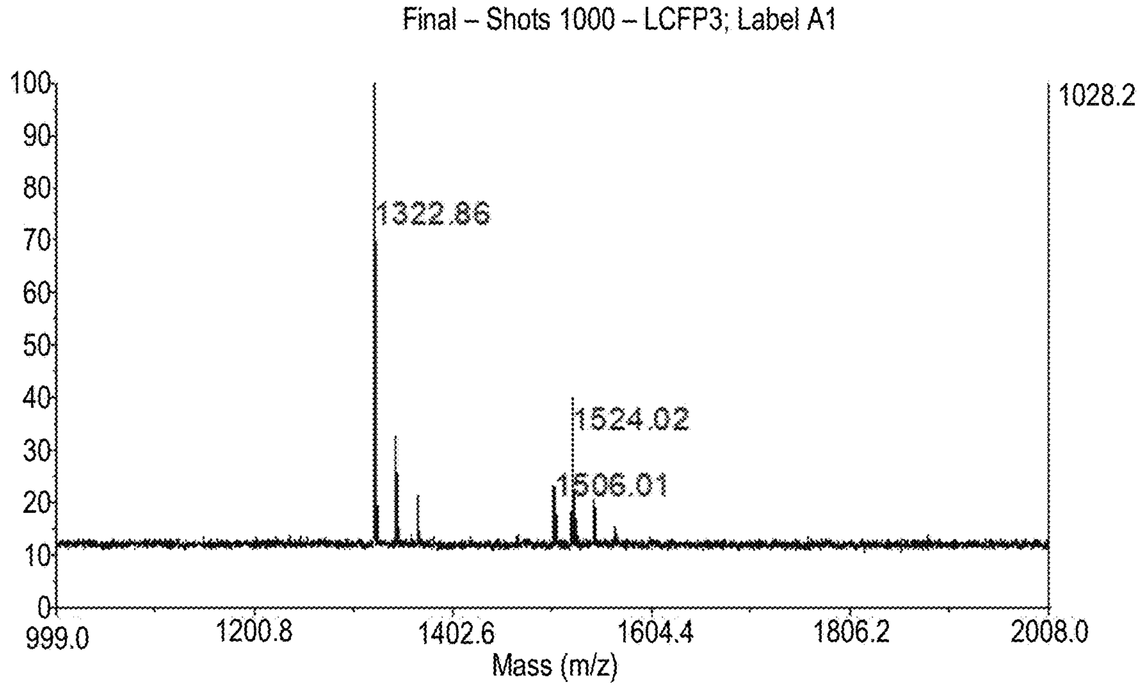
*FIG. 11D40*
XLYRRGRLYRRNAL (L1-L20: VL, ML, GL, RL, QL, WL, EL, PL, DL, TL, SL, AL, IL, NL, KL, CL, YL, HL, FL, LL)
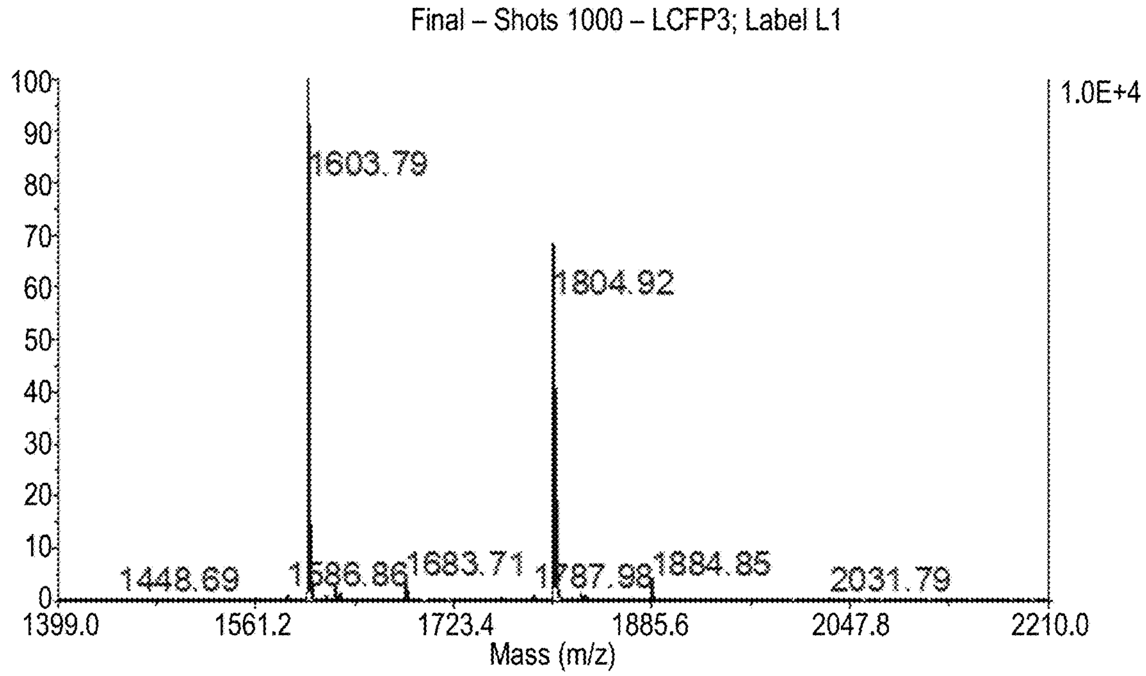
*FIG. 11D41*

Final – Shots 1000 – LCFP3; Label L2
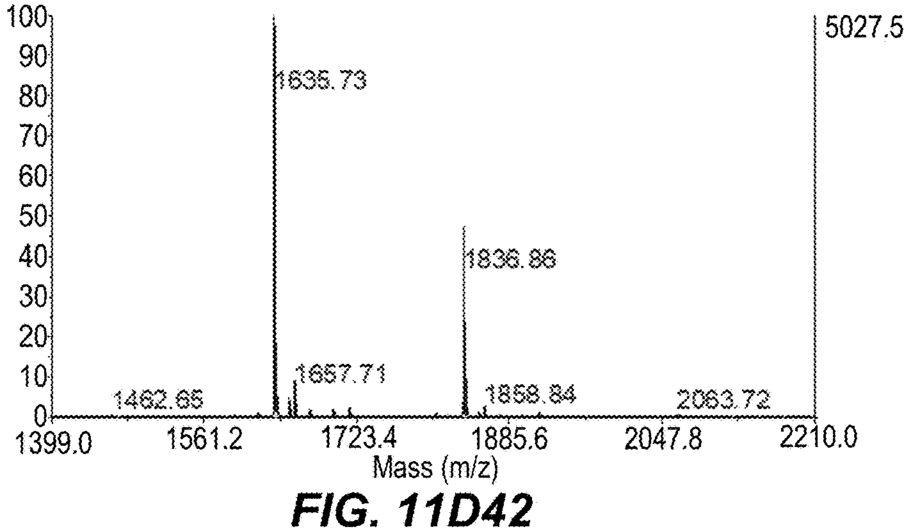
*FIG. 11D42*
Final – Shots 1000 – LCFP3; Label L3
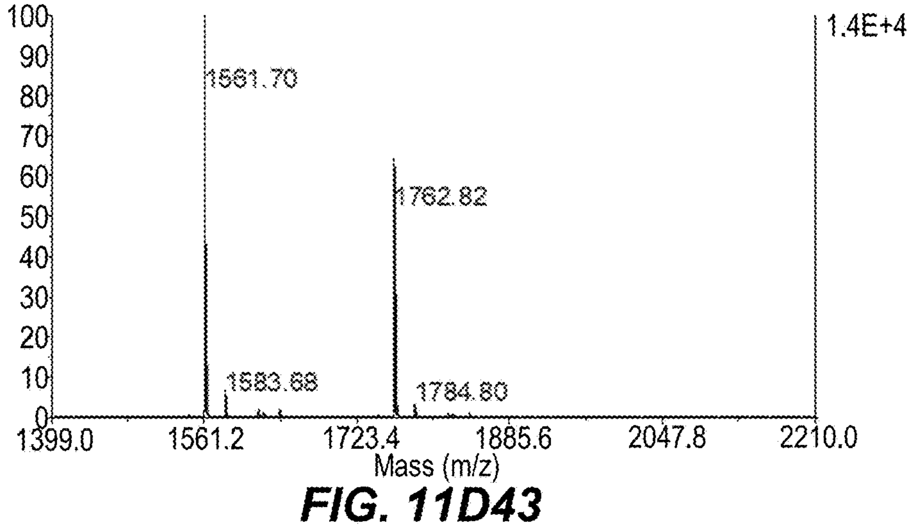
*FIG. 11D43*
Final – Shots 1000 – LCFP3; Label L4
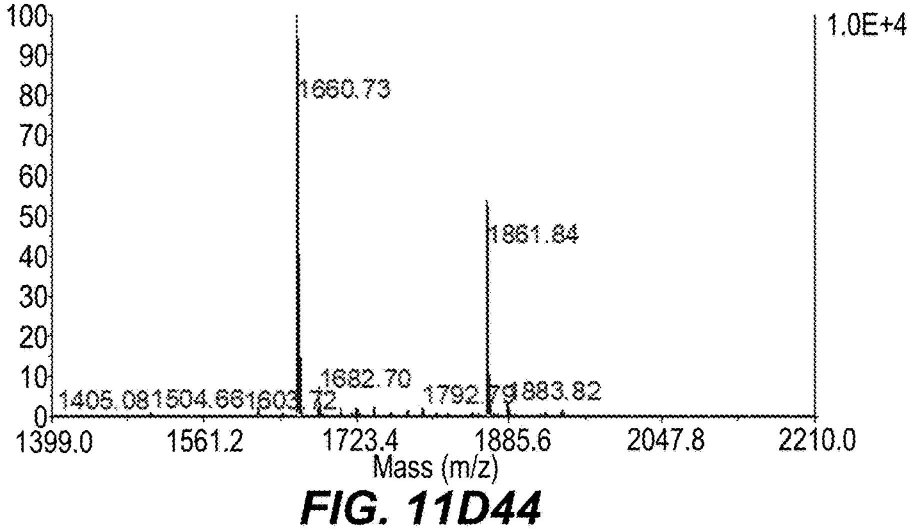
*FIG. 11D44*

Final – Shots 1000 – LCFP3; Label L5
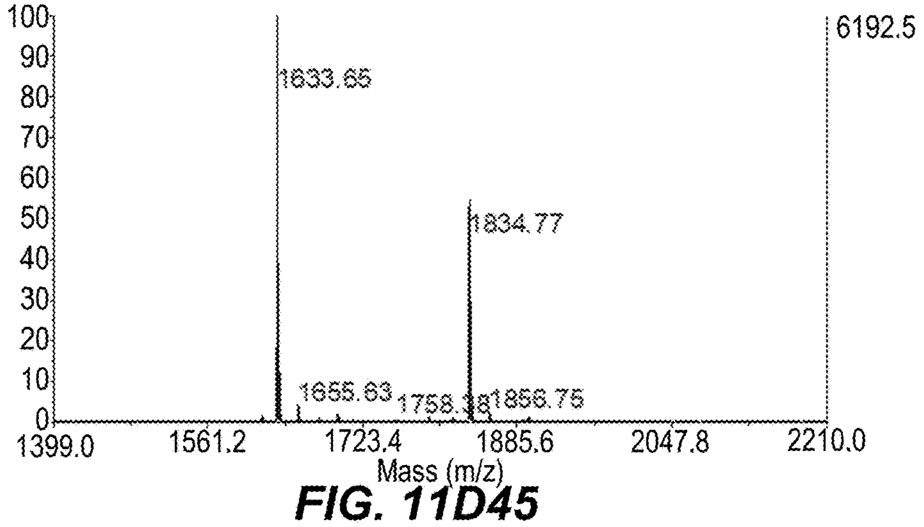
FIG. 11D45
Final – Shots 1000 – LCFP3; Label L6
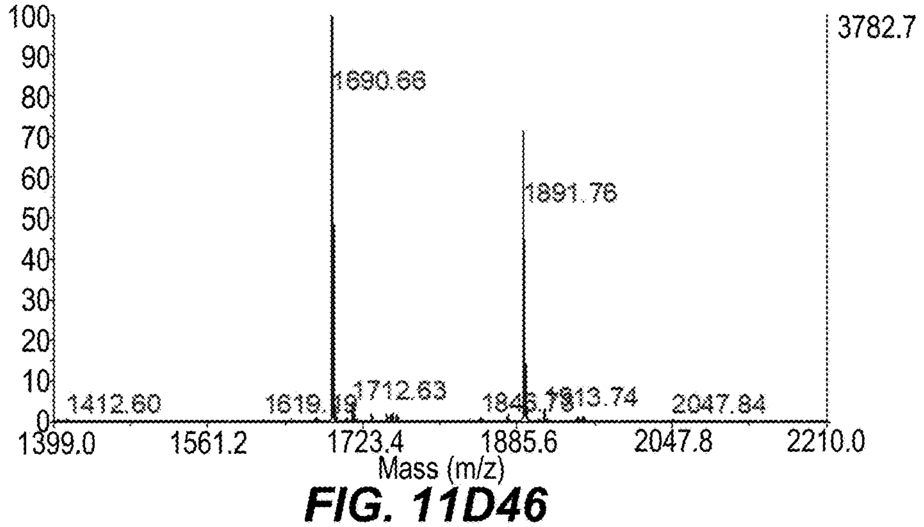
FIG. 11D46
Final – Shots 1000 – LCFP3; Label L7
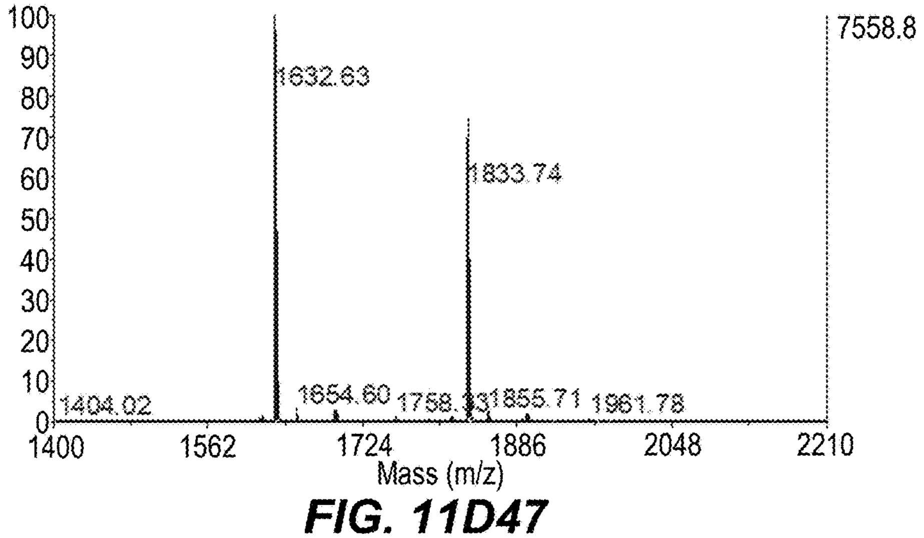
FIG. 11D47

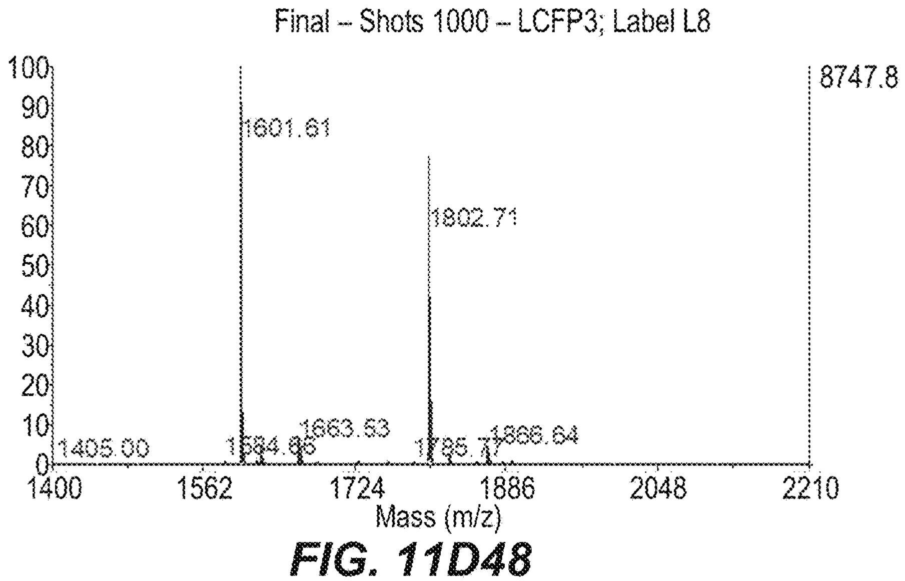
FIG. 11D48
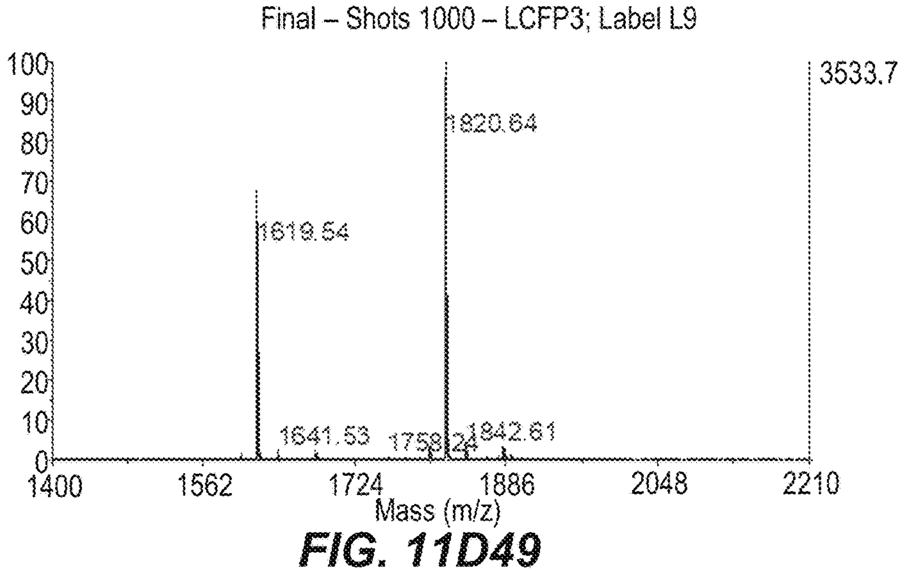
FIG. 11D49
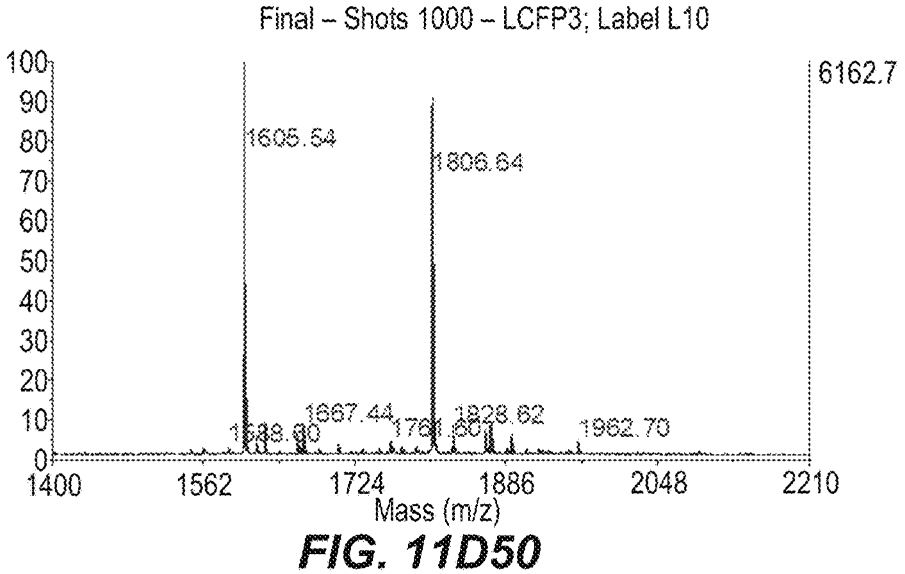
FIG. 11D50

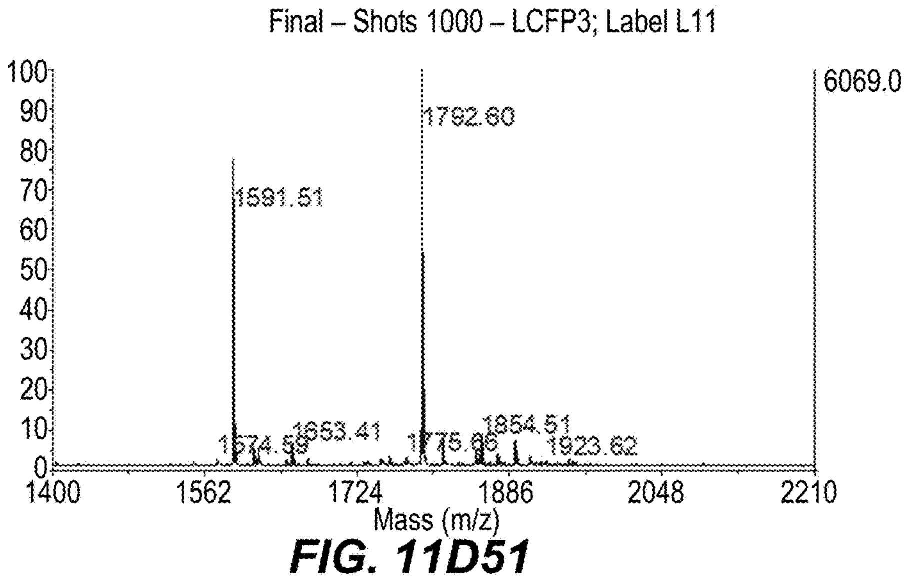
FIG. 11D51
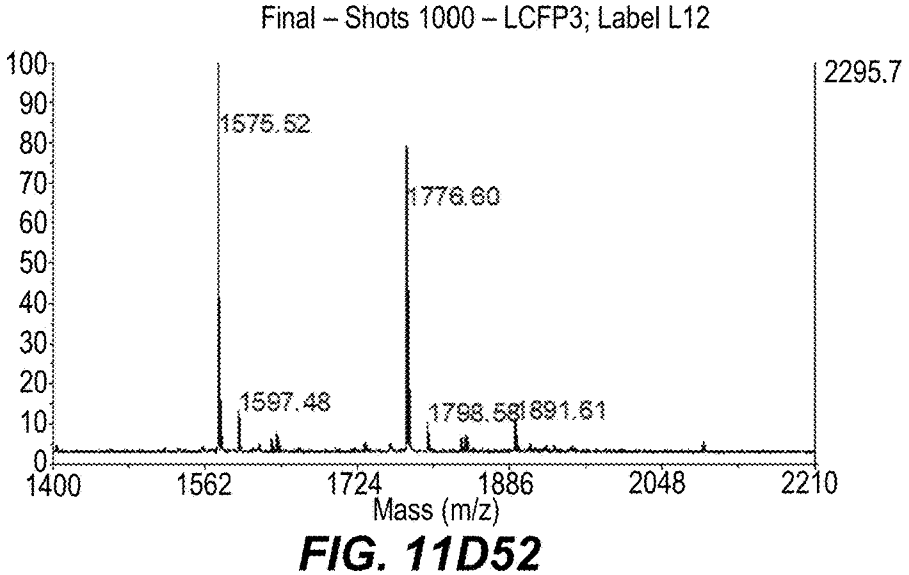
FIG. 11D52
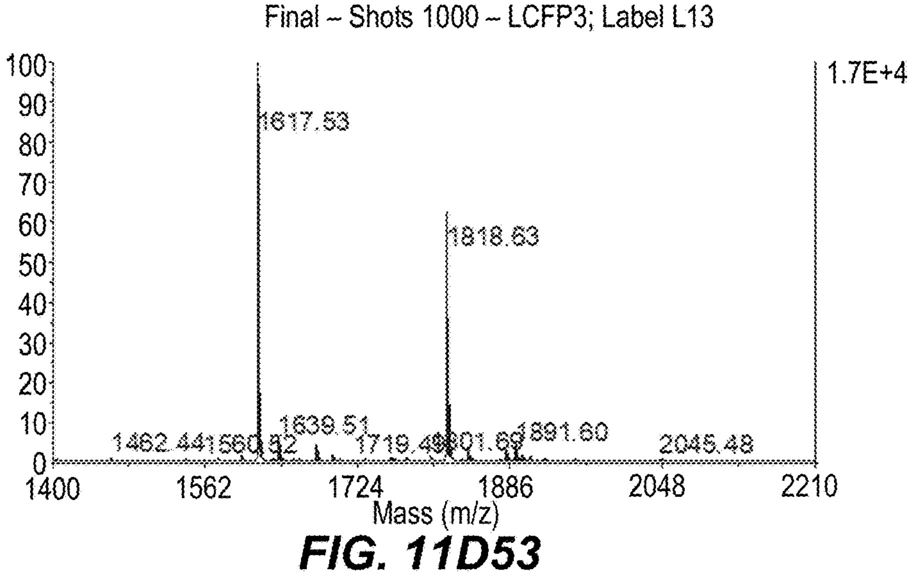
FIG. 11D53

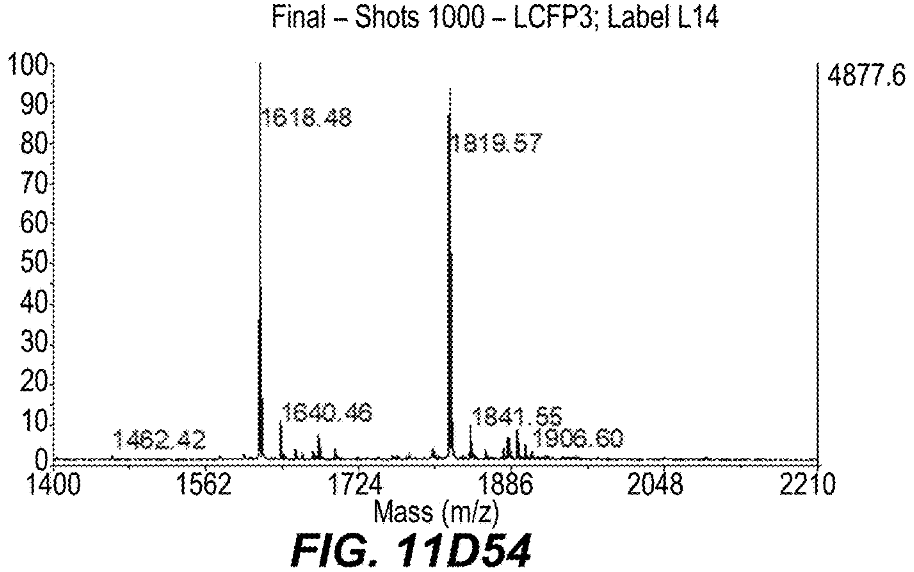
*FIG. 11D54*
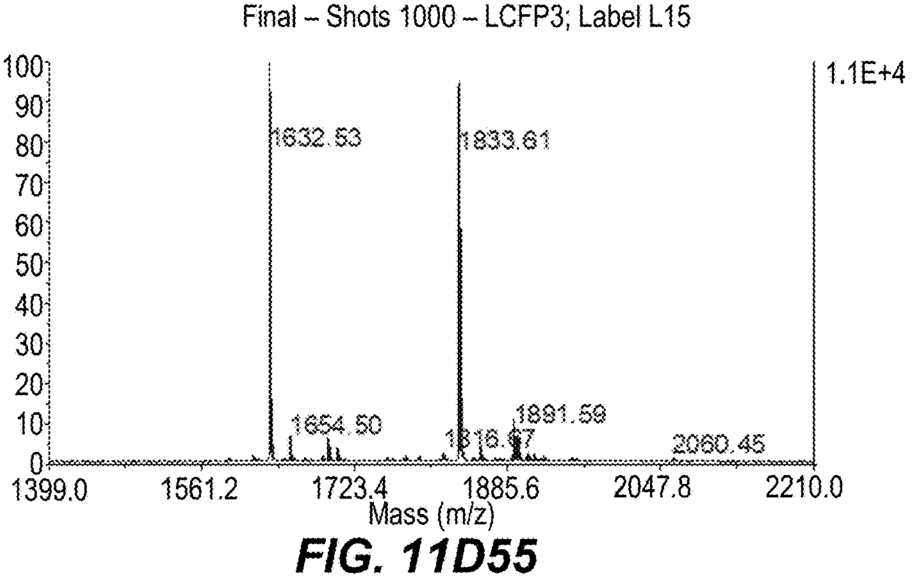
*FIG. 11D55*
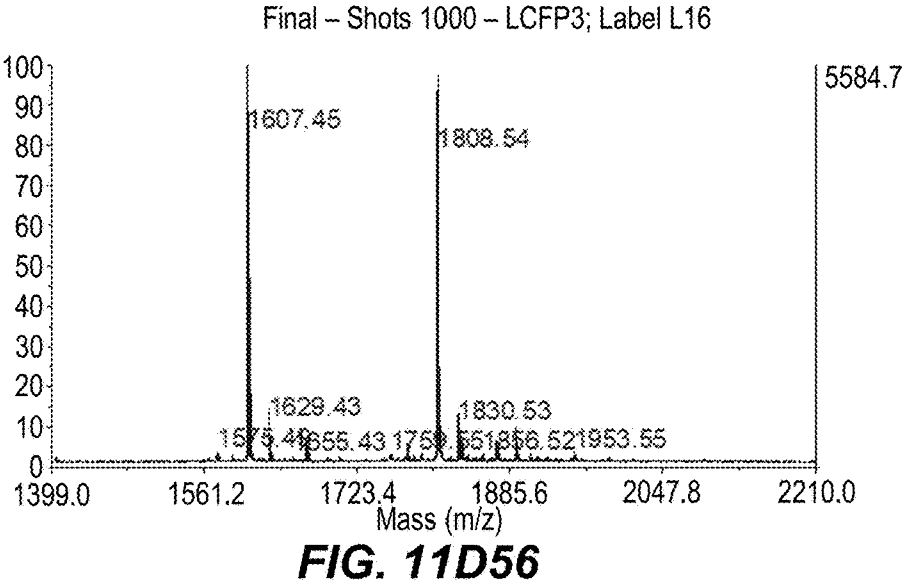
*FIG. 11D56*

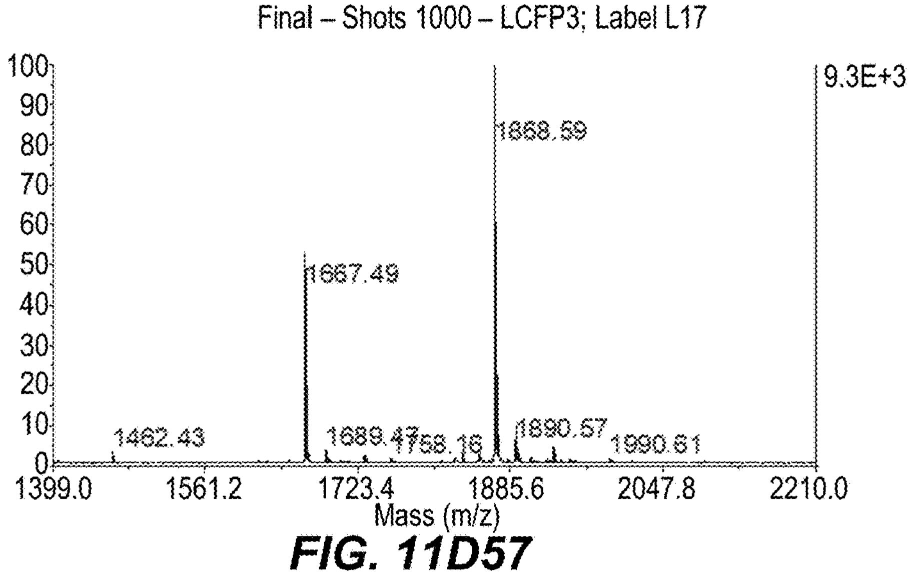
FIG. 11D57
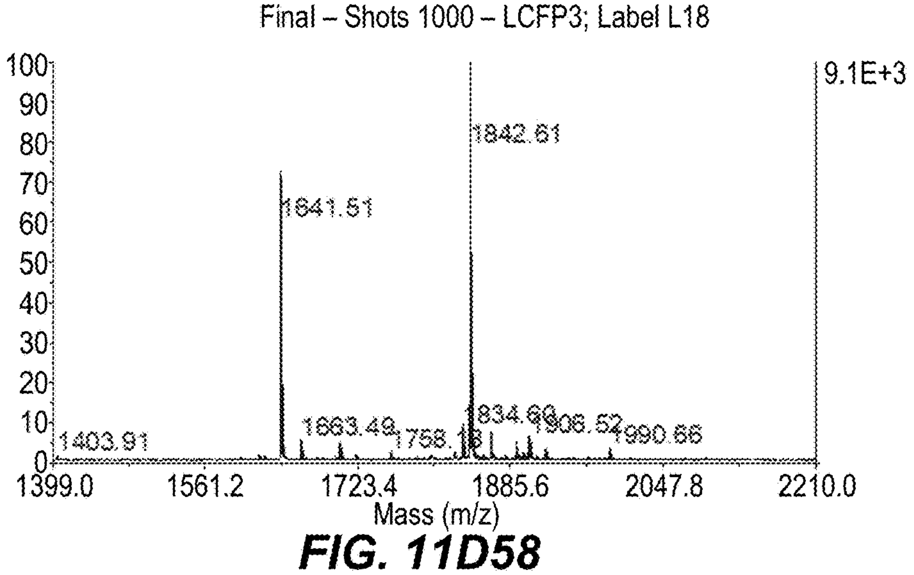
FIG. 11D58
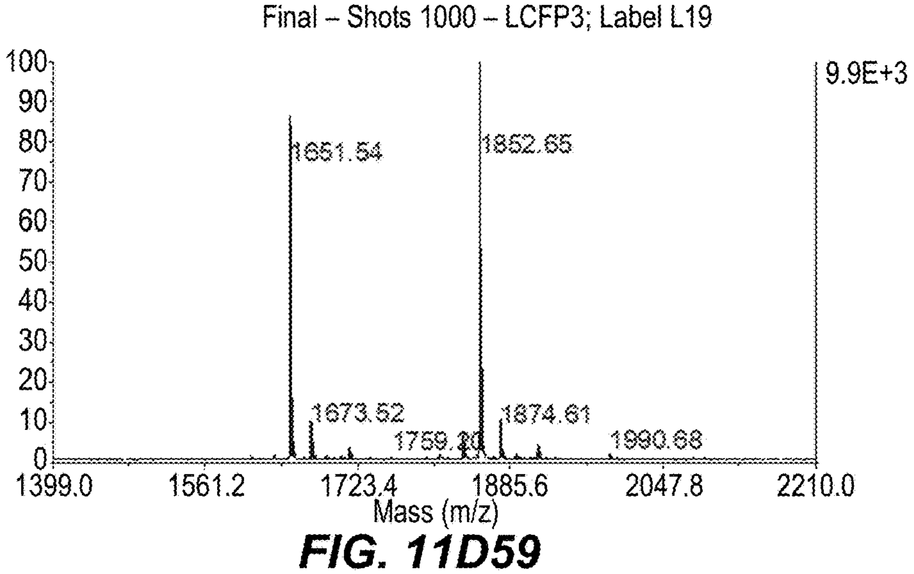
FIG. 11D59

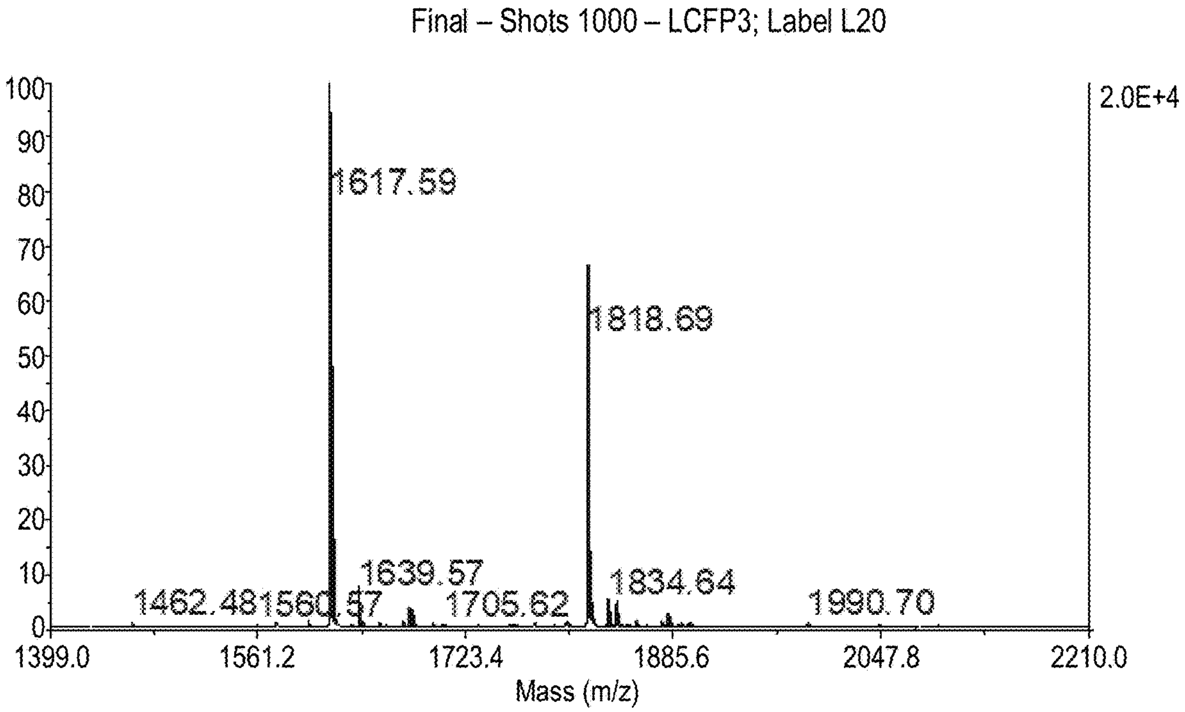
*FIG. 11D60*

FIG. 12A

BLAST Results

Blast 2 sequences

Job title: Protein Sequence (474 letters)

RID HUCBXSS011N (Expires on 05-19 13:30 pm)

| | | | |
|---|---|---|---|
| **Query ID** | lcl\|Query_162141 | **Subject ID** | 7 subjects |
| **Description** | None | **Description** | See details |
| **Molecule type** | amino acid | **Molecule type** | amino acid |
| **Query Length** | 474 | **Subject Length** | 3432 |
| | | **Program** | BLASTP 2.6.1+ |

New Analyze your query with SmartBLAST

Graphic Summary

Distribution of the top 7 Blast Hits on 7 subject sequences

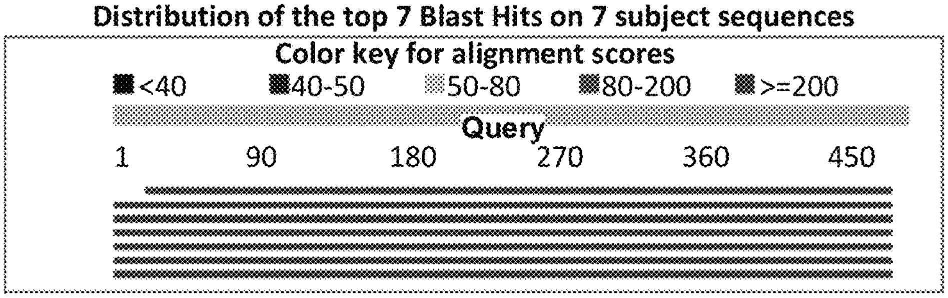

FIG. 12B

Sequences producing significant alignments:

| Description | Max score | Total score | Query cover | E value | Ident | Accession |
|---|---|---|---|---|---|---|
| Unnamed protein product (Coffea canephora) | 730 | 730 | 95% | 0.0 | 76% | CDP08231.1 |
| PREDICTED: vacuolar-processing enzyme-like [Daucus carota subsp. sativus] | 708 | 708 | 100% | 0.0 | 70% | XP_017229093.1 |
| Peptidase C13, legumain [Corchorus capsularis] | 707 | 707 | 100% | 0.0 | 70% | OMO66906.1 |
| Peptidase C13, legumain [Corchorus olitorius] | 702 | 702 | 100% | 0.0 | 69% | OMO86616.1 |
| vacuolar-processing enzyme [Jatropha curcas] | 701 | 701 | 100% | 0.0 | 68% | XP_012077326.1 |
| vacuolar processing enzyme [Malus hupehensis] | 699 | 699 | 100% | 0.0 | 69% | AGC94758.1 |
| PREDICTED: vacuolar-processing enzyme-like (Pyrus x bretschneiden] | 698 | 698 | 100% | 0.0 | 69% | XP_009361606.1 |

*FIG. 14A*
One Step Homodimerization
Scaffold based dimerization strategy
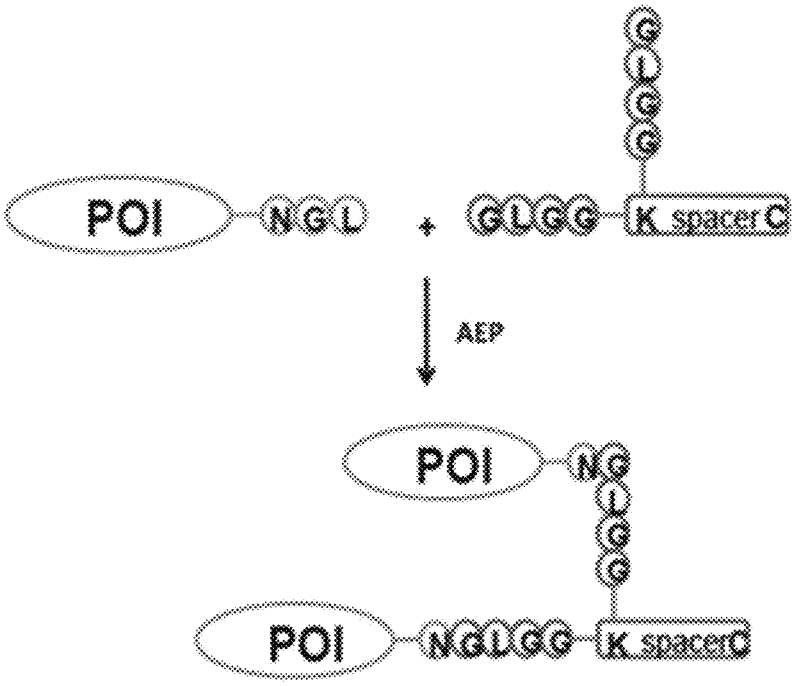
Ub-AA-NGL+2-mer linker Ub (50 uM), AEP 0.5 uM, 1 h
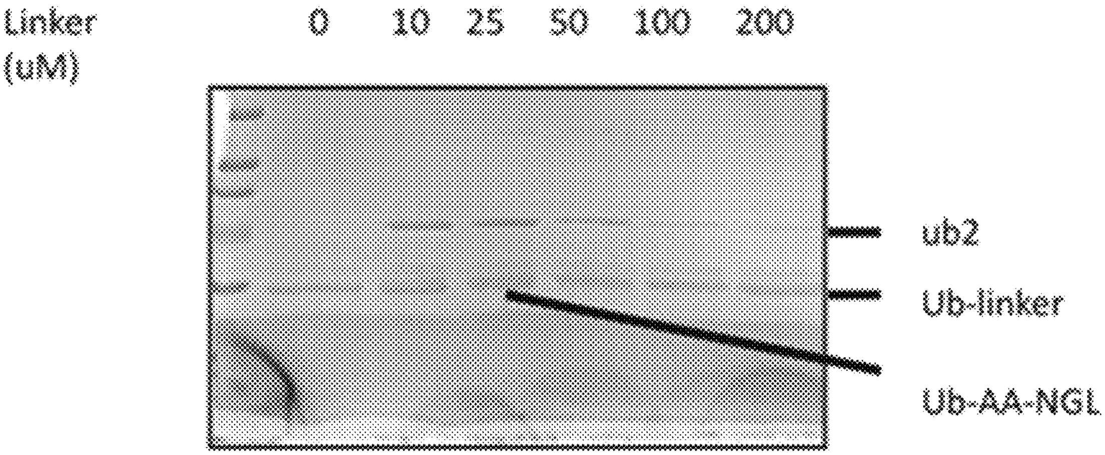

Two-step, heterodimerization strategy

Schematic Illustration of protein ultra-oligomer strategy

M = Molecular weight
1 = SNAP-NGL protein control
2 = SNAP-NGL added to RAW cells, no ligase, cells after wash
3 = SNAP-NGL added to RAW cells, with ligase, wash solution
4 = SNAP-NGL added to RAW cells, with ligase, cells after wash
5 = same as 2, using HEK cells
6 = same as 3, using HEK cells
7 = same as 4, using HEK cells

SEQUENCE LISTING

```
Sequence total quantity: 19
SEQ ID NO: 1            moltype = AA  length = 474
FEATURE                 Location/Qualifiers
source                  1..474
                        mol_type = protein
                        organism = Ovaloparmena affinis
SEQUENCE: 1
MVRYLAGAVL LLVVLSVAAA VSGARDGDYL HLPSEVSRFF RPQETNDDHG EDSVGTRWAV  60
LIAGSKGYAN YRHQAGVCHA YQILKRGGLK DENIVVFMYD DIAYNESNPR PGVIINSPHG  120
SDVYAGVPKD YTGEEVNAKN FLAAILGNKS AITGGSGKVV DSGPNDHIFI YYTDHGAAGV  180
IGMPSKPYLY ADELNDALKK KHASGTYKSL VFYLEACESG SMFEGILPED LNIYALTSTN  240
TTESSWAYYC PAQENPPPPE YNVCLGDLFS VAWLEDSDVQ NSWYETLNQQ YHHVDKRISH  300
ASHATQYGNL KLGEEGLFVY MGSNPANDNY TSLDGNALTP SSIVVNQRDA DLLHLWEKFR  360
KAPEGSARKE EAQTQIFKAM SHRVHIDSSI KLIGKLLFGI EKCTEILNAV RPAGQPLVDD  420
WACLRSLVGT FETHCGSLSE YGMRHTRTIA NICNAGISEE QMAEAASQAC ASIP        474

SEQ ID NO: 2            moltype = AA  length = 18
FEATURE                 Location/Qualifiers
source                  1..18
                        mol_type = protein
                        organism = Ovaloparmena affinis
VARIANT                 1
                        note = X  corresponds to position 247 of SEQ ID NO:1 and is
                         G, A, S, or C.
VARIANT                 2
                        note = X  is any amino acid, preferably any amino acid that
                         does not disrupt the structural fold of the remaining
                         conserved amino acids
VARIANT                 6
                        note = X  is any amino acid, preferably any amino acid that
                         does not disrupt the structural fold of the remaining
                         conserved amino acids
VARIANT                 7
                        note = X  is any amino acid, preferably any amino acid that
                         does not disrupt the structural fold of the remaining
                         conserved amino acids
VARIANT                 8
                        note = X  is any amino acid, preferably any amino acid that
                         does not disrupt the structural fold of the remaining
                         conserved amino acids
VARIANT                 9
                        note = X  is any amino acid, preferably any amino acid that
                         does not disrupt the structural fold of the remaining
                         conserved amino acids
VARIANT                 10
                        note = X  is any amino acid, preferably any amino acid that
                         does not disrupt the structural fold of the remaining
                         conserved amino acids
VARIANT                 16
                        note = X  is any amino acid, preferably any amino acid that
                         does not disrupt the structural fold of the remaining
                         conserved amino acids
VARIANT                 17
                        note = X  corresponds to position 263 of SEQ ID NO:1 and is
                         any amino acid, preferably any amino acid that does not
                         disrupt the structural fold of the remaining conserved
```

```
                         amino acids
SEQUENCE: 2
XXYCPXXXXX PPPEYXXC                                               18

SEQ ID NO: 3            moltype = AA  length = 474
FEATURE                 Location/Qualifiers
source                  1..474
                        mol_type = protein
                        organism = Ovaloparmena affinis
SEQUENCE: 3
MVRYLAGAVL LLVVLSVAAA VSGARDGDYL HLPSEVSRFF RPQETNDDHG EDSVGTRWAV  60
LIAGSKGYAN YRHQAGVCHA YQILKRGGLK DENIVVFMYD DIAYNESNPR PGVIINSPHG  120
SDVYAGVPKD YTGEEVNAKN FLAAILGNKS AITGGSGKVV DSGPNDHIFI YYTDHGAAGV  180
IGMPSKPYLY ADELNDALKK KHASGTYKSL VFYLEACESG SMFEGILPED LNIYALTSTN  240
TTESSWCYYC PAQENPPPPE YNVCLGDLFS VAWLEDSDVQ NSWYETLNQQ YHHVDKRISH  300
ASHATQYGNL KLGEEGLFVY MGSNPANDNY TSLDGNALTP SSIVVNQRDA DLLHLWEKFR  360
KAPEGSARKE EAQTQIFKAM SHRVHIDSSI KLIGKLLFGI EKCTEILNAV RPAGQPLVDD  420
WACLRSLVGT FETHCGSLSE YGMRHTRTIA NICNAGISEE QMAEAASQAC ASIP        474

SEQ ID NO: 4            moltype = AA  length = 462
FEATURE                 Location/Qualifiers
source                  1..462
                        mol_type = protein
                        organism = Clitoria ternatea
SEQUENCE: 4
IRDDFLRLPS QASKFFQADD NVEGTRWAVL VAGSKGYVNY RHQADVCHAY QILKKGGLKD  60
ENIIVFMYDD IAYNESNPHP GVIINHPYGS DVYKGVPKDY VGEDINPPNF YAVLLANKSA  120
LTGTGSGKVL DSGPNDHVFI YYTDHGGAGV LGMPSKPYIA ASDLNDVLKK KHASGTYKSI  180
VFYVESCESG SMFDGLLPED HNIYVMGASD TGESSWVTYC PLQHPSPPPE YDVCVGDLFS  240
VAWLEDCDVH NLQTETFQQQ YEVVKNKTIV ALIEDGTHVV QYGDVGLSKQ TLFVYMGTDP  300
ANDNNTFTDK NSLGTPRKAV SQRDADLIHY WEKYRRAPEG SSRKAEAKKQ LREVMAHRMH  360
IDNSVKHIGK LLFGIEKGHK MLNNVRPAGL PVVDDWDCFK TLIRTFETHC GSLSEYGMKH  420
MRSFANLCNA GIRKEQMAEA SAQACVSIPD NPWSSLHAGF SV                    462

SEQ ID NO: 5            moltype = AA  length = 488
FEATURE                 Location/Qualifiers
source                  1..488
                        mol_type = protein
                        organism = Coffea canephora
SEQUENCE: 5
MMRYATAALL LLALSIIAVA EARDNFLKLP SEIADFFHPK ERSDAGGDSV GTRWAVLIAG  60
SNGYWNYRHQ ADVCHAYQIL KRGGLKDENI VVFMYDDIAY NEENPRPGVI INSPHGADVY  120
QGVPKDYTGD DVNAKNFLAA ILGDKTAITG GSGKVVDSGP NDHIFIYYTD HGGPGVLGTP  180
SGPYLYADDL NEVLKKKHAS GTYKSLVFYL EACESGSIFE GLLPEDLNIY ATTASNAEES  240
SWGTYCPGEY PSPPPEYETC LGDLYSVAWM EDSEIHNLHT ETLKQQYHLV KKRTSSSNSA  300
YGSHVMQYGD LKLSLEDLFL YMGTNPANDN YTFVDENSLR PSSKAVNQRD ADLLHFWDKF  360
RKAPEGSARK VEAQKQVVEA MSHRMHIDNS VKLIGKLLFG IEKGSEILNS VRPAGHPLAD  420
DWDCLKSLVR TFETHCGSLS QYGMKHMRSI ANICNAGIKK DQMAEAAAQA CVSLPSNSWS  480
SLHRGFSA                                                          488

SEQ ID NO: 6            moltype = AA  length = 491
FEATURE                 Location/Qualifiers
source                  1..491
                        mol_type = protein
                        organism = Daucus carota subsp. sativus
SEQUENCE: 6
MVRYLAGAVA LLVVVSISAV VESRRDIVGD VLKLPSEVSS FFRPVAEEED SVGTRWAVLI  60
AGSNGYWNYR HQADICHAYQ LLRRGGVKEE NIVVFMYDDI AYDEENPRPG VIINSPHGSD  120
VYKGVPKDYT GEDVTVNNVF AAILGDKSAT TGGSGKVVDS GPNDHIFIYY SDHGGPGVLG  180
MPTNPYMYAG DLVDVLKKKH ASGTYKSMVF YLEACESGSI FEGLLPEGLN IYATTASNAY  240
ESSWGTYCPG EYPSPPPEYE TCLGDLYSVA WMEDSDIHNL RTETLRQQYQ QVKKRTSNDN  300
SGWGSHVMQY GDLKLSTEEL FMYMGTNPAN DNFTFVDDNS LRLSSSKAVN QRDADLLHFW  360
DKYRKAPEGS DRKIAAQKQF SEAMSHRMHL DNSIQLIGKL LFGIDTASEV LTTVRPSGQP  420
LVDDWLCLKK LVRTFETYCG SLSQYGMKHM RSIANICNAG ISEEQMSEAS AQACVTFPSN  480
PWSSVNKGFT A                                                      491

SEQ ID NO: 7            moltype = AA  length = 486
FEATURE                 Location/Qualifiers
source                  1..486
                        mol_type = protein
                        organism = Corchorus capsularis
SEQUENCE: 7
MTRLVAGVIL LLLSVTGIVS AGRDATGDVL RLPSEASRFF RPSDDDEVGT RWAVLIAGSN  60
GYWNYRHQAD VCHAYQLLKK GGLKDENIIV FMYDDIAYNY ENPRQGIIIN SPHGDDVYQG  120
VPKDYTGEEV TVHNFLAAIL GNKTAITGGS GKVVDSGPND HIFIYYTDHG GPGVLGMPTY  180
PYLYADELID TLKKKHASGT YKSLVFYLEA CESGSIFEGL LPEGLNIYAT TASNADESSW  240
GTYCPGEYPS PPPEYETCLG DLYSVAWMED SDLHNLRTET LHQQYELVKR RTLNGNSAYG  300
SHVMQYGDVG LAKEHLFLYL GTNPANDNFT FIDENSLQPP AKAVNQRDAD LVHFWDKYRK  360
APDGSARKVE AQKQVVEAMS HRMHVDNSIQ LIGKLLFGIE RGADVLKTVR PAGQPLVDDW  420
```

-continued

```
KCLKSMVRTF ETHCGSLAQY GMKHMRSIAN ICNAGIQTEQ IAEASAQACV SIPSGQWSSI  480
QKGFSA                                                              486

SEQ ID NO: 8           moltype = AA  length = 486
FEATURE                Location/Qualifiers
source                 1..486
                       mol_type = protein
                       organism = Corchorus olitorius
SEQUENCE: 8
MTRLVAGVIL LLLSVTGIAS AGRDATGDVL RLPSEASRFF RPSDDDEVGT RWAVLIAGSN  60
GYWNYRHQAD VCHAYQLLKK GGLKDENIIV FMYDDIAFNY ENPRQGIIIN SPHGDDVYQD  120
VPKDYTGEEV TVHNFLAAIL GNKTAIKGGS GKVVDSGPND HIFIYYTDHG GPGVLGMPTY  180
PYLYADELID TLKKKHASGT YKSLVFYLEA CESGSIFEGL LPEGLNIYAT TASNADESSW  240
GTYCPGEYPS PPPEYETCLG DLYSVAWMED SDLHNLRTET LHQQYELVKR RTLNGNSAYG  300
SHVMQYGDVG LAKEHLFLYL GTNPANDNFT FIDENSLQPP AKAVNQRDAD LVHFWDKYRK  360
APDGSVRKVE AQKQVVEAMS HRMHVDNSIQ LIGKLLFGIE RGADVLKTVR PAGQPLVDDW  420
KCLKSMVRTF ETHCGSLAQY GMKHMRSIAN ICNAGIQTEQ MAEASSQACV SIPSGQWSSI  480
QKGFSA                                                              486

SEQ ID NO: 9           moltype = AA  length = 493
FEATURE                Location/Qualifiers
source                 1..493
                       mol_type = protein
                       organism = Jatropha curcas
SEQUENCE: 9
MTRLATGVIL LLLALCVVSS AGSRDIVGDV LRLPSEASRF FRPGGAHVAK EDDSTGTRWA  60
ILIAGSNGYW NYRHQADVCH AYQLLKKGGL KDENIIVFMY DDIAFNKENP RPGVIINNPY  120
GEDVYKGVPK DYTGEDVNVN NFFAAILGNK TAITGGSGKV VDSGPNDHIF IYYTDHGGPG  180
VLGMPTNPYL YANDLIDVLI KKHASGTYKS LVFYLEACES GSIFEGLLPE GLNIYATTAA  240
NAEESSWGTY CPGEYPSPPP EYETCLGDLY SVAWMEDSDV HNLQTETLRQ QYQLVKRRTA  300
NGNSAYGSHV MQYGDVGLSK DNLFLYMGTN PANENYTFVD ENSLRPPSKA VNQRDADLVH  360
FWDKYRKAPD GSTRKIQAQK QFVEAMSHRM HLDHSMKLIG KLLFGIGKGS EVLNAIRPAG  420
QPLVDDWVCL KTLVRTFETH CGSLSQYGMK HMRSLANLCN AGIREDQMAE ASAQACVSIP  480
SGPWSSLHKG FSA                                                      493

SEQ ID NO: 10          moltype = AA  length = 494
FEATURE                Location/Qualifiers
source                 1..494
                       mol_type = protein
                       organism = Malus hupehensis
SEQUENCE: 10
MTRLASAVVL LFLASVLASA AGSRDLIGDV LRLPSEASRF FGRGDDAPDQ QDDGTVGTRW  60
AVLIAGSNGY WNYRHQADIC HAYQLLKKGG LKDENIVVFM YDDIAYNEEN PRQGVIINSP  120
HGSDVYEGVP KDYTGEDVTV NNFFAAILGN KTALTGGSGK VVDSGPNDHI FIYYTDHGGP  180
GILGMPTSPY IYANDLIEVL KKKHAAGTYR SLVFYLEACE SGSIFEGLLP EGLNIFATTA  240
SNAEESSWGT YCPGEYPSPP PEYDTCLGDL YSVAWMEDSD VHNLRSETLH QQYELVKTRA  300
ANDNSGSGSH VMQYGDVGLS KNNLFVYMGT NPANDNYTFL GENSLRPSSK AVNQRDADLL  360
HFWHKYRKAP EGSARKIQAQ KDFVEAMSHR MHIDQTMKLI GKLLFGIEKG PQVLNAVRPA  420
GQPLVDDWDC LKTMVRSFET HCGSLSQYGM KHMRSLANIC NAGMTQEQMA EASAQACVSA  480
PSGRWSSLHR GFSA                                                     494

SEQ ID NO: 11          moltype = AA  length = 494
FEATURE                Location/Qualifiers
source                 1..494
                       mol_type = protein
                       organism = Pyrus x bretschneideri
SEQUENCE: 11
MTRFAGAVVL LFLASVLASA AGSRDLIGDV LRLPSEASRF FGRGDDAPDQ QDDGTVGTRW  60
AVLIAGSNGY WNYRHQADIC HAYQLLKKGG LKDENIVVFM YDDIAYNEEN PRQGVIINNP  120
QGSDVYEGVP KDYTGEDVTV NNFFAAILGN KTALTGGSGK VVDSGPNDHI FIYYTDHGGP  180
GVLGMPTSPY IYANDLIEVL KKKHAAGTYK SLVFYLEACE SGSIFEGLLP EGLNIFATTA  240
SNAEESSWGT YCPGEYPSPP PEYETCLGDL YSVAWMEDSD IHNLRSETLH QQYELVKTRT  300
ANDNYGFGSH VMQYGDVGLS KNNLFVYMGT NPANDNYTFL GENSLRPSSK AVNQRDADLL  360
HFWHKYRKAP EGSARKVQAQ KDFVEAMSHR MHIDQTMKLI GKLLFGIEKG PQVLNAVRPA  420
GQPLVDDWDC LKTMVRSFET HCGSLSQYGM KHMRSLANIC NAGMTQEQMA EASAQACVSA  480
PSSRWSSLHR GFSA                                                     494

SEQ ID NO: 12          moltype = AA  length = 537
FEATURE                Location/Qualifiers
source                 1..537
                       mol_type = protein
                       organism = synthetic construct
SEQUENCE: 12
MGMAHHHHHH MQIFVKTLTG KTITLEVEPS DTIENVKAKI QDKEGIPPDQ QRLIFAGKQL  60
EDGRTLSDYN IQKESTLHLV LRLRGGARDG DYLHLPSEVS RFFRPQETND DHGEDSVGTR  120
WAVLIAGSKG YANYRHQAGV CHAYQILKRG GLKDENIVVF MYDDIAYNES NPRPGVIINS  180
PHGSDVYAGV PKDYTGEEVN AKNFLAAILG NKSAITGGSG KVVDSGPNDH IFIYYTDHGA  240
AGVIGMPSKP YLYADELNDA LKKKHASGTY KSLVFYLEAC ESGSMFEGIL PEDLNIYALT  300
STNTTESSWC YYCPAQENPP PPEYNVCLGD LFSVAWLEDS DVQNSWYETL NQQYHHVDKR  360
```

```
ISHASHATQY GNLKLGEEGL FVYMGSNPAN DNYTSLDGNA LTPSSIVVNQ RDADLLHLWE  420
KFRKAPEGSA RKEEAQTQIF KAMSHRVHID SSIKLIGKLL FGIEKCTEIL NAVRPAGQPL  480
VDDWACLRSL VGTFETHCGS LSEYGMRHTR TIANICNAGI SEEQMAEAAS QACASIP     537

SEQ ID NO: 13          moltype = AA  length = 10
FEATURE                Location/Qualifiers
source                 1..10
                       mol_type = protein
                       organism = synthetic construct
SEQUENCE: 13
MGMAHHHHHH                                                         10

SEQ ID NO: 14          moltype = AA  length = 76
FEATURE                Location/Qualifiers
source                 1..76
                       mol_type = protein
                       organism = synthetic construct
SEQUENCE: 14
MQIFVKTLTG KTITLEVEPS DTIENVKAKI QDKEGIPPDQ QRLIFAGKQL EDGRTLSDYN  60
IQKESTLHLV LRLRGG                                                  76

SEQ ID NO: 15          moltype = AA  length = 450
FEATURE                Location/Qualifiers
source                 1..450
                       mol_type = protein
                       organism = Ovaloparmena affinis
SEQUENCE: 15
ARGDYLHLPS EVSRFFRPQE TNDDHGEDSV GTRWAVLIAG SKGYANYRHQ AGVCHAYQIL  60
KRGGLKDENI VVFMYDDIAY NESNPRPGVI INSPHGSDVY AGVPKDYTGE EVNAKNFLAA  120
ILGNKSAITG GSGKVVDSGP NDHIFIYYTD HGAAGVIGMP SKPYLYADEL NDALKKKHAS  180
GTYKSLVFYL EACESGSMFE GILPEDLNIY ALTSTNTTES SWCYYCPAQE NPPPPEYNVC  240
LGDLFSVAWL EDSDVQNSWY ETLNQQYHHV DKRISHASHA TQYGNLKLGE EGLFVYMGSN  300
PANDNYTSLD GNALTPSSIV VNQRDADLLH LWEKFRKAPE GSARKEEAQT QIFKAMSHRV  360
HIDSSIKLIG KLLFGIEKCT EILNAVRPAG QPLVDDWACL RSLVGTFETH CGSLSEYGMR  420
HTRTIANICN AGISEEQMAE AASQACASIP                                   450

SEQ ID NO: 16          moltype = DNA  length = 38
FEATURE                Location/Qualifiers
source                 1..38
                       mol_type = other DNA
                       note = primer used for mutagenesis
                       organism = synthetic construct
SEQUENCE: 16
caccaccgaa agcagctggg cctactattg cccggcgc                          38

SEQ ID NO: 17          moltype = AA  length = 14
FEATURE                Location/Qualifiers
source                 1..14
                       mol_type = protein
                       note = Peptide template used for characterizing recognition
                        sequence specificity of Quicklase
                       organism = synthetic construct
VARIANT                1
                       note = X  is any amino acid. In each screen, only one of
                        the residue is modified. The default amino acid at X1
                        position is G, at X2 position is L, and at X3 position is
                        G, and at the X4 position is L, in this screen.
VARIANT                2
                       note = X  is any amino acid. In each screen, only one of
                        the residue is modified. The default amino acid at X1
                        position is G, at X2 position is L, and at X3 position is
                        G, and at the X4 position is L, in this screen.
VARIANT                13
                       note = X  is any amino acid. In each screen, only one of
                        the residue is modified. The default amino acid at X1
                        position is G, at X2 position is L, and at X3 position is
                        G, and at the X4 position is L, in this screen.
VARIANT                14
                       note = X  is any amino acid. In each screen, only one of
                        the residue is modified. The default amino acid at X1
                        position is G, at X2 position is L, and at X3 position is
                        G, and at the X4 position is L, in this screen.
SEQUENCE: 17
XXYRRGRLYR RNXX                                                    14

SEQ ID NO: 18          moltype = AA  length = 15
FEATURE                Location/Qualifiers
source                 1..15
                       mol_type = protein
```

-continued

```
                        organism = synthetic construct
SEQUENCE: 18
GLPVSTKPVA TRNGL                                                    15

SEQ ID NO: 19           moltype = AA  length = 15
FEATURE                 Location/Qualifiers
source                  1..15
                        mol_type = protein
                        organism = synthetic construct
SEQUENCE: 19
GLPVSTKPVA TRNHV                                                    15
```

METHODS FOR ENZYMATIC PEPTIDE LIGATION

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690148_552C1_SEQUENCE LISTING.XML. The text file is 30.202 bytes, was created on Sep. 28, 2022, and is being submitted electronically via Patent Center.

CROSS-REFERENCE TO RELATED APPLICATION

This application makes reference to and claims the benefit of priority of the Singapore Patent Application No. 10201607951V filed on 23 Sep. 2016, the content of which is incorporated herein by reference for all purposes, including an incorporation of any element or part of the description, claims or drawings not contained herein and referred to in Rule 20.5(a) of the PCT, pursuant to Rule 4.18 of the PCT.

FIELD OF THE INVENTION

The present invention relates generally to Asx-specific peptide ligases, methods of enzymatically ligating peptides using said ligases and the thus generated peptides and peptide-containing complexes.

BACKGROUND OF THE INVENTION

Unlike proteases that are abundantly found in nature, peptide ligases are relatively rare. The first asparagine/aspartate (Asx) peptide ligase reported was butelase 1, purified from the cyclotide-producing plant *Clitoria ternatea* (Nguyen, G. K., et al., Nat Chem Biol, 2014. 10(9): p. 732-8). Compared to bacterial sortase which is commonly used to catalyze transpeptidation reactions in vitro, butelase 1 shows exceptionally high efficiency in catalyzing both peptide and protein ligation reactions, opening a wide range of applications in biotechnology, protein engineering, chemoenzymatic synthesis and protein labeling. Recently an asparaginyl endopeptidase (AEP) evolutionary related to butelase 1 named OaAEP1b, also having the ability to link the N- and C-termini of peptidyl substrates, was isolated from the plant *Oldenlandia affinis* and expressed using *E. coli* in an active form following activation at acidic pH. Both butelase 1 and OaAEP1b use the amino acid(s) Asx at the ligation site and have 65% amino-acid sequence identity. However, the reported catalytic efficiency of OaAEP1b is markedly lower than butelase 1 (Harris, K. S., et al., Nat Commun, 2015. 6: p. 10199). In addition, the structural and catalytic mechanisms underlying this family of protein ligases were poorly understood. Therefore, there is still need in the art for new developments that overcome the drawbacks of existing techniques, in particular new methods that allow efficient peptide ligation.

SUMMARY OF THE INVENTION

The present invention satisfies the aforementioned need in the art by providing the methods described herein.

In a first aspect, the present invention relates to a method of generating a peptide of Formula (I)

$$P^1\text{-Asx-Xaa}^1\text{-Xaa}^2\text{-}P^2 \quad \text{(I),}$$

by ligating a first peptide of Formula (II)

$$P^1\text{-Asx-Xaa}^3\text{-Leu-COOH/CONH}_2 \quad \text{(II)}$$

to a second peptide of Formula (III)

$$H_2N\text{-Xaa}^1\text{-Xaa}^2\text{-}P^2 \quad \text{(III),}$$

wherein $P^1$ and $P^2$ are each independently any peptide, modified or unmodified, and optionally can combine such that the peptides of formula (II) and (III) are the termini of the same peptide; Asx is Asp or Asn; $Xaa^1$ is any naturally occurring amino acid; $Xaa^2$ is any naturally occurring amino acid with the exception of Pro, preferably Leu or Ile; and $Xaa^3$ is any naturally occurring amino acid, preferably selected from the group consisting of His, Ala, Ser, Cys, Asn, Gly, Arg, Met, Lys, Gln, Leu, and Glu, by enzymatically cleaving the bond between “Asx” and “$Xaa^3$” in the first peptide of Formula (II) and ligating the fragment $P^1$-Asx of the first peptide via its C-terminus to the N-terminus of the second peptide of Formula (III) to form a ligated peptide of Formula (I), wherein the enzymatic cleavage and ligation reaction is catalyzed by a peptide ligase having the activity of OaAEP1 Cys247Ala (SEQ ID NO:1, also termed “Quicklase” hereinafter) under conditions suitable for said cleavage and ligation reaction.

In various embodiments, the first and second peptides are the termini of the same peptide (i.e., $P^1$ and $P^2$ combine to form a single core peptide sequence) such that the method cyclizes said peptide.

In various embodiments, the peptide ligase having the activity of OaAEP1 Cys247Ala (SEQ ID NO:1) comprises or consists of:

(a) the amino acid sequence set forth in SEQ ID NO:1;

(b) an amino acid sequence that shares at least 65%, preferably at least 75%, even more preferably at least 85%, most preferably at least 95% sequence identity with, or at least 80%, preferably at least 90%, more preferably at least 95% sequence homology with the amino acid sequence as set forth in SEQ ID NO:1, provided that said peptide ligase comprises the amino acid sequence set forth in SEQ ID NO:2 at the positions corresponding to residues 247-264 of SEQ ID NO:1;

(c) a functional fragment of (a) or (b); or (d) an amino acid sequence containing either (a) or (b) or (c) as its essential component, with the proviso that said peptide ligase is not the wild-type OaAEP1 having the amino acid sequence set forth in SEQ ID NO:3 or butelase 1 having the amino acid sequence set forth in SEQ ID NO:4.

In various embodiments, the peptide ligase having the activity of OaAEP1 Cys247Ala (SEQ ID NO:1) comprises or consists of:

(a) the amino acid sequence set forth in SEQ ID NO:1;
(b) the amino acid sequence set forth in SEQ ID NO:5;
(c) the amino acid sequence set forth in SEQ ID NO:6;
(d) the amino acid sequence set forth in SEQ ID NO:7;
(e) the amino acid sequence set forth in SEQ ID NO:8;
(f) the amino acid sequence set forth in SEQ ID NO:9;
(g) the amino acid sequence set forth in SEQ ID NO:10; or
(h) the amino acid sequence set forth in SEQ ID NO:11.

In various embodiments, the first and/or second peptide further comprises a labeling moiety.

In various embodiments, the labeling moiety is an affinity tag, therapeutic agent, detectable label, or scaffold molecule.

In various embodiments, the first and/or second peptide may be coupled to a solid support material.

In various embodiments, the first and/or second peptide is a cellular surface protein such that the method results in the modification or tagging of the cellular surface protein and in result the cellular surface as such.

In a second aspect, the present invention relates to a method of preparing a dimer, oligomer, or multimer of one or more peptides of interest, the method comprising the steps of:

(a) providing one or more peptides of interest having C-terminal Asx-$Xaa^3$-Leu-COOH/$CONH_2$ residues and a scaffold molecule having two or more copies of N-terminal $H_2N$-$Xaa^1$-$Xaa^2$ residues or, alternatively, providing one or more peptides of interest having N-terminal $H_2N$-$Xaa^1$-$Xaa^2$ residues and a scaffold molecule having two or more copies of C-terminal Asx-$Xaa^3$-Leu-COOH/$CONH_2$ residues, wherein Asx is Asp or Asn; $Xaa^1$ is any naturally occurring amino acid; $Xaa^2$ is any naturally occurring amino acid with the exception of Pro, preferably Leu or Ile; and $Xaa^3$ is any naturally occurring amino acid, preferably selected from the group consisting of His, Ala, Ser, Cys, Asn, Gly, Arg, Met, Lys, Gln, Leu, and Glu;

(b) providing a peptide ligase having the activity of OaAEP1 Cys247Ala (SEQ ID NO:1);

(c) preparing a mixture of the one or more peptides of interest, the scaffold molecule, and the peptide ligase having the activity of OaAEP1 Cys247Ala (SEQ ID NO:1);

(d) subjecting the mixture to conditions that allow the peptide ligase having the activity of OaAEP1 Cys247Ala (SEQ ID NO:1) to catalyze the ligation of the one or more peptides of interest to the scaffold molecule.

In a third aspect, the present invention relates to a method of modifying or tagging the surface of a target cell by one or more peptides of interest, the method comprising the steps of:

(a) providing the one or more peptides of interest having C-terminal Asx-$Xaa^3$-Leu-COOH/$CONH_2$ residues and/or having N-terminal $H_2N$-$Xaa^1$-$Xaa^2$ residues, wherein Asx is Asp or Asn; $Xaa^1$ is any naturally occurring amino acid; $Xaa^2$ is any naturally occurring amino acid with the exception of Pro, preferably Leu or Ile; and $Xaa^3$ is any naturally occurring amino acid, preferably selected from the group consisting of His, Ala, Ser, Cys, Asn, Gly, Arg, Met, Lys, Gln, Leu, and Glu;

(b) providing a peptide ligase having the activity of OaAEP1 Cys247Ala (SEQ ID NO:1);

(c) contacting the target cell with the one or more peptides of interest and the peptide ligase having the activity of OaAEP1 Cys247Ala (SEQ ID NO:1);

(d) subjecting the target cell to conditions that allow the peptide ligase having the activity of OaAEP1 Cys247Ala (SEQ ID NO:1) to catalyze the ligation of the one or more peptides of interest to a cellular surface protein of the target cell.

In various embodiments, the method further comprises removing the unligated one or more peptides from the target cell after step (d).

In various embodiments, the one or more peptides of interest comprise a labeling moiety, as already described above.

In various embodiments, the target cell recombinantly expresses a surface polypeptide having N-terminal $H_2N$-$Xaa^1$-$Xaa^2$ residues or C-terminal Asx-$Xaa^3$-Leu-COOH residues for ease of tagging by the peptide of interest.

In various embodiments of all afore-described aspects of the invention, (a) Asx is Asn or Asp; and/or (b) $Xaa^1$ is all naturally occurring amino acids; and/or (c) $Xaa^2$ is Leu or Ile; and/or (d) $Xaa^3$ is selected from the group consisting of His, Ala, Ser, Cys, Asn, Gly, Arg, Met, Lys, Gln, Leu, and Glu.

In preferred embodiments, two or more of features (a)-(d) are met, i.e., (a) and (b), (a) and (c), (a) and (d), (b) and (c), (b) and (d), or three or more features are met, i.e., (a), (b) and (c), (a), (b) and (d), (a), (c) and (d), (b), (c) and (d) or, most preferably all four are met.

In preferred embodiments, Asx is Asn, $Xaa^1$ is any naturally occurring amino acid, $Xaa^2$ is Leu, and $Xaa^3$ is His, Ser, Cys, Gly or Ala.

In more preferred embodiments, Asx is Asn, $Xaa^1$ is Arg or Gly, $Xaa^2$ is Leu, and $Xaa^3$ is His, Ala or Gly.

In a fourth aspect, the invention relates to the ligated peptides and/or tagged target cells obtainable according to any of the methods of the invention.

In a fifth aspect, the invention relates to the peptide ligase OaAEP1 Cys247Ala having the amino acid sequence of SEQ ID NO:1 and other peptide ligases having the activity thereof, as described above, as well as kits comprising any of said peptide ligases, in particular OaAEP1 Cys247Ala (SEQ ID NO:1).

In still another aspect, the present invention relates to the use of a peptide ligase having the activity of OaAEP1 Cys247Ala (SEQ ID NO:1) for the ligation of two peptides, as described herein.

It is understood that all embodiments disclosed herein in relation to one aspect of the invention, are similarly applicable to all other aspects of the invention.

BRIEF DESCRIPTION OF THE DRAWINGS

The invention will be better understood with reference to the detailed description when considered in conjunction with the non-limiting examples and the accompanying drawings.

FIGS. 2A-2E show purification and activation of OaAEP1b. FIG. 2A shows a schematic illustration of the His-Ub-OaAEP1 construct used with the boundaries of the three regions of the protein indicated and the deduced activation segment. 6-His tag and Ubiquitin tag followed by OaAEP1 (24-474) was synthesized and inserted into pET28b vector. After Ni-NTA affinity purification, about half of Ub-AEP-FL lost the N-terminal fusion tags and was purified in AEP-FL form (53-474), which was eventually crystallized. The enzymatic active form of OaAEP1b, AEP-holo (53-347/351) is the acidic induced self-cleavage product of AEP-FL, which lost the C-terminal auto inhibitory cap domain. FIG. 2B shows SDS PAGE analysis of fractions obtained over the course of chromatographic purification and of dissolved crystals. FIG. 2C shows size-exclusion chromatography profiles of OaAEP1 before and after activation showing Ub-AEP-FL and AEP-FL heterodimer and the AEP-holo monomer. The elution volumes of standard proteins are indicated for comparison. FIG. 2D shows SDS PAGE analysis of OaAEP1 pH-dependent activation. The activation was performed for 3 hours, and the peak of activation is in between pH 3.4 to 4. FIG. 2E shows trans activation/maturation of the inactive Cys217Ser active site mutant by the active recombinant mature OaAEP1 enzyme. The active site Cys217Ala mutant is devoid of self-activation activity. Addition of 5% AEP-FL wt enable trans-cleavage and activation of most of the AEP-FL Cys217Ala after 18 hours incubation at pH 3.7.

FIGS. 3A-3F show a crystal structure of OaAEP1 in its zymogenic form. FIG. 3A shows an overall "front" view of the OaAEP1 structure represented as "cartoon" (with α-helices as ribbons and β-strands as arrows) with the catalytic core domain colored in green, the pro-domain in purple. The flexible linker spanning residues 325-343 (not visible) is depicted as dashed line and residues 344-347 that are trapped in the OaAEP1 active site are depicted as sticks. The molecular surface views in the panels of FIG. 3B and FIG. 3C were obtained by separating the core domain from the cap domain and rotating by an angle of 90° in opposite directions respectively (indicated by arrows). FIG. 3D shows the OaAEP1 inactive dimer is stabilized via intermolecular interactions provided by the cap region. Residues 344-347 that are bound in the active site are depicted as sticks and labeled. Compared to human legumain, these linker residues are bound at the catalytic center in an orientation similar to peptide based legumain inhibitors. From this comparative view, the putative channel that accommodates the incoming amine could be identified on the core domain surface. The orientation of an incoming substrate poised to undergo the ligation reaction is indicated by an arrow along the channel at the protein surface (see text). FIG. 3E shows the hlegum molecular surface is shown in the same orientation as OaAEP1 with the peptide Ac-Tyr-Val-Ala-Asp-CMK (sticks) covalently bound to the active site Cys189 (from PDB code: 4AWA). Here, the incoming amine channel is completely blocked, explaining the lack of significant ligase activity. FIG. 3F shows a cartoon highlight the two critical structural features related to the substrates binding and catalytic activities of OaAEP1 Cys247Ala. P1 binding site is responsible for efficient cleavage, and P2 binding site is related to efficient protein ligation.

FIGS. 4A-4D show the OaAEP1 active-site and the activation segment. FIG. 4A shows a close-up view of the OaAEP1 active site with active site residues discussed in the text displayed as sticks and labeled: The canonical AEP catalytic pair His175 and Cys217 and the linker residues 344-347 bound at the catalytic center are depicted as sticks. Also shown the disulfide bond formed by Cys250 and Cys264 (conserved in butelase 1), which forms an open amine incoming channel and the "gate-keeper" Cys247 a major determinant for the ligase activity. Hydrogen bonds formed by P1 residue Gln347 which is bound in the S1 pocket are depicted by dashed lines and interatomic distances are displayed in Å. The panel in FIG. 4B displays an electron density map with the segment 344-347 of the polypeptide omitted from the phase calculation and contoured at 3σ level. FIG. 4C shows residual activation of OaAEP1 mutants following site-directed mutagenesis targeting the activation segment 346-351. Enzymatic behavior of linker mutants: Single or double mutations of Asn346, Gln347, Asp349 and Asp351 demonstrated moderate loss of self-cleavage induced activation. Triple mutant A3 (Asn346Ala, Asp349Ala and Asp351Ala) and quadruple mutant A4 (Asn346, Gln347, Asp349 and Asp351) have more severe loss of function phenotype, indicating the site of activation could be any residue with this stretch of linker. FIG. 4D shows a histogram of activation efficiency after 6 hours is shown for the linker mutants. Asp349 and Asp351 could be the more preferred cleavage site, while Asn346 and Gln347 are potential cleavage sites as well.

FIGS. 5A-5D show comparison of peptide cyclization activity of WT OaEP1b, Cys247Ala and butelase 1 and the influence of the gate-keeper on ligase activity. FIG. 5A shows kinetic parameters for the cyclization of "GLPVSTKPVATRNGL" (SEQ ID NO: 18) by WT OaEP1b, Cys247Ala and butelase 1. MS analysis of the reaction is given in the panel in FIG. 5B. FIG. 5C shows a role of the gate-keeper in OaAEP1 activation. FIG. 5D shows a comparison of cyclization efficiency for various residues at the gate-keeper Cys247 position. The Gate-keeper residue Cys247 governs the ligation reaction kinetics. FIG. 5A shows the kinetic measurement of wild type OaAEP1 and Cys247Ala mutant, in comparison with Butelase 1 freshly extracted from plant. Cys247Ala has the Kcat/Km 160 times faster than wt OaAEP1b. FIG. 5B shows the schematic view of the peptide used to determine the ligation efficiency, together with the mass-spec results demonstrating the backbone ligation achieved by wild type OaAEP1 and Cys247Ala mutant. FIG. 5C shows the self-activation of the gate-keeper mutants. The self-activation is not much affected by mutations of the gate-keeper residue. Bulky side chain mutants have difficulties been fully activated. FIG. 5D shows the ligation catalytic activity is reversely correlated with the size of the side chain of Cys247 mutants.

FIG. 6A shows fluorescence detection using O2 benzylcytosine-Alexa647 of the SNAP protein and SDS PAGE analysis with Comassie blue staining detection of the protein substrate and ligated products. The reaction is schematically depicted as inset. Cys247Ala ligates well folded protein well. FIG. 6A also shows 100 nM of Cys247Ala, but not 4000 nM of wild type OaAEP1b, efficiently ligated 5 μM C-terminal modified SNAP tag protein with N-terminal modified Ubiquitin. FIG. 6B shows as little as 30 nM Cys247Ala catalyze ligation of 100 μM Ubiquitin and 500 μM biotin labelled peptide efficiently in 30 min, at room temperature, in pH 7.4 PBS buffer.

FIG. 7A shows sequence alignment of OaAEP1b, Butelase 1 and human legumain. FIG. 7B shows the exact amino acid sequence encoded in our OaAEP1 construct. Residues −85 to 0 is the fusion tags (colored in cyan), while the first 23 amino acids in AEP coding was omitted. The four residues inserted at the active site pocket observed in our crystal structure are colored in orange, and the cap domain is displayed in violet.

FIG. 8A shows side chains in the cap domain are well fit with the density. FIG. 8B shows the novel PPP loop in the core domain, which is unique to AEP ligases are nicely fit with the density.

FIGS. 11A-11D60 show a screen for substrate sequence specificity of the C- or N-terminal end peptide/protein: FIG. 11A shows Asn-$Xaa^3$-Leu-COOH; FIG. 11C shows $H_2N$-$Xaa^1$-Leu. 100 μM substrate, with 50 nM Quicklase, reacted for 5 mins at room temperature, under neutral pH (pH 7.4) standard reaction buffer. The % of self-ligated (cyclized) peptides could be used as qualitative indications of Kcat. The raw Mass-spec reading of the assay readout were also included in FIGS. 11D1-11D60.

FIG. 12A shows a graphic summary of a Basic Local Alignment Search Tool (BLAST) search in the National Center for Biotechnology Information (NCBI) database performed with the amino acid sequence set forth in SEQ ID NO:1 (OaAEP1 Cys247Ala) and FIG. 12B shows the sequences producing significant alignments.

DETAILED DESCRIPTION OF THE INVENTION

Figure 1A:
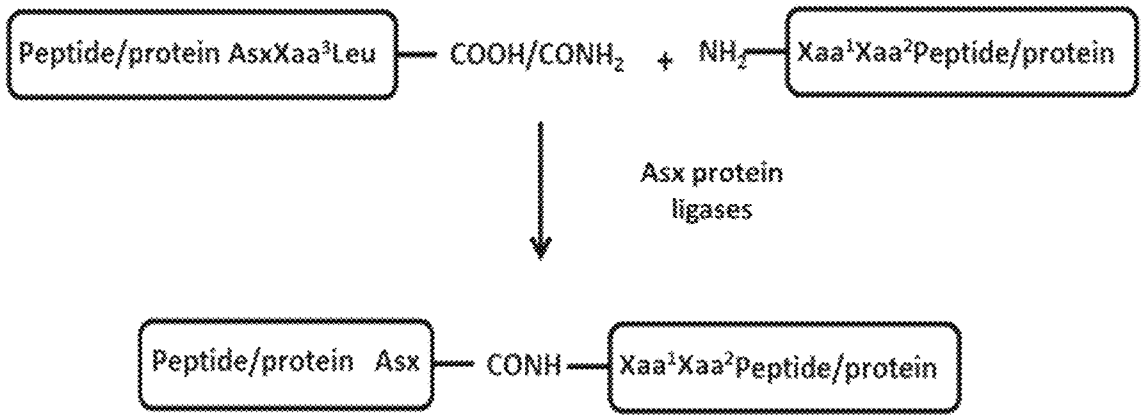
FIG. 1A shows a schematic illustration of OaAEP1 Cys247Ala (SEQ ID NO:1)-mediated peptide ligation
Figure 1B:
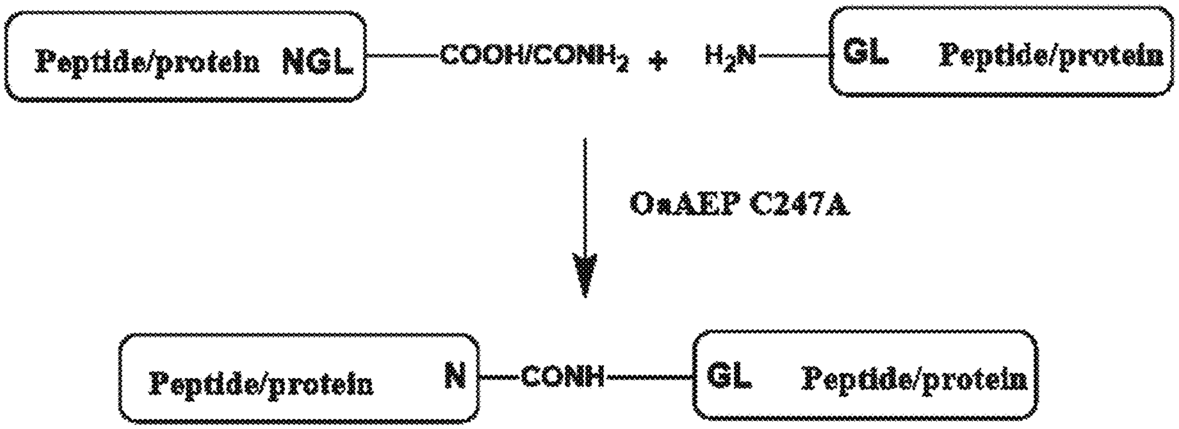
FIG. 1B shows a preferred embodiment thereof.

The following detailed description refers to, by way of illustration, specific details and embodiments in which the invention may be practiced. These embodiments are described in sufficient detail to enable those skilled in the art to practice the invention. Other embodiments may be utilized and structural, and logical changes may be made without departing from the scope of the invention. The various embodiments are not necessarily mutually exclusive, as some embodiments can be combined with one or more other embodiments to form new embodiments.

Unless otherwise defined, all technical and scientific terms used herein have the same meaning as commonly understood by one of ordinary skill in the art. The singular terms "a," "an," and "the" include plural referents unless context clearly indicates otherwise. Similarly, the word "or" is intended to include "and" unless the context clearly indicates otherwise. The term "comprises" means "includes." In case of conflict, the present specification, including explanations of terms, will control.

Breaking and forming peptidyl bonds are fundamental biochemical reactions in protein chemistry. Unlike proteases that are abundantly available, fast-acting ligases are rare. OaAEP1 is an enzyme isolated from the cyclotide-producing plant *Oldenlandia affinis* that displayed weak peptide cyclase activity, despite having a similar structural fold with other asparaginyl endopeptidases (AEP). The inventors of the present application report herein the first atomic structure of OaAEP1, at a resolution of 2.56 Å, in its pre-activation form. The structure and biochemical analysis of this enzyme reveals its activation mechanism as well as structural features important for its ligation activity. Importantly, through structure-based mutagenesis of OaAEP1, the inventors obtained an ultra-fast variant having hundreds of times faster catalytic kinetics, capable of ligating well-folded protein substrates using only sub-micro molar concentration of enzyme. In contrast, the protein-protein ligation activity in the original wild-type OaAEP1 enzyme described previously is extremely weak. Thus, the structure-based identification of a biochemical motif described herein leads to characterization of a unique and novel recombinant tool (OaAEP1 Cys247Ala having the amino acid sequence set forth in SEQ ID NO:1) and its related structural homologs that can now be used to conduct various protein labeling and modifications that were extremely challenging before. For example, more efficient peptide cyclization and peptides/proteins can be enzymatically catalyzed. Furthermore, this new type of recombinant enzyme, and its structural homologs enable novel biochemical applications, like modifications of intrinsic cellular surface proteins.

The object of the present invention is to provide a technique for ligating peptides, taking advantage of the superior site specificity and catalytic efficiency of OaAEP1 Cys247Ala-like Asx-specific protein ligases.

To this end, provided in a first aspect of the present invention is a method of generating a peptide of Formula (I)

$$P^1\text{-Asx-Xaa}^1\text{-Xaa}^2\text{-}P^2 \quad \text{(I)},$$

by ligating a first peptide of Formula (II)

$$P^1\text{-Asx-Xaa}^3\text{-Leu-COOH/CONH}_2 \quad \text{(II)}$$

to a second peptide of Formula (III)

$$H_2N\text{-Xaa}^1\text{-Xaa}^2\text{-}P^2 \quad \text{(III)},$$

wherein $P^1$ and $P^2$ are each independently any peptide, modified or unmodified, and optionally can combine such that the peptides of formula (II) and (III) are the termini of the same peptide; Asx is Asp or Asn; $Xaa^1$ is any naturally occurring amino acid; $Xaa^2$ is any naturally occurring amino acid with the exception of Pro, preferably Leu or Ile; and Xaa3 is any naturally occurring amino acid, preferably selected from the group consisting of His, Ala, Ser, Cys, Asn, Gly, Arg, Met, Lys, Gln, Leu, and Glu, by enzymatically cleaving the bond between "Asx" and "$Xaa^3$" in the first peptide of Formula (II) and ligating the fragment $P^1$-Asx of the first peptide via its C-terminus to the N-terminus of the second peptide of Formula (III) to form a ligated peptide of Formula (I), wherein the enzymatic cleavage and ligation reaction is catalyzed by a peptide ligase having the activity of OaAEP1 Cys247Ala (SEQ ID NO:1) under conditions suitable for said cleavage and ligation reaction.

In the context of the whole application, the terms "peptide", "polypeptide", and "protein" are used interchangeably to refer to polymers of amino acids of any length connected by peptide bonds. The polymer may comprise modified amino acids, it may be linear or branched, and it may be interrupted by non-amino acids. The terms also encompass an amino acid polymer that has been modified naturally or artificially; for example, by disulfide bond formation, glycosylation, lipidation, acetylation, phosphorylation, or any other manipulation, such as conjugation to a labeling moiety. However, in preferred embodiments, these terms relate to polymers of naturally occurring amino acids, as defined below, which may optionally be modified as defined above, but does not comprise non-amino acid moieties in the polymer backbone.

The term "amino acid" refers to natural and/or unnatural or synthetic amino acids, including both the D and L optical isomers, amino acid analogs (for example, norleucine is an analog of leucine) and derivatives known in the art. The term "naturally occurring amino acid", as used herein, relates to the 20 naturally occurring L-amino acids, namely Gly, Ala, Val, Leu, Ile, Phe, Cys, Met, Pro, Thr, Ser, Glu, Gln, Asp, Asn, His, Lys, Arg, Tyr, and Trp. The term "peptide bond" refers to a covalent amide linkage formed by loss of a molecule of water between the carboxyl group of one amino acid and the amino group of a second amino acid. The "-" between $P^1$ and Asx in Formula (I), as well as all "-" in Formula (I) represent peptide bonds. In addition, "Leu-COOH/CONH$_2$" represents Leucine or Leucinamide, so the "-" between "Leu" and "COOH/CONH$_2$" in Formula (II) represents the covalent bond between the α-carbon and the carboxyl or carboxamide group of Leucine/Leucinamide. Likewise, "H$_2$N-Xaa$^1$" in Formula (III) represents amino acid residue Xaa$^1$, so the "-" between "NH$_2$" and "Xaa$^1$" represents the covalent bond between the α-carbon and the amino group of Xaa$^1$. It is understood that the carboxyl/carboxamide group in the peptide of formula (II) and the amino group in the peptide of formula (III) form part of the terminal amino acid and are not additional functional groups. Generally, in all formulae depicted herein, the peptides are shown in the N- to C-terminal orientation.

Without wishing to be bound to any particular theory, it is believed that the peptide ligase having the activity of OaAEP1 Cys247Ala (SEQ ID NO:1) as described herein can also catalyze the ligation between any one substance or object comprising a terminal "Asx-Xaa$^3$-Leu-COOH/CONH$_2$" motif and any one substance or object comprising a terminal "H$_2$N-Xaa$^1$-Xaa$^2$" motif. In this connection, it should be noted that the method described herein also applies mutatis mutandis to embodiments wherein one or both of $P^1$ and $P^2$ are any substance or object other than peptide, which is also within the scope of the present application.

In various embodiments, (a) Asx is Asn or Asp; and/or (b) Xaa$^1$ is all naturally occurring amino acids; and/or (c) Xaa$^2$ is Leu or Ile; and/or (d) Xaa$^3$ is selected from the group consisting of His, Ala, Ser, Cys, Asn, Gly, Arg, Met, Lys, Gln, Leu, and Glu.

In preferred embodiments, two or more of features (a)-(d) are met, i.e., (a) and (b), (a) and (c), (a) and (d), (b) and (c), (b) and (d), or three or more features are met, i.e., (a), (b) and (c), (a), (b) and (d), (a), (c) and (d), (b), (c) and (d) or, most preferably all four are met.

In preferred embodiments, Asx is Asn, Xaa$^1$ is any naturally occurring amino acid, Xaa$^2$ is Leu, and Xaa$^3$ is His, Ser, Cys, Gly or Ala.

In more preferred embodiments, Asx is Asn, Xaa$^1$ is Arg or Gly, Xaa$^2$ is Leu, and Xaa$^3$ is His, Ala or Gly, meaning that Asx is Asn, Xaa$^1$ is Arg, Xaa$^2$ is Leu, Xaa$^3$ is His; Asx is Asn, Xaa$^1$ is Arg, Xaa$^2$ is Leu, Xaa$^3$ is Ala; Asx is Asn, Xaa$^1$ is Arg, Xaa$^2$ is Leu, Xaa$^3$ is Gly; Asx is Asn, Xaa$^1$ is Gly, Xaa$^2$ is Leu, Xaa$^3$ is His; Asx is Asn, Xaa$^1$ is Gly, Xaa$^2$ is Leu, Xaa$^3$ is Ala; or Asx is Asn, Xaa$^1$ is Gly, Xaa$^2$ is Leu, Xaa$^3$ is Gly.

Figure 11A:
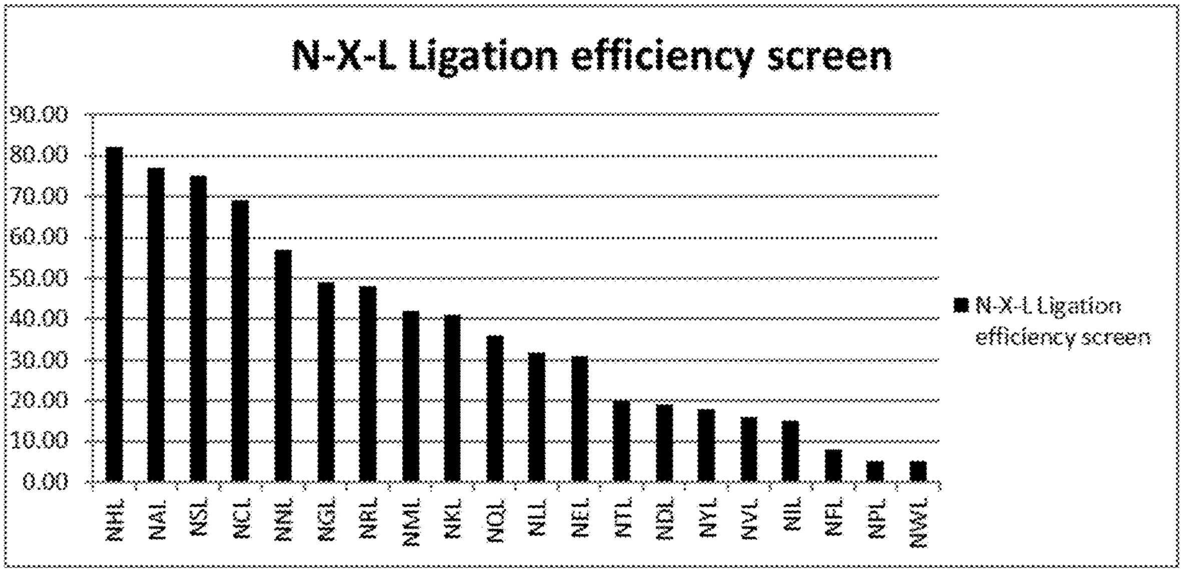
Figure 11B:
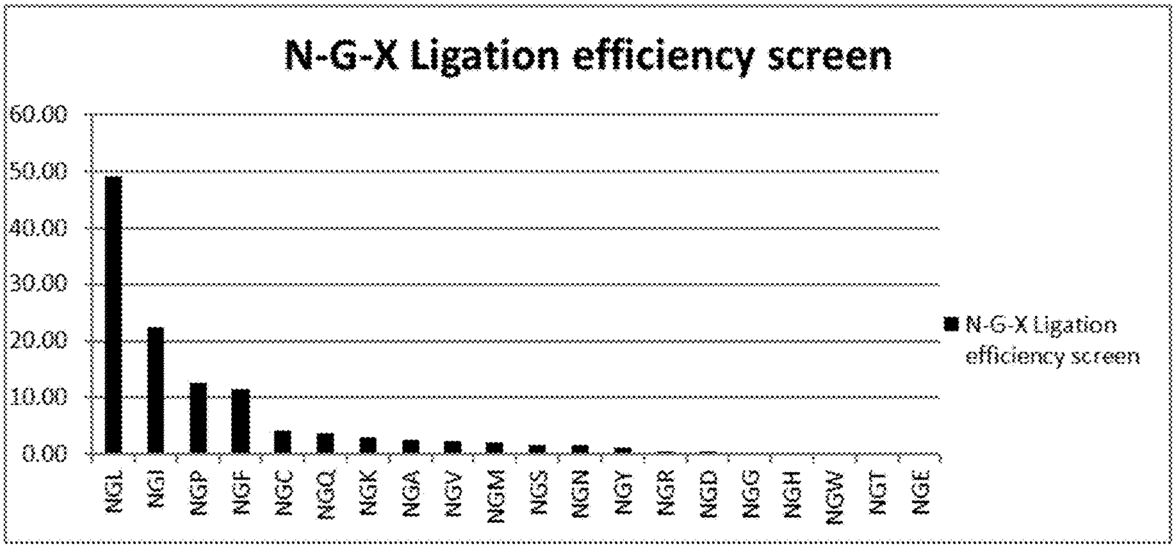
FIG. 11B shows Asn-Gly-$Xaa^2$-COOH.

It should be noted that, according to FIG. 11B, the "Leu" residue of the first peptide of Formula (II), i.e., $P^1$-Asx-Xaa$^3$-Leu-COOH/CONH$_2$, may also be replaced by another naturally occurring amino acid, e.g., Ile, Pro, Phe, Cys, Gln, or Lys, provided that said peptide in this form is still suitable for the method described herein. Such embodiments in combination with any of the embodiments described herein are also fully encompassed by the present application.

It is also envisaged that, when the first peptide and the second peptide are termini of the same peptide, i.e., $P^1$ and $P^2$ combine to form the core sequence of a peptide terminated by the sequences of formula (II) and (III), the presently disclosed method cyclizes said peptide.

The peptide ligase having the activity of OaAEP1 Cys247Ala (SEQ ID NO:1) for use in the present invention may be any oaAEP family enzymes or homologous thereof having the desired activity. The peptide ligase has an ability to site-specifically break a peptide bond and then reform a new bond with an incoming nucleophile. It is Asx-specific in that the C-terminal amino acid to which ligation occurs, i.e., the C-terminal end of the peptide that is ligated, is either Asn or Asp, preferably Asn. As set forth above, it recognizes the motif Asx-Xaa$^3$-Leu-COOH/CONH$_2$, at the C-terminus of the first peptide of Formula (II), and mediates peptide ligation by cleaving off the sorting signal Xaa$^3$-Leu-COOH/CONH$_2$ and ligating $P^1$-Asx to the N-terminal residue of the second peptide H$_2$N-Xaa$^1$-Xaa$^2$-$P^2$ to form a ligated peptide $P^1$-Asx-Xaa$^1$-Xaa$^2$-$P^2$.

In various embodiments, the peptide ligase having the activity of OaAEP1 Cys247Ala (SEQ ID NO:1) in accordance with the present application comprises, consists of, or essentially consists of:

(a) the amino acid sequence set forth in SEQ ID NO:1 (OaAEP1 Cys247Ala);

(b) an amino acid sequence that shares at least 65%, preferably at least 75%, even more preferably at least 85%, most preferably at least 95% sequence identity with, or at least 80%, preferably at least 90%, more preferably at least 95% sequence homology with the amino acid sequence as set forth in SEQ ID NO:1, provided that said peptide ligase comprises the amino acid sequence set forth in SEQ ID NO:2 at the positions corresponding to residues 247-264 of SEQ ID NO:1, which defines a unique surface structural feature of the enzyme serving as the binding site for approaching N-terminal amino group;

(c) a functional fragment of (a) or (b); or (d) an amino acid sequence containing either (a) or (b) or (c) as its essential component, with the proviso that said peptide ligase is not the wild-type OaAEP1 having the amino acid sequence set forth in SEQ ID NO:3 or butelase 1 having the amino acid sequence set forth in SEQ ID NO:4.

In various embodiments, the peptide ligase having the activity of OaAEP1 Cys247Ala (SEQ ID NO:1) comprises, consists of, or essentially consists of:

(a) the amino acid sequence set forth in SEQ ID NO:1;

(b) the amino acid sequence set forth in SEQ ID NO:5;

(c) the amino acid sequence set forth in SEQ ID NO:6;

(d) the amino acid sequence set forth in SEQ ID NO:7;
(e) the amino acid sequence set forth in SEQ ID NO:8;
(f) the amino acid sequence set forth in SEQ ID NO:9;
(g) the amino acid sequence set forth in SEQ ID NO:10; or
(h) the amino acid sequence set forth in SEQ ID NO:11.

In preferred embodiments, the peptide ligase comprises or consists of the amino acid sequence as set forth in SEQ ID NO:1 (OaAEP1 Cys247Ala).

The identity of nucleic acid or amino acid sequences is generally determined by means of a sequence comparison. This sequence comparison is based on the BLAST algorithm that is established in the existing art and commonly used (cf. for example, Altschul et al. (1990) "Basic local alignment search tool", J. Mol. Biol. 215:403-410, and Altschul et al. (1997): "Gapped BLAST and PSI-BLAST: a new generation of protein database search programs"; Nucleic Acids Res., 25, p. 3389-3402) and is effected in principle by mutually associating similar successions of nucleotides or amino acids in the nucleic acid sequences and amino acid sequences, respectively. A tabular association of the relevant positions is referred to as an "alignment." Sequence comparisons (alignments), in particular multiple sequence comparisons, are commonly prepared using computer programs which are available and known to those skilled in the art.

A comparison of this kind also allows a statement as to the similarity to one another of the sequences that are being compared. This is usually indicated as a percentage identity, which is calculated in relation to a reference sequence and its entire length. The term "sequence identity" refers to the extent that sequences are identical on a nucleotide-by-nucleotide or amino acid-by-amino acid basis over a window of comparison. Thus, a "percentage of sequence identity"' is calculated by comparing two optimally aligned sequences over the window of comparison, determining the number of positions at which the identical nucleic acid base or amino acid residue occurs in both sequences to yield the number of matched positions, dividing the number of matched positions by the total number of positions in the window of comparison (i.e., the window size), and multiplying the result by 100 to yield the percentage of sequence identity. The more broadly construed term "homology", in the context of amino acid sequences, also incorporates consideration of the conserved amino acid exchanges, i.e., amino acids having a similar chemical activity, since these usually perform similar chemical activities within the protein. The similarity of the compared sequences can therefore also be indicated as a "percentage homology" or "percentage similarity." Indications of identity and/or homology can be encountered over entire polypeptides or genes, or only over individual regions. Homologous and identical regions of various nucleic acid sequences or amino acid sequences are therefore defined by way of matches in the sequences. Such regions often exhibit identical functions. They can be small, and can encompass only a few nucleotides or amino acids. Small regions of this kind often perform functions that are essential to the overall activity of the protein. It may therefore be useful to refer sequence matches only to individual, and optionally small, regions. Unless otherwise indicated, however, indications of identity and homology herein refer to the full length of the respectively indicated nucleic acid sequence or amino acid sequence.

While it is recognized that various peptide ligases as described above may be suitable for the practice of the present invention, it is preferable to use one with potent protein ligase actively. In various embodiments, this means that it can ligate a given peptide with an efficiency of at least 50%, preferably at least 70%, more preferably at least 90%, most preferably at least 95%. Methods to determine such efficiency by, for example, ligating substrate (100 μM) in the presence of said peptide ligase (50 nM) for 30 mins in a standard reaction buffer at neutral pH and room temperature, are well known in the art and can be routinely applied by those skilled in the art, for example. It is preferred that the peptide ligases of the invention have at least 50%, more preferably at least 70%, most preferably at least 90% of the protein ligase activity of the enzyme having the amino acid sequence of SEQ ID NO:1.

Peptide ligases having the activity of OaAEP1 Cys247Ala (SEQ ID NO:1) according to the present application can comprise amino acid modifications, in particular amino acid substitutions, insertions, or deletions. Such peptide ligases are, for example, further developed by targeted genetic modification, i.e., by way of mutagenesis methods, and optimized for specific purposes or with regard to special properties (for example, with regard to their catalytic activity, stability, etc.). The objective may be to introduce targeted mutations, such as substitutions, insertions, or deletions, into the known molecules in order, for example, to alter substrate specificity and/or improve the catalytic activity. For this purpose, in particular, the surface charges and/or isoelectric point of the molecules, and thereby their interactions with the substrate, can be modified. Alternatively or additionally, the stability of the peptide ligase can be enhanced by way of one or more corresponding mutations, and its catalytic performance thereby improved. Advantageous properties of individual mutations, e.g., individual substitutions, can supplement one another.

In various embodiments, the peptide ligase may be characterized in that it is obtainable from a peptide ligase as described above as an initial molecule by single or multiple conservative amino acid substitution. The term "conservative amino acid substitution" means the exchange (substitution) of one amino acid residue for another amino acid residue, where such exchange does not lead to a change in the polarity or charge at the position of the exchanged amino acid, e.g., the exchange of a nonpolar amino acid residue for another nonpolar amino acid residue. Conservative amino acid substitutions in the context of the invention encompass, for example, G=A=S, I=V=L=M, D=E, N=Q, K=R, Y=F, and S=T.

Alternatively or additionally, the peptide ligase may be characterized in that it is obtainable from a peptide ligase contemplated herein as an initial molecule by fragmentation or by deletion, insertion, or substitution mutagenesis, and encompasses an amino acid sequence that matches the initial molecule over a length of at least 150, 160, 170, 180, 190, 200, 210, 220, 230, 240, 250, 260, 270, 280, 290, or 300 continuously connected amino acids, provided that said peptide ligase comprises the amino acid sequence set forth in SEQ ID NO:2 at the positions corresponding to residues 247-264 of SEQ ID NO:1.

In various embodiments, the present invention thus also relates to functional fragments of the peptide ligases described herein, with said fragments retaining enzymatic activity. It is preferred that they have at least 50%, more preferably at least 70%, most preferably at least 90% of the protein ligase activity of the initial molecule, preferably of the peptide ligase having the amino acid sequence of SEQ ID NO:1. The functional fragments are preferably at least 150 amino acids in length, more preferably at least 180 or 200, most preferably at least 250.

In various embodiments, the peptides to be ligated in accordance with the present application may be modified by, for example, conjugation to a labeling moiety, either covalently or non-covalently. A labeling moiety may be any molecules such as, without limitation, an affinity tag, therapeutic agent, detectable label, or scaffold molecule.

In various embodiments, the first and/or second peptide may be coupled to a solid support material.

The term "affinity tag" as used herein refers to a moiety such as biotin that can be used to separate a molecule to which the affinity tag is attached from other molecules that do not contain the affinity tag.

The term "detectable label" is intended to mean at least one label capable of directly or indirectly generating a detectable signal. In non-limiting examples, a detectable label can be an enzyme producing a detectable signal, for example, by colorimetry, fluorescence, or luminescence; a chromophore, such as a fluorescent, luminescent or dye compound, e.g., GFP; a group with an electron density detectable by electron microscopy or by virtue of their electrical property, such as conductivity, amperometry, voltammetry or impedance; detectable group, for example, the molecules of which are sufficiently large to induce detectable modifications of their physical and/or chemical characteristics (this detection can be carried out by optical methods such as diffraction, surface plasmon resonance, surface variation or contact angle variation, or physical methods such as atomic force spectroscopy or the tunnel effect; or a radioactive molecule such as $^{32}P$, $^{35}S$ or $^{125}I$.

The term "scaffold molecule" as used herein refers to a compound to which other moieties are attached, covalently or non-covalently. Various scaffold molecules such as dendrimers are well known in the art.

The term "solid support material" as used herein refers to a solid or semi-solid (e.g., a hydrogel) material onto which the peptide can be immobilized. Non-limiting examples include solid supports for peptide synthesis, magnetic beads, glass fibers, and resins.

Peptides modified by the labeling moiety may be prepared using standard techniques known to those skilled in the art of synthetic organic chemistry, or may be deduced by reference to the pertinent literature.

In various embodiments, the first and/or second peptide is a cellular surface protein such that the method results in the modification or tagging of the cellular surface protein and in result the cellular surface as such.

In a second aspect, the invention relates to a method of preparing a dimer, oligomer, or multimer of one or more peptides of interest, the method comprising the steps of:

(a) providing one or more peptides of interest having C-terminal Asx-Xaa$^3$-Leu-COOH/CONH$_2$ residues and a scaffold molecule having two or more copies of N-terminal H$_2$N-Xaa$^1$-Xaa$^2$ residues or, alternatively, providing one or more peptides of interest having N-terminal H$_2$N-Xaa$^1$-Xaa$^2$ residues and a scaffold molecule having two or more copies of C-terminal Asx-Xaa$^3$-Leu-COOH/CONH$_2$ residues, wherein Asx is Asp or Asn; Xaa$^1$ is any naturally occurring amino acid; Xaa$^2$ is any naturally occurring amino acid with the exception of Pro, preferably Leu or Ile; and Xaa$^3$ is any naturally occurring amino acid, preferably selected from the group consisting of His, Ala, Ser, Cys, Asn, Gly, Arg, Met, Lys, Gln, Leu, and Glu;

(b) providing a peptide ligase having the activity of OaAEP1 Cys247Ala (SEQ ID NO:1), as described above;

(c) preparing a mixture of the one or more peptides of interest, the scaffold molecule, and the peptide ligase having the activity of OaAEP1 Cys247Ala (SEQ ID NO:1);

(d) subjecting the mixture to conditions that allow the peptide ligase having the activity of OaAEP1 Cys247Ala (SEQ ID NO:1) to catalyze the ligation of the one or more peptides of interest to the scaffold molecule.

In various embodiments, (a) Asx is Asn or Asp, and/or (b) Xaa$^1$ is all naturally occurring amino acids, and/or (c) Xaa$^2$ is Leu or Ile, and/or (d) Xaa$^3$ is selected from the group consisting of His, Ala, Ser, Cys, Asn, Gly, Arg, Met, Lys, Gln, Leu, and Glu.

In preferred embodiments, two or more of features (a)-(d) are met, i.e., (a) and (b), (a) and (c), (a) and (d), (b) and (c), (b) and (d), or three or more features are met, i.e., (a), (b) and (c), (a), (b) and (d), (a), (c) and (d), (b), (c) and (d) or, most preferably all four are met.

In preferred embodiments, Asx is Asn, Xaa$^1$ is any naturally occurring amino acid, Xaa$^2$ is Leu, and Xaa$^3$ is His, Ser, Cys, Gly or Ala.

In more preferred embodiments, Asx is Asn, Xaa$^1$ is Arg or Gly, Xaa$^2$ is Leu, and Xaa$^3$ is His, Ala or Gly.

FIGS. 14 (*a*)-(*d*) show how hetero- or homo-dimers, oligomers, or multimers of one or more peptides of interest can be prepared according to some non-limiting embodiments. FIGS. 14 (*e*)-(*i*) show some non-limiting examples of how scaffold molecules for use in the present invention can be prepared.

In a third aspect, the invention relates to a method of modifying or tagging the surface of a target cell by one or more peptides of interest, the method comprising the steps of:

(a) providing the one or more peptides of interest having C-terminal Asx-Xaa$^3$-Leu-COOH/CONH$_2$ residues and/or having N-terminal H$_2$N-Xaa$^1$-Xaa$^2$ residues, wherein Asx is Asp or Asn; Xaa$^1$ is any naturally occurring amino acid; Xaa$^2$ is any naturally occurring amino acid with the exception of Pro, preferably Leu or Ile; and Xaa$^3$ is any naturally occurring amino acid, preferably selected from the group consisting of His, Ala, Ser, Cys, Asn, Gly, Arg, Met, Lys, Gln, Leu, and Glu;

(b) providing a peptide ligase having the activity of OaAEP1 Cys247Ala (SEQ ID NO:1), as described above;

(c) contacting the target cell with the one or more peptides of interest and the peptide ligase having the activity of OaAEP1 Cys247Ala (SEQ ID NO:1);

(d) subjecting the target cell to conditions that allow the peptide ligase having the activity of OaAEP1 Cys247Ala (SEQ ID NO:1) to catalyze the ligation of the one or more peptides of interest to a cellular surface protein of the target cell.

In certain embodiments, the wild-type OaAEP1 having the amino acid sequence of SEQ ID NO:3 may also be used in this method, probably with a compromised efficiency.

In various embodiments, (a) Asx is Asn or Asp; and/or (b) Xaa$^1$ is all naturally occurring amino acids; and/or (c) Xaa$^2$ is Leu or Ile; and/or (d) Xaa$^3$ is selected from the group consisting of His, Ala, Ser, Cys, Asn, Gly, Arg, Met, Lys, Gln, Leu, and Glu.

In preferred embodiments, two or more of features (a)-(d) are met, i.e., (a) and (b), (a) and (c), (a) and (d), (b) and (c), (b) and (d), or three or more features are met, i.e., (a), (b) and (c), (a), (b) and (d), (a), (c) and (d), (b), (c) and (d) or, most preferably all four are met.

In preferred embodiments, Asx is Asn, $Xaa^1$ is any naturally occurring amino acid, $Xaa^2$ is Leu, and $Xaa^3$ is His, Ser, Cys, Gly or Ala.

In more preferred embodiments, Asx is Asn, $Xaa^1$ is Arg or Gly, $Xaa^2$ is Leu, and $Xaa^3$ is His, Ala or Gly.

In various embodiments, the method further comprises removing the unligated one or more peptides from the target cell after step (d).

The one or more peptides of interest may be functionalized to bind a variety of cargo molecules. In various embodiments, the one or more peptides of interest comprise a labeling moiety such as an affinity tag, therapeutic agent, detectable label, or scaffold molecule, as already described above. The one or more peptides of interest may also be coupled to a solid support material.

Figure 15A:
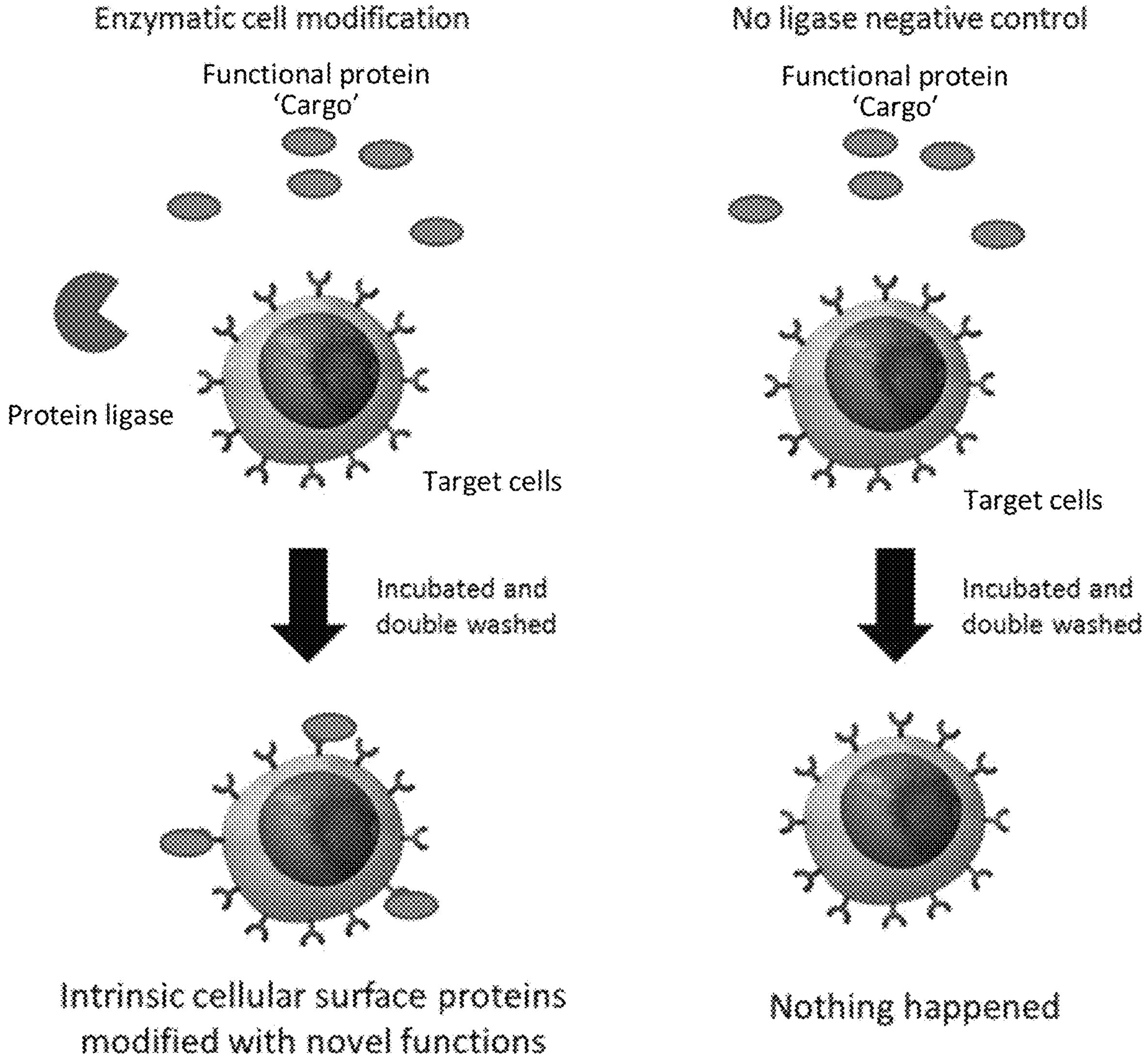
FIG. 15A shows a schematic illustration of the direct cellular modification procedure mediated by OaAEP1 Cys247Ala (SEQ ID NO:1).

FIG. 15A shows how a target cell can be tagged according to a non-limiting embodiment of the invention.

The method described herein may be applicable to all types of cells in vitro, ex vivo, or in vivo. The target cell may be any prokaryotic or eukaryotic cell, e.g., a bacterial, yeast, plant, or human cell; it may be a cancer cell, oocyte, embryonic stem cell, hematopoietic stem cell, or any other differentiated or undifferentiated cell, provided that the target cell expresses a surface polypeptide having C-terminal Asx-$Xaa^3$-Leu-COOH/$CONH_2$ or N-terminal $H_2N$-$Xaa^1$-$Xaa^2$ residues that are accessible to the one or more peptides of interest.

In preferred embodiments, the target cell expresses endogenous surface proteins suited for ligation to the one or more peptides of interest. However, the target cell may also recombinantly express a surface polypeptide having N-terminal $H_2N$-$Xaa^1$-$Xaa^2$ or C-terminal Asx-$Xaa^3$-Leu-COOH residues for ease of tagging by the peptide of interest.

The term "recombinantly express" as used herein refers to the expression of said polypeptide by recombinant DNA technology.

It is also within the scope of the present invention that the one or more peptides of interest may be polypeptides endogenously or recombinantly expressed on the surface of the target cell, in which case no additional said peptides need to be provided and the method described herein results in hetero- or homo-dimerization, oligomerization, or multimerization of surface proteins of the target cell.

It is therefore believed that the present invention provides a versatile and fast-acting technology for modifying or tagging cell surface by attaching modified or unmodified peptides of interest. Compared to conventional chemical labeling strategies, this method enables specific and fast conjugation to the N- and/or C-terminus of surface proteins.

In a fourth aspect, the invention relates to the ligated peptides and/or tagged target cells obtainable according to any of the methods of the invention.

In a fifth aspect, the invention relates to the peptide ligase OaAEP1 Cys247Ala having the amino acid sequence of SEQ ID NO:1 and other peptide ligases having the activity thereof, as described above, as well as kits comprising any of said peptide ligases, in particular OaAEP1 Cys247Ala (SEQ ID NO:1).

In still another aspect, the present invention relates to the use of a peptide ligase having the activity of OaAEP1 Cys247Ala (SEQ ID NO:1) for the ligation of two peptides, as described herein.

The present invention is further illustrated by the following examples. However, it should be understood, that the invention is not limited to the exemplified embodiments.

EXAMPLES

Materials and Methods

Quicklase Preparation:

OaAEP1 was cloned and expressed in *E. coli* as an ubiquitin fusion protein. A gene with codons optimized for expression in *E. coli*, encoding a protein (SEQ ID NO:12) composed of a N-terminal hexa-His tag (SEQ ID NO:13), the 76 amino-acid residues human ubiquitin (SEQ ID NO:14), and residues 24-474 of OaAEP1 (SEQ ID NO:15, devoid of the OaAEP1 signal peptide) was synthesized by Genescript, USA.

The clone is OaAEP1 one amino acid different from OaAEP1b (SEQ ID NO:3) (with E371V mutation). OaAEP1 was cloned from mRNA and OaAEP1b from genomic DNA sequence. Nevertheless, the wild type constructs (OaAEP1, SEQ ID NO:3) of the inventors behaves essentially the same as previously reported (OaEP1b, SEQ ID NO:3 with E371V mutation).

The amino acid sequence of this composite protein construct is shown in FIG. S1B. The gene was inserted into the coding region (NcoI-NdeI) of the pET-28b (+) vector and amplified. Recombinant expression of OaAEP1 in *E. coli* (using either Bl21DE3 or T7 Shuffle from New England Biolabs, USA) was performed following the protocol reported previously, using a concentration of 0.4 mM IPTG to induce protein expression at 16° C. for 20 hours. Cells were then harvested by centrifugation at 4,000 g for 15 min at 4° C. and resuspended in a lysis buffer containing 50 mM Tris-HCl, pH 7.4, 150 mM NaCl, 0.05% (v/v) CHAPS, 10% (v/v) glycerol. Lysis was done by passing three times the homogenized cells through an Emulsiflex-C3 (Avestin, USA) high-pressure apparatus, at 1500 psi. The supernatant fraction, which contains His-Ub-AEP-FL (SEQ ID NO:12) and Ub-AEP-FL (SEQ ID NO:15) was further purified by metal affinity using a Ni-NTA column (Bio-Rad). His tag-containing proteins bound to the column were eluted using a linear imidazole gradient from 0 to 500 mM in a buffer containing 50 mM Tris-HCl, pH 8.0, 150 mM NaCl, 0.05% (v/v) CHAPS, 10% (v/v) glycerol. Ni-NTA elution fractions containing the protein were diluted and loaded onto two 5 ml HiTrap Q Sepharose high performance columns connected in series (GE Healthcare; 2 ml sample per ml of resin). Bound proteins were eluted using a continuous salt gradient of 0-30% of buffer B: 20 mM Bis-Tris propane, 2 M NaCl, pH 7. Finally, the protein was purified through a SEC column that had been pre-equilibrated in PBS buffer.

To self-activate OaAEP1, 1 mM EDTA and 0.5 mM Tris (2-carboxyethyl) phosphine hydrochloride were added to the immature protein and the pH of the solution was adjusted to 4 with glacial acetic acid. Fractions containing the protein (as analyzed by SDS-PAGE) were pooled and then incubated for 3 to 16 hours at room temperature or 37° C. Protein precipitation at this pH allowed removal of the bulk of the contaminating proteins by centrifugation. Activated proteins were concentrated by ultracentrifugation using a 50 kDa cutoff concentrator (Sartorius) and stored at −80° C.

Wild type and mutant ubiquitin (containing the additional "NGL" sequence at its C-terminal end) and SNAP tag (New England Biolabs) were cloned into pET47b vector and expressed in Bl21(DE3) *E. coli* cells. Purification was done by metal affinity using Ni-NTA as described above. This was followed by precision protease (GE healthcare) digestion to remove the N-terminal hexa-histidine tag and SEC purification. Mutagenesis was performed using Kapa-Hifi polymerase (Kapa Biosystems) and two primers far away from each other with opposite directions.

Cys247Ala mutant was obtained through mutagenesis PCR of using primer AEP-C247A-Mut:

```
                                        (SEQ ID NO: 16)
CACCACCGAAAGCAGCTGGGCCTACTATTGCCCGGCGC.
```

Peptides and Peptide Cyclization Assay

Native and modified amino acids were purchased from Sigma-Aldrich (USA). All peptides used in this manuscript were synthesized in-house using the solid-phase method and HPLC purified. Cyclization assays were performed in 50-μl reaction mixtures containing 20 mM phosphate buffer, ligases (5 to 700 nM) and peptide substrates (10 to 300 μM). Each reaction was performed in triplicate at 37° C. and quenched by adding 5 μl of 1 M HCl solution. The peptides were separated by using a reversed-phase C18 analytical column (150×2.1 mm, Vydac) with a linear gradient from 10% to 50% acetonitrile over 15 min on a Nexera UHPLC system (Shimadzu). For kinetic analysis, the concentrations of WT OaAEP1, mutant OaAEP1, and butelase 1 were fixed at 700 nM, 50 nM, and 20 nM, respectively. The cyclization velocities were calculated by converting the HPLC-peak areas of remained linear precursors or the cyclized products into concentrations. The identity of each HPLC peak was analyzed by MALDI-TOF MS (ABI 4800 MALDI TOF/TOF). The velocities were input into GraphPad Prism (GraphPad Software, San Diego) to obtain the Michaelis-Menten curve and the kinetic parameters (kcat and Km). Comparison for the cyclization efficiency of various OaAEP1 mutants were performed in a volume of 20 μl of the reaction mixture and analyzed by MALDI-TOF MS after 10 mins or 1 hour ligation reaction.

For quick assessment of the substrate specificity of quicklase, 100 μM peptide substrate ($Xaa^1Xaa^2$YRRGRLYRRN$Xaa^3Xaa^4$, (SEQ ID NO:17) were used, with 50 nM Quicklase, reacted for 5 mins at room temperature, under neutral pH (pH 7.4) standard reaction buffer. The % of self-ligated (cyclized) peptides could be used as qualitative indications of Kcat. In each screen, only one of the residue is modified, and the default amino acid at $Xaa^1$ position is Gly, at $Xaa^2$ position is Leu, and at $Xaa^3$ position is Gly, and at the $Xaa^4$ position is Leu, in this screen (FIG. 11).

List of Sequence ID NOs and detailed amino acid sequences described herein

1. SEQ ID NO:1

Common Name: OaAEP1 Cys247Ala (Quicklase)

Source: *Ovaloparmena affinis*

Sequence:

```
MVRYLAGAVLLLVVLSVAAAVSGARDGDYLHLPSEVSRFFRPQETNDDH

GEDSVGTRWAVLIAGSKGYANYRHQAGVCHAYQILKRGGLKDENIVVFM

YDDIAYNESNPRPGVIINSPHGSDVYAGVPKDYTGEEVNAKNFLAAILG

NKSAITGGSGKVVDSGPNDHIFIYYTDHGAAGVIGMPSKPYLYADELND

ALKKKHASGTYKSLVFYLEACESGSMFEGILPEDLNIYALTSTNTTESS

WAYYCPAQENPPPPEYNVCLGDLFSVAWLEDSDVQNSWYETLNQQYHHV
```

-continued

```
DKRISHASHATQYGNLKLGEEGLFVYMGSNPANDNYTSLDGNALTPSSI

VVNQRDADLLHLWEKFRKAPEGSARKEEAQTQIFKAMSHRVHIDSSIKL

IGKLLFGIEKCTEILNAVRPAGQPLVDDWACLRSLVGTFETHCGSLSEY

GMRHTRTIANICNAGISEEQMAEAASQACASIP
```

2. SEQ ID NO:2

Common Name: critical structural motif responsible for efficient protein ligation at the positions corresponding to residues 247-264 of SEQ ID NO:1;

Source: Based on structural analysis of this application

Sequence:

$(G/A/S/C)^{247}$-X-Y-$C^{250}$-P-X-X-X-X-X-P-P-P-E-Y-X-X-$C^{264}$

*X means any amino acids that do not disrupt the structural fold of the remaining conserved amino acids.

**Small amino acids (Gly, Ala, Ser or Cys) at position 247 of this structural motif allows efficient protein ligation. An Cys disulfide bond between Cys250 and Cys264 stabilize this structural motif.

3. SEQ ID NO:3

Common Name: wild type OaAEP1

Source: *Ovaloparmena affinis*

Sequence:

```
MVRYLAGAVLLLVVLSVAAAVSGARDGDYLHLPSEVSRFFRPQETNDDHG

EDSVGTRWAVLIAGSKGYANYRHQAGVCHAYQILKRGGLKDENIVVFMYD

DIAYNESNPRPGVIINSPHGSDVYAGVPKDYTGEEVNAKNFLAAILGNKS

AITGGSGKVVDSGPNDHIFIYYTDHGAAGVIGMPSKPYLYADELNDALKK

KHASGTYKSLVFYLEACESGSMFEGILPEDLNIYALTSTNTTESSWCYYC

PAQENPPPPEYNVCLGDLFSVAWLEDSDVQNSWYETLNQQYHHVDKRISH

ASHATQYGNLKLGEEGLFVYMGSNPANDNYTSLDGNALTPSSIVVNQRDA

DLLHLWEKFRKAPEGSARKEEAQTQIFKAMSHRVHIDSSIKLIGKLLFGI

EKCTEILNAVRPAGQPLVDDWACLRSLVGTFETHCGSLSEYGMRHTRTIA

NICNAGISEEQMAEAASQACASIP
```

4. SEQ ID NO:4

Common Name: AEP1 from *Clitoria ternatea*, Butelase1

Source: *Clitoria ternatea*

Sequence:

```
IRDDFLRLPSQASKFFQADDNVEGTRWAVLVAGSKGYVNYRHQADVCHAY

QILKKGGLKDENIIVFMYDDIAYNESNPHPGVIINHPYGSDVYKGVPKDY

VGEDINPPNFYAVLLANKSALTGTGSGKVLDSGPNDHVFIYYTDHGGAGV

LGMPSKPYIAASDLNDVLKKKHASGTYKSIVFYVESCESGSMFDGLLPED

HNIYVMGASDTGESSWVTYCPLQHPSPPPEYDVCVGDLFSVAWLEDCDVH

NLQTETFQQQYEVVKNKTIVALIEDGTHVVQYGDVGLSKQTLFVYMGTDP

ANDNNTFTDKNSLGTPRKAVSQRDADLIHYWEKYRRAPEGSSRKAEAKKQ

LREVMAHRMHIDNSVKHIGKLLFGIEKGHKMLNNVRPAGLPVVDDWDCFK
```

-continued

TLIRTFETHCGSLSEYGMKHMRSFANLCNAGIRKEQMAEASAQACVSIPD
NPWSSLHAGFSV

5. SEQ ID NO:5
Common Name: uncharacterized AEP from coffee [CDP08231.1]
Source: *Coffea canephora*
Sequence:

MMRYATAALLLLALSIIAVAEARDNFLKLPSEIADFFHPKERSDAGGDSV
GTRWAVLIAGSNGYWNYRHQADVCHAYQILKRGGLKDENIVVFMYDDIAY
NEENPRPGVIINSPHGADVYQGVPKDYTGDDVNAKNFLAAILGDKTAITG
GSGKVVDSGPNDHIFIYYTDHGGPGVLGTPSGPYLYADDLNEVLKKKHAS
GTYKSLVFYLEACESGSIFEGLLPEDLNIYATTASNAEESSWGTYCPGEY
PSPPPEYETCLGDLYSVAWMEDSEIHNLHTETLKQQYHLVKKRTSSSNSA
YGSHVMQYGDLKLSLEDLFLYMGTNPANDNYTFVDENSLRPSSKAVNQRD
ADLLHFWDKFRKAPEGSARKVEAQKQVVEAMSHRMHIDNSVKLIGKLLFG
IEKGSEILNSVRPAGHPLADDWDCLKSLVRTFETHCGSLSQYGMKHMRSI
ANICNAGIKKDQMAEAAAQACVSLPSNSWSSLHRGFSA

6. SEQ ID NO:6
Common Name: uncharacterized enzyme [XP_017229093.1]
Source: *Daucus carota* subsp. *sativus*
Sequence:

MVRYLAGAVALLVVVSISAVVESRRDIVGDVLKLPSEVSSFFRPVAEEED
SVGTRWAVLIAGSNGYWNYRHQADICHAYQLLRRGGVKEENIVVFMYDDI
AYDEENPRPGVIINSPHGSDVYKGVPKDYTGEDVTVNNVFAAILGDKSAT
TGGSGKVVDSGPNDHIFIYYSDHGGPGVLGMPTNPYMYAGDLVDVLKKKH
ASGTYKSMVFYLEACESGSIFEGLLPEGLNIYATTASNAYESSWGTYCPG
EYPSPPPEYETCLGDLYSVAWMEDSDIHNLRTETLRQQYQQVKKRTSNDN
SGWGSHVMQYGDLKLSTEELFMYMGTNPANDNFTFVDDNSLRLSSSKAVN
QRDADLLHFWDKYRKAPEGSDRKIAAQKQFSEAMSHRMHLDNSIQLIGKL
LFGIDTASEVLTTVRPSGQPLVDDWLCLKKLVRTFETYCGSLSQYGMKHM
RSIANICNAGISEEQMSEASAQACVTFPSNPWSSVNKGFTA

7. SEQ ID NO:7
Common Name: Peptidase C13, legumain [OMO66906.1]
Source: *Corchorus capsularis*
Sequence:

MTRLVAGVILLLLSVTGIVSAGRDATGDVLRLPSEASRFFRPSDDDEVGT
RWAVLIAGSNGYWNYRHQADVCHAYQLLKKGGLKDENIIVFMYDDIAYNY
ENPRQGIIINSPHGDDVYQGVPKDYTGEEVTVHNFLAAILGNKTAITGGS
GKVVDSGPNDHIFIYYTDHGGPGVLGMPTYPYLYADELIDTLKKKHASGT
YKSLVFYLEACESGSIFEGLLPEGLNIYATTASNADESSWGTYCPGEYPS
PPPEYETCLGDLYSVAWMEDSDLHNLRTETLHQQYELVKKRTLNGNSAYG

-continued

SHVMQYGDVGLAKEHLFLYLGTNPANDNFTFIDENSLQPPAKAVNQRDAD
LVHFWDKYRKAPDGSARKVEAQKQVVEAMSHRMHVDNSIQLIGKLLFGIE
RGADVLKTVRPAGQPLVDDWKCLKSMVRTFETHCGSLAQYGMKHMRSIAN
ICNAGIQTEQIAEASAQACVSIPSGQWSSIQKGFSA

8. SEQ ID NO:8
Common Name: Peptidase C13, legumain [OMO86616.1]
Source: *Corchorus olitorius*
Sequence:

MTRLVAGVILLLLSVTGIASAGRDATGDVLRLPSEASRFFRPSDDDEVGT
RWAVLIAGSNGYWNYRHQADVCHAYQLLKKGGLKDENIIVFMYDDIAFNY
ENPRQGIIINSPHGDDVYQDVPKDYTGEEVTVHNFLAAILGNKTAIKGGS
GKVVDSGPNDHIFIYYTDHGGPGVLGMPTYPYLYADELIDTLKKKHASGT
YKSLVFYLEACESGSIFEGLLPEGLNIYATTASNADESSWGTYCPGEYPS
PPPEYETCLGDLYSVAWMEDSDLHNLRTETLHQQYELVKKRTLNGNSAYG
SHVMQYGDVGLAKEHLFLYLGTNPANDNFTFIDENSLQPPAKAVNQRDAD
LVHFWDKYRKAPDGSVRKVEAQKQVVEAMSHRMHVDNSIQLIGKLLFGIE
RGADVLKTVRPAGQPLVDDWKCLKSMVRTFETHCGSLAQYGMKHMRSIAN
ICNAGIQTEQMAEASSQACVSIPSGQWSSIQKGFSA

9. SEQ ID NO:9
Common Name: vacuolar-processing enzyme [XP_012077326.1]
Source: *Jatropha curcas*
Sequence:

MTRLATGVILLLLALCVVSSAGSRDIVGDVLRLPSEASRFFRPGGAHVAK
EDDSTGTRWAILIAGSNGYWNYRHQADVCHAYQLLKKGGLKDENIIVFMY
DDIAFNKENPRPGVIINNPYGEDVYKGVPKDYTGEDVNVNNFFAAILGNK
TAITGGSGKVVDSGPNDHIFIYYTDHGGPGVLGMPTNPYLYANDLIDVLI
KKHASGTYKSLVFYLEACESGSIFEGLLPEGLNIYATTAANAEESSWGTY
CPGEYPSPPPEYETCLGDLYSVAWMEDSDVHNLQTETLRQQYQLVKKRTA
NGNSAYGSHVMQYGDVGLSKDNLFLYMGTNPANENYTFVDENSLRPPSKA
VNQRDADLVHFWDKYRKAPDGSTRKIQAQKQFVEAMSHRMHLDHSMKLIG
KLLFGIGKGSEVLNAIRPAGQPLVDDWVCLKTLVRTFETHCGSLSQYGMK
HMRSLANLCNAGIREDQMAEASAQACVSIPSGPWSSLHKGFSA

10. SEQ ID NO:10
Common Name: uncharacterized enzyme [AGC94758.1]
Source: *Malus hupehensis*
Sequence:

MTRLASAVVLLFLASVLASAAGSRDLIGDVLRLPSEASRFFGRGDDAPDQ
QDDGTVGTRWAVLIAGSNGYWNYRHQADICHAYQLLKKGGLKDENIVVFM
YDDIAYNEENPRQGVIINSPHGSDVYEGVPKDYTGEDVTVNNFFAAILGN
KTALTGGSGKVVDSGPNDHIFIYYTDHGGPGILGMPTSPYIYANDLIEVL
KKKHAAGTYRSLVFYLEACESGSIFEGLLPEGLNIFATTASNAEESSWGT

-continued

YCPGEYPSPPPEYDTCLGDLYSVAWMEDSDVHNLRSETLHQQYELVKTRA

ANDNSGSGSHVMQYGDVGLSKNNLFVYMGTNPANDNYTFLGENSLRPSSK

AVNQRDADLLHFWHKYRKAPEGSARKIQAQKDFVEAMSHRMHIDQTMKLI

GKLLFGIEKGPQVLNAVRPAGQPLVDDWDCLKTMVRSFETHCGSLSQYGM

KHMRSLANICNAGMTQEQMAEASAQACVSAPSGRWSSLHRGFSA

11. SEQ ID NO:11

Common Name: vacuolar-processing enzyme-like [XP_009361606.1]

Source: *Pyrus* x *bretschneideri*

Sequence:

MTRFAGAVVLLFLASVLASAAGSRDLIGDVLRLPSEASRFFGRGDDAPDQ

QDDGTVGTRWAVLIAGSNGYWNYRHQADICHAYQLLKKGGLKDENIVVFM

YDDIAYNEENPRQGVIINNPQGSDVYEGVPKDYTGEDVTVNNFFAAILGN

KTALTGGSGKVVDSGPNDHIFIYYTDHGGPGVLGMPTSPYIYANDLIEVL

KKKHAAGTYKSLVFYLEACESGSIFEGLLPEGLNIFATTASNAEESSWGT

YCPGEYPSPPPEYETCLGDLYSVAWMEDSDIHNLRSETLHQQYELVKTRT

ANDNYGFGSHVMQYGDVGLSKNNLFVYMGTNPANDNYTFLGENSLRPSSK

AVNQRDADLLHFWHKYRKAPEGSARKVQAQKDFVEAMSHRMHIDQTMKLI

GKLLFGIEKGPQVLNAVRPAGQPLVDDWDCLKTMVRSFETHCGSLSQYGM

KHMRSLANICNAGMTQEQMAEASAQACVSAPSSRWSSLHRGFSA

12. SEQ ID NO:12

Common Name: wild type OaAEP1 (SEQ ID NO:3) Construct for recombinant expression Sequence:

MGMAHHHHHHMQIFVKTLTGKTITLEVEPSDTIENVKAKIQDKEGIPPDQ

QRLIFAGKQLEDGRTLSDYNIQKESTLHLVLRLRGGARDGDYLHLPSEVS

RFFRPQETNDDHGEDSVGTRWAVLIAGSKGYANYRHQAGVCHAYQILKRG

GLKDENIVVFMYDDIAYNESNPRPGVIINSPHGSDVYAGVPKDYTGEEVN

AKNFLAAILGNKSAITGGSGKVVDSGPNDHIFIYYTDHGAAGVIGMPSKP

YLYADELNDALKKKHASGTYKSLVFYLEACESGSMFEGILPEDLNIYALT

STNTTESSWCYYCPAQENPPPPEYNVCLGDLFSVAWLEDSDVQNSWYETL

NQQYHHVDKRISHASHATQYGNLKLGEEGLFVYMGSNPANDNYTSLDGNA

LTPSSIVVNQRDADLLHLWEKFRKAPEGSARKEEAQTQIFKAMSHRVHID

SSIKLIGKLLFGIEKCTEILNAVRPAGQPLVDDWACLRSLVGTFETHCGS

LSEYGMRHTRTIANICNAGISEEQMAEAASQACASIP

13. SEQ ID NO:13

Common Name: Hexa-His tag (recombinant)

Sequence:

MGMAHHHHHH

14. SEQ ID NO:14

Common Name: Ubiquitin tag for assisting recombinant protein expression (recombinant)

Sequence:

MQIFVKTLTGKTITLEVEPSDTIENVKAKIQDKEGIPPDQQRLIFAGKQL

EDGRTLSDYNIQKESTLHLVLRLRGG

15. SEQ ID NO:15

Common Name: pre-activation form of wild type OaAEP1 (construct being crystalized in this application, PDB code: 5H0I)

Sequence:

ARGDYLHLPSEVSRFFRPQETNDDHGEDSVGTRWAVLIAGSKGYANYRHQ

AGVCHAYQILKRGGLKDENIVVFMYDDIAYNESNPRPGVIINSPHGSDVY

AGVPKDYTGEEVNAKNFLAAILGNKSAITGGSGKVVDSGPNDHIFIYYTD

HGAAGVIGMPSKPYLYADELNDALKKKHASGTYKSLVFYLEACESGSMFE

GILPEDLNIYALTSTNTTESSWCYYCPAQENPPPPEYNVCLGDLFSVAWL

EDSDVQNSWYETLNQQYHHVDKRISHASHATQYGNLKLGEEGLFVYMGSN

PANDNYTSLDGNALTPSSIVVNQRDADLLHLWEKFRKAPEGSARKEEAQT

QIFKAMSHRVHIDSSIKLIGKLLFGIEKCTEILNAVRPAGQPLVDDWACL

RSLVGTFETHCGSLSEYGMRHTRTIANICNAGISEEQMAEAASQACASIP

16. SEQ ID NO:16

Common Name: AEP-C247A-Mut, primer used for mutagenesis, converting Seq ID NO:3 to Seq ID NO:1.

Sequence:

CACCACCGAAAGCAGCTGGGCCTACTATTGCCCGGCGC

17. SEQ ID NO:17

Common Name: Peptide template used for characterizing recognition sequence specificity of Quicklase Sequence: $Xaa^1Xaa^2$YRRGRLYRRN$Xaa^3Xaa^4$ In each screen, only one of the residue is modified, and the default amino acid at $Xaa^1$ position is Gly, at $Xaa^2$ position is Leu, and at $Xaa^3$ position is Gly, and at the $Xaa^4$ position is Leu, in this screen.

Example 1: Quicklase OaAEP1 Mediates Peptide Ligation

AEP-like plant peptide ligases share a conserved protein architecture also found in human legumain endopeptidase (hlegum) (Ishii, S., Methods Enzymol, 1994. 244: p. 604-15; Chen, J. M., et al., J Biol Chem, 1997. 272(12): p. 8090-8). Plant AEPs have an N-terminal signal sequence of ~20-30 amino acids that direct them to the plant vacuolar compartment, followed by an enzymatic core domain. At the C-terminus of the core domain, a ~130-residues "cap" or prodomain entirely covers the active site, keeping the immature protein in an inactive zymogenic state. The core and prodomain are connected by a "linker" defined as spanning residues 325-346 of the protein (FIG. 2A). Activation of plant AEP enzymatic activities requires proteolytic maturation at an acidic pH of about 3.7, at which the pro-domain is cleaved either in cis by the proteolytic activity of the core domain itself or in trans by activated Asx proteases present in the milieu, and released from the core domain. The precise cleavage site(s) within the linker and pro-domain, leading to the formation of a mature active plant AEP ligase remain poorly characterized. In the case of butelase 1, Asn383 was hypothesized to constitute the site of cap domain cleavage (Nguyen, G. K., et al., Nat Chem Biol, 2014. 10(9): p. 732-8), while several potential cleavage sites spanning region 328-351 of the protein were proposed for OaAEP1 (FIG. 2A and FIGS. 7A and 7B) (Harris, K. S., et al., Nat Commun, 2015. 6: p. 10199). Amino-acid sequence alignments of plant AEP-like ligases with AEP peptidases such as hlegum also reveal the presence of several evolutionary conserved residues in the catalytic pocket (FIGS. 7A and 7B) (Nguyen, G. K., et al., Nat Chem Biol, 2014. 10(9): p. 732-8; Harris, K. S., et al., Nat Commun, 2015. 6: p. 10199; Dall, E., et al., Angew Chem Int Ed Engl, 2015. 54(10): p. 2917-21; Dall, E. and H. Brandstetter, Biochimie, 2016. 122: p. 126-50; Saska, I., et al., J Biol Chem, 2007. 282(40): p. 29721-8). Therefore, what determines how these closely similar enzymes preferentially function either as ligase or protease remains elusive. Herein reported is a crystal structure of OaAEP1 in its zymogenic form revealing how the amide group of Gln347 a residue at the N-terminus of the pro-domain can be accommodated in the catalytic pocket. Based on the OaAEP1 structure, a series of OaAEP1 mutants was generated to better understand the activation mechanism and catalytic activities of plant AEP ligases. It was found that that the segment 346-351 plays a critical role for the maturation of OaAEP1b, because mutating Asx residues within this segment severely disrupts AEP ligase activation. A major determinant governing the efficiency of peptide ligation activities of OaAEP1 is the side chain at residue 247, which is located near the catalytic Cys217-His175 dyad: larger side-chains at this position completely abolish ligase enzymatic activities, while smaller side-chains allow ligation reactions to take place at a much faster rate. Accordingly, it was demonstrated that the single Cys247Ala mutant of OaAEP1 has peptide ligase catalytic activity ~160 times faster than the wild type OaAEP1 enzyme, comparable to the butelase 1 enzyme extracted from plant. It was also shown that Cys247Ala can efficiently catalyze the ligation of two well-folded proteins: ubiquitin and SNAP tag protein, using only sub-micro molar concentrations of the recombinant enzyme.

In more detail:

OaAEP1 was cloned and expressed in *E. coli* as an ubiquitin fusion protein as reported earlier (FIGS. 2A-2E) (Harris, K. S., et al., Nat Commun, 2015. 6: p. 10199). Using ion exchange and size exclusion chromatography (SEC), sufficient amounts of pure protein suitable for enzymatic and structural analysis were obtained (FIG. 2B). At the neutral pH of purification (pH=7.4), OaAEP1 was mainly present as a heterodimer, where both monomers are in their zymogenic form, but only one monomer had retained in addition the ubiquitin and N-terminal His-tag, while the fusion moiety was cleaved in the other monomer (labeled as "His-Ub-AEP-FL" and "AEP-FL" in FIG. 2B and FIG. 2C). This heterodimer was subjected to crystallization trials for structural studies (see below). In agreement with reference (Harris, K. S., et al., Nat Commun, 2015. 6: p. 10199), activation of OaAEP1 was optimum for pH values in the range of 3.4-4.0 (FIG. 2D). Following activation, OaAEP1 converts to a monomer in solution according to SEC analysis ("AEP-holo" in FIG. 2C). To test the ability of the protein to be activated in trans, the catalytic residue Cys217 was mutated into Ser217. As anticipated, the Cys217Ser mutant only displayed background level activation and ligase activity (FIG. 2E). However, activation of the inactive mutant could be rescued in trans by addition of only 10% of wild type OaAEP1 to the inactive enzyme (FIG. 2E). This suggested that similar trans-cleavage processing events could also be at play during OaAEP1 activation and that Cys217 is the active site residue for both cis and trans-activation.

Figure 3F:
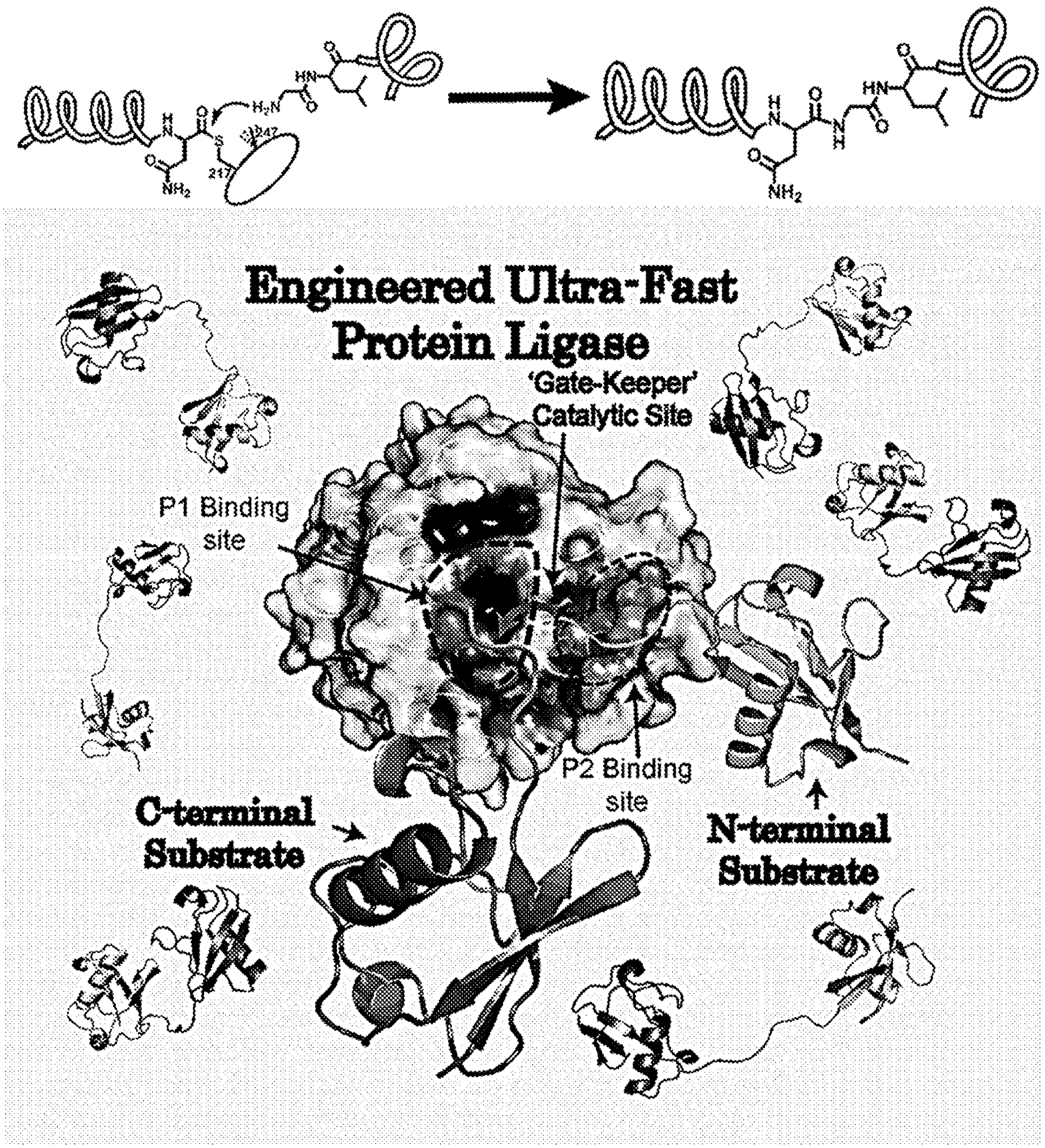

Crystals of OaAEP1 diffracting to a resolution of 2.56 Å at a 3$^{rd}$ generation synchrotron source were obtained (Table 1 and FIGS. 3A-3F). Although a OaAEP1 heterodimer was used as starting material, the crystal structure revealed a homo-dimer where both N-terminal $(His)_6$ tag and Ubiquitin fusion protein as well as the signal peptide sequence had been released from the two monomers present in the asymmetric unit, suggesting N-terminal proteolysis during crystallization (FIG. 3A and FIG. 3D). The OaAEP1 dimer is stabilized by intermolecular interactions between the two cap domains (FIG. 3D). This is in agreement with SEC analysis (FIG. 2C) showing that the pre-activated form of the enzyme containing the cap region is dimeric at neutral pH, while the activated form, which is devoid of cap, is monomeric. Accordingly, SDS PAGE of dissolved OaAEP1 crystals (FIG. 2B) revealed the presence of both the enzymatic core and the C-terminal pro-domain with a total Mr of approximately 49.7 kDa, supporting the hypothesis that the crystallized enzyme is in an immature form. The OaAEP1 core is formed by a 6-stranded β-sheet surrounded by six α-helices at its periphery (Dall, E., et al., Angew Chem Int Ed Engl, 2015. 54(10): p. 2917-21; Dall, E. and H. Brandstetter, Proc Natl Acad Sci USA, 2013. 110(27): p. 10940-5; Zhao, L., et al., Cell Res, 2014. 24(3): p. 344-58). An overall view of the structure shown in FIG. 3A reveals that the α-helical cap domain (spanning residues 347-474) entirely covers the catalytic cleft and suggests that release of the cap is required to grant access to peptide or protein substrates. The OaAEP1 catalytic site contains several residues present in other AEPs including the Cys217-His175 catalytic dyad (Cys189-His148 in hlegum) and His73-Asp174 that superimpose with His45-Asp147 of hlegum bound to cystatin E (PDB code 4N6O) (FIGS. 4A-4D). A clear difference captured here between the zymogenic forms of hlegum (PDB code: 4NOK) and OaAEP1 resides within the linker region: in the case of the prolegumain structure, the linker is short and well ordered, whilst it is long and flexible in the present OaAEP1 structure (FIG. 3A): no electron density was present for the 19 residues between 325 to 343, although this segment is present in the crystallized protein (FIG. 2B).

TABLE 1

Data collection and refinement statistics

| | oAEP1b |
|---|---|
| Resolution range (Å) | 71.72-2.56 (2.70-2.56)* |
| Space group | C2 |
| Unit cell dimensions a, b, c (Å) | 145.73 70.21 118.28 |
| Angles α, β, γ (°) | 90 117.14 90 |
| Measured reflections | 104,721 (14,189) |
| Unique reflections | 34,420 (5,029) |
| Multiplicity | 3.0 (2.8) |
| Completeness (%) | 99.7 (99.6) |
| Mean I/sigma(I) | 7.0 (1.7) |
| R-merge[a] | 0.095 (0.700) |
| R-pim[b] | 0.065 (0.501) |
| R-work[c] | 0.186 (0.212) |
| R-free[d] | 0.221 (0.212) |
| Number of non-hydrogen atoms | 6,498 |
| macromolecules | 6,200 |
| water | 298 |
| Protein residues | 851 |
| RMS (bonds, Å) | 0.010 |

TABLE 1-continued

| Data collection and refinement statistics | |
|---|---|
| | oAEP1b |
| RMS (angles, °) | 1.19 |
| Ramachandran plot (%) | |
| favoured | 93.8 |
| allowed | 5.1 |
| outliers | 1.1 |
| Clash score | 6.37 |
| Average B-factor | |
| Monomer A,B | 71.8, 66.1 |
| solvent | 62.0 |

*The numbers in parentheses refer to the last (highest) resolution shell.

[a] $R_{merge} = \Sigma|I_j - \langle I \rangle|/\Sigma I_j$, where $I_j$ is the intensity of an individual reflection, and $\langle I \rangle$ is the average intensity of that reflection.

$$^{b}R_{pim} = \frac{\sum_{hkl}\sqrt{\frac{1}{n-1}}\sum_{j=1}^{n}|I_{hkl,j} - \langle I_{hkl}\rangle|}{\sum_{hkl}\sum_{j} I_{hkl,j}}$$

[c] $R_{work} = \Sigma||F_o - F_c||/\Sigma|F_c|$, where $F_o$ denotes the observed structure factor amplitude, and $F_c$ the structure factor amplitude calculated from the model.

[d] $R_{free}$ is as for $R_{work}$ but calculated with 5% (3044) of randomly chosen reflections omitted from the refinement.

Figures 4A, 4B:
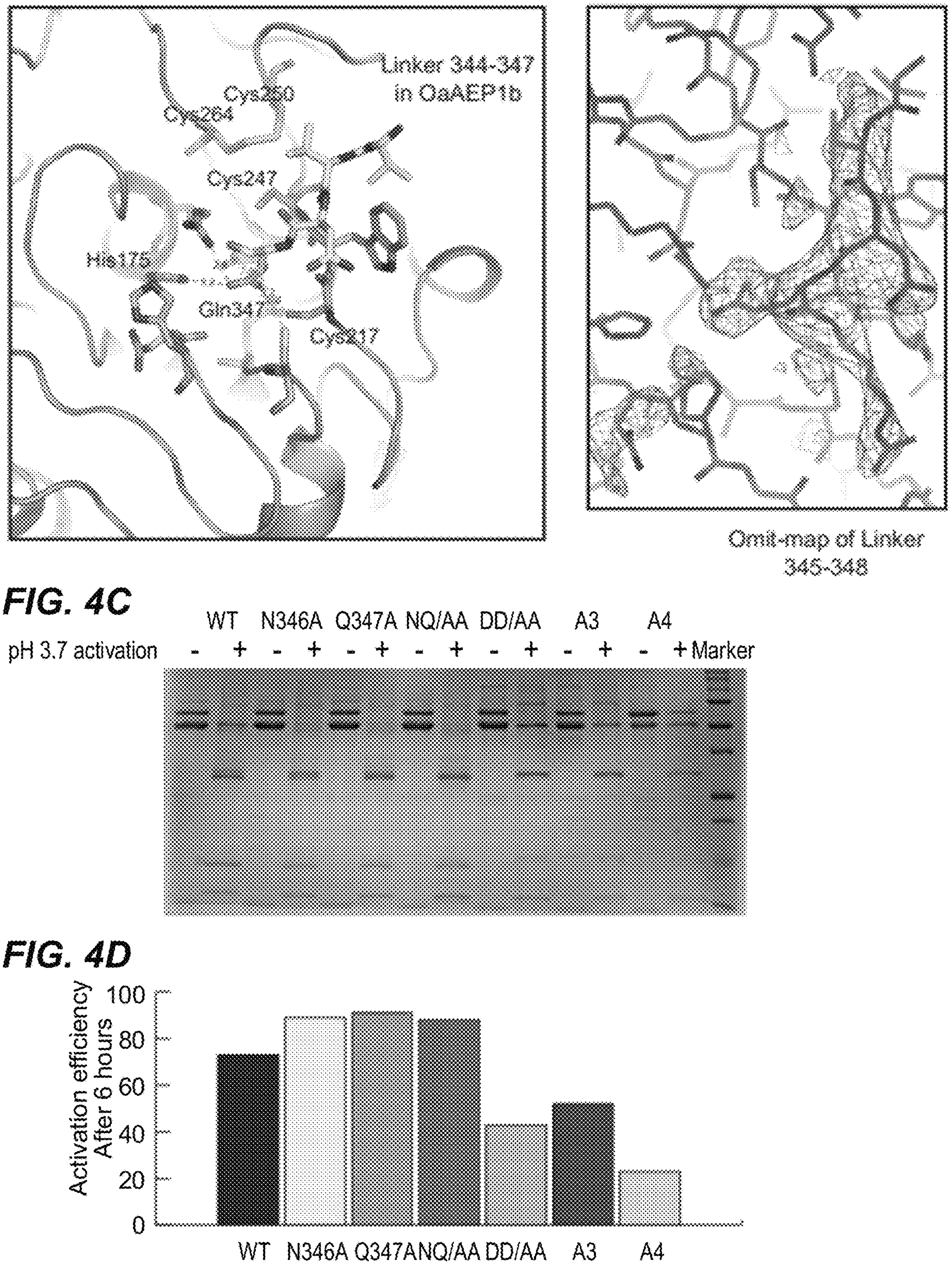

While residues 325-343 of the linker region are not visible in the electron density map due to their flexibility, residues Val344-Val345-Asn346-Gln347 are trapped at the interface between the cap and the core domain (FIG. 3C and FIG. 4A). Remarkably, their orientation closely overlaps with the Ac-Tyr-Val-Ala-Asp-chlorometylketone inhibitor that was covalently linked to the catalytic Cys189 of hlegum (FIG. 3E, PDB code: 4AWA) (Dall, E. and H. Brandstetter, Proc Natl Acad Sci USA, 2013. 110(27): p. 10940-5. ). Here however, residue Gln347 penetrates deeply into the S1 pocket such that its amide group occupies the position of the carboxylic group of the Asp residue in the Ac-Tyr-Val-Ala-Asp-CMK protease inhibitor that was covalently bound to hlegum and forming several interactions with the surrounding active site residues (FIG. 4A and FIG. 4B). Thus the present crystal structure can serve as a useful model to picture a pre-ligation conformation, with linker residues 344-347 mimicking a N-terminal substrate acceptor bound to the active site.

Although in other AEPs, Asx is the most favored residue for processing at the P1 position, the carbonyl group of Gln347 lies at a distance of 5.2 Å from the attacking Cys217 sulfur center, suggesting that the segment 346-351 of the pro-protein might contain auto-cleavage sites used during maturation. Since the crystallization conditions are compatible with OaAEP1 activation, the present crystal structure is likely to have captured one of the conformational states occurring along the activation pathway. To determine whether Gln347 belongs to the segment recognized and cleaved during self-activation, mutagenesis experiments targeting region 346-351 of the OaAEP1 protein were performed (FIG. 4C). The role of Gln347 in OaAEP1 auto-activation was particularly assessed by mutating this residue to Ala, and whether enzyme activation was abolished was examined. Only little impact was found on the mutant enzyme activation (FIG. 4C). Residues Asn346, Asp349 and Asp351 that are next to Gln347 were then targeted. While the two OaAEP1 double mutants Asn346Ala-Gln347Ala and Asp349Ala-Asp351Ala and the Asn346Ala-Asp349Ala-Asp351Ala triple mutant can still be activated, the Asn346Ala-Gln347Ala-Asp349Ala-Asp351Ala had the most significantly impaired auto-activation activity (lane "A4" in FIG. 4C). Importantly, activation of the four-Ala mutant could not be rescued in trans when wild type enzyme was added to the reaction mixture. Thus, trans-activation requires the presence of at least one of the four Asx/Gln residues (with a slight preference for Asp349 or Asp351) found in this segment of the linker. Taken together, these data suggest that the present crystal structure represents an intermediate conformational state during which the linker region is trapped at the catalytic site, mimicking a substrate-bound pre-ligation complex.

The peptide cyclization activity of mature OaAEP1 was then analyzed using MS and the peptide substrate "GLPVSTKPVATRNGL" (SEQ ID NO: 18) (FIG. 5A). The turn-over rate ($k_{cat}$) for OaAEP1 is 0.052 $s^{-1}$, a value in good agreement with the previous report (Harris, K. S., et al., Nat Commun, 2015. 6: p. 10199). Likewise, the cyclization activity of butelase 1 extracted from plant was measured using the 15 residues peptide "GLPVSTKPVATRNHV" (SEQ ID NO: 19) (FIG. 5A) leading to a $k_{cat}$ about 90 times faster than OaAEP1b.

Figure 10:
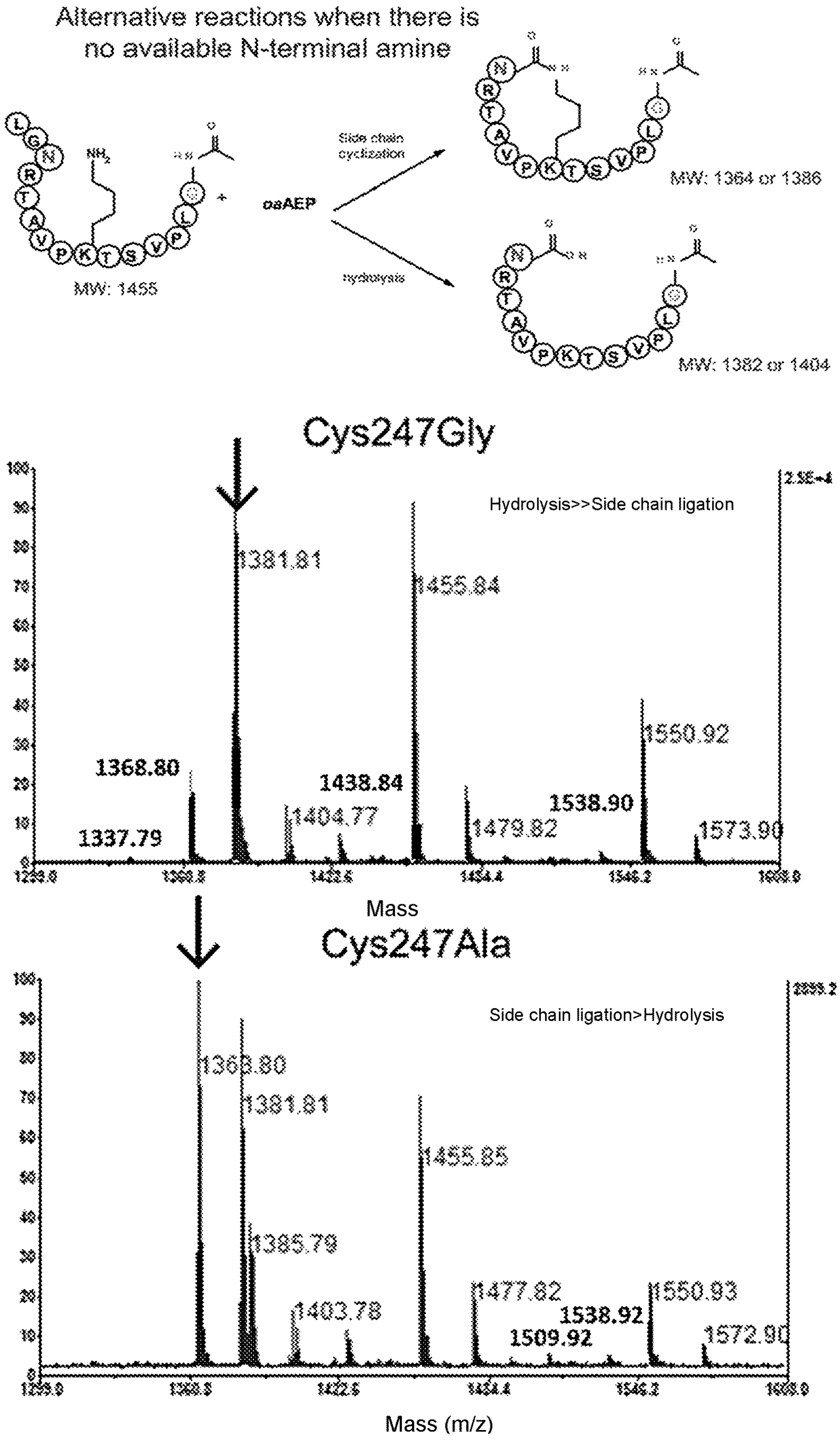
FIG. 10 shows the potential side product of the ligation reaction. If there is no available N-terminal amine, side chain ligation and proteolysis could happen in Cys247Gly and Cys247Ala mutants. The smaller size of the side chain of Cys247Gly mutant permitted water molecules to participate in the reaction and results proteolysis.

The pre-ligation conformation of OaAEP1 captured in the present structure was then analyzed to identify several key features that could differentiate an AEP protease from an AEP-like ligase. A side-by-side comparison with a previously reported proteolytic AEP-inhibitor complex (PDB code: 4AWA) revealed interesting structural features unique to AEP-like ligases. In contrast to AEP proteases, the surface of OaAEP1 facing the catalytic Cys217 appears to be more widely open. Three cysteine residues (Cys247, Cys250, Cys264) are aligned along a shallow cleft at the surface of the enzyme (FIG. 3C and FIG. 3E). Unlike the surface of AEP proteases that contains several bulges, both butelase 1 (using a homology model based on OaAEP1b) and OaAEP1 have residues with smaller side-chains along this patch. A disulfide bond is formed between Cys250 and Cys264, which are conserved in AEP-like ligases butelase 1 and OaAEP1b. This covalent bond is likely to stabilize the local structure and provide an adequate surface allowing the approach of an N-terminal amine incoming group. Conversely, the corresponding surface patch of AEP proteases (PDB: 4AWA) is lined with residues having bulky side-chains like Tyr (FIG. 3E) blocking this channel. It was therefore hypothesized that residue Cys247 which is located at the extremity of the substrate channel is likely to function as a final nucleophile filter (or "gate-keeper"), allowing attack from the N-terminal amine to complete the ligation reaction. To test the impact of various side chains on ligase behavior at the "gate keeper" position, a series of point mutagenesis was performed whereby Cys247 was mutated into Gly, Ala, Val, Ser, Thr, Met, Leu and Ile (FIGS. 5A-5D). The activity of the corresponding mutant proteins revealed that the size of the side chain indeed plays a critical role on ligase activity. Remarkably, the Cys247Ala mutant displayed significantly improved enzymatic properties compared to WT OaAEP1 (FIG. 5D). This phenotype was attribute to the presence of a smaller side chain that is more appropriate to accommodate an incoming amine group, while the Cys247Gly mutation destabilizes the local conformation and negatively affects the ligase activity. Further investigations showed that Cys247Gly catalyzes peptide hydrolysis as alternative reaction, if the available N-terminal amine group was acetylated (FIG. 10). While in the case of Cys247Ala mutant, side chain ligation is more preferred if no available N-terminal amine is present, Ala is less hydrophilic which disfavors water entering the catalytic patch causing hydrolysis of the intermediate thio-ester bond.

When the N-terminal amine is not protected, backbone ligation is much more favored than any of the alternative reactions.

Figure 6A:
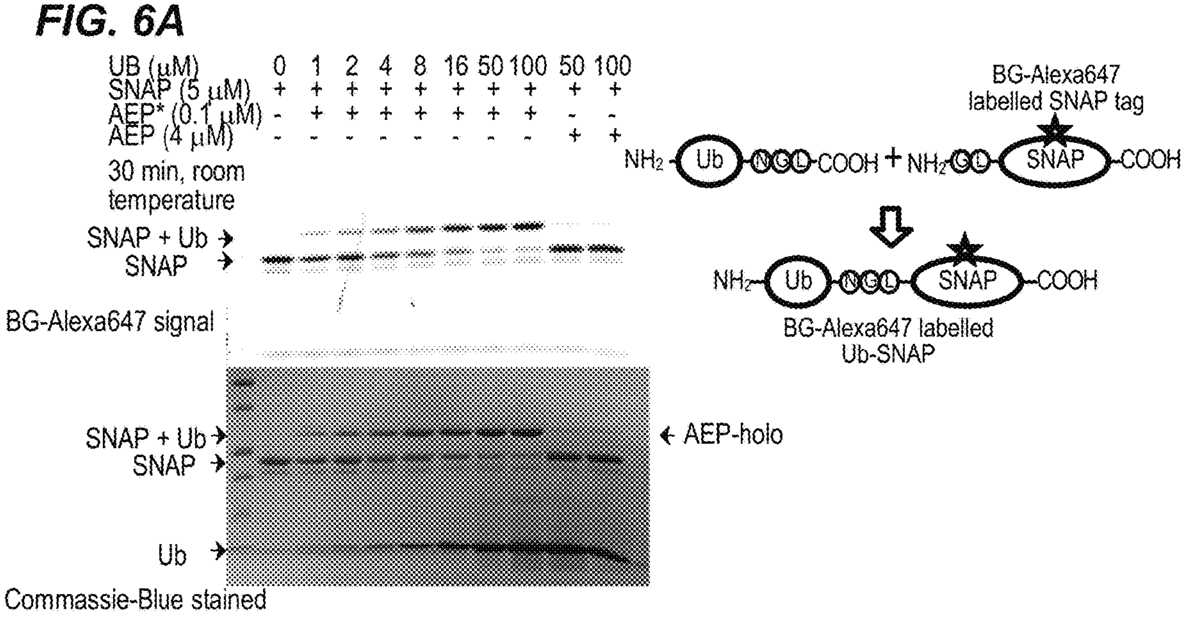
FIGS. 6A and 6B show protein ligase activity of Cys247Ala.
Figure 6B:
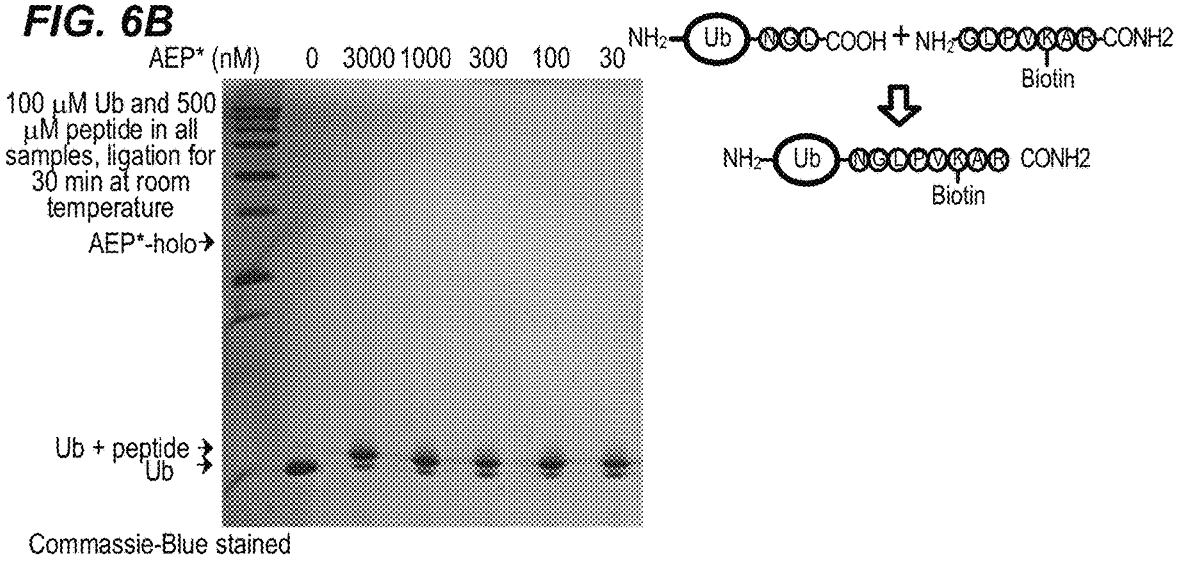
Figure 8A:
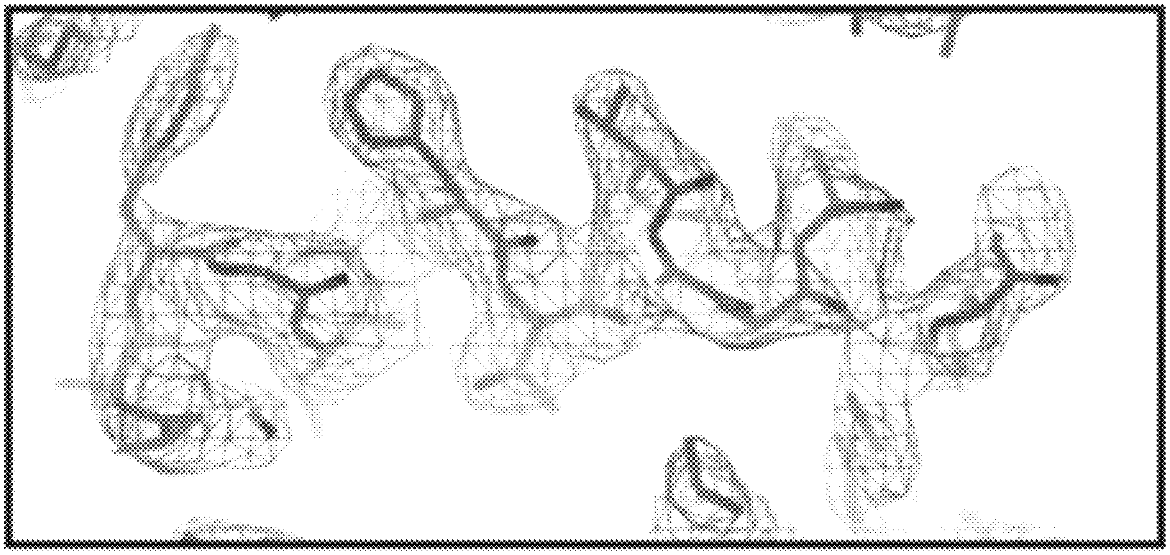
FIGS. 8A and 8B show the 2FO-FC electron density map, highlighting the good fitting of the model.
Figure 8B:
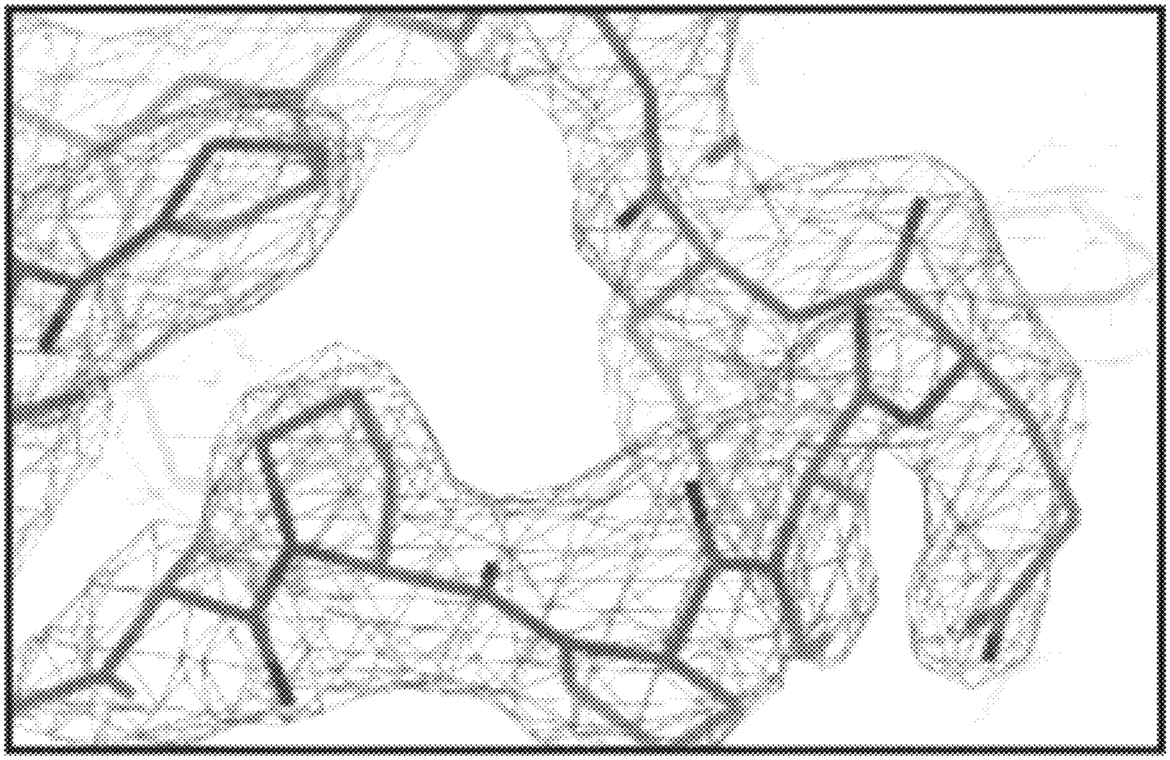
Figure 9A:
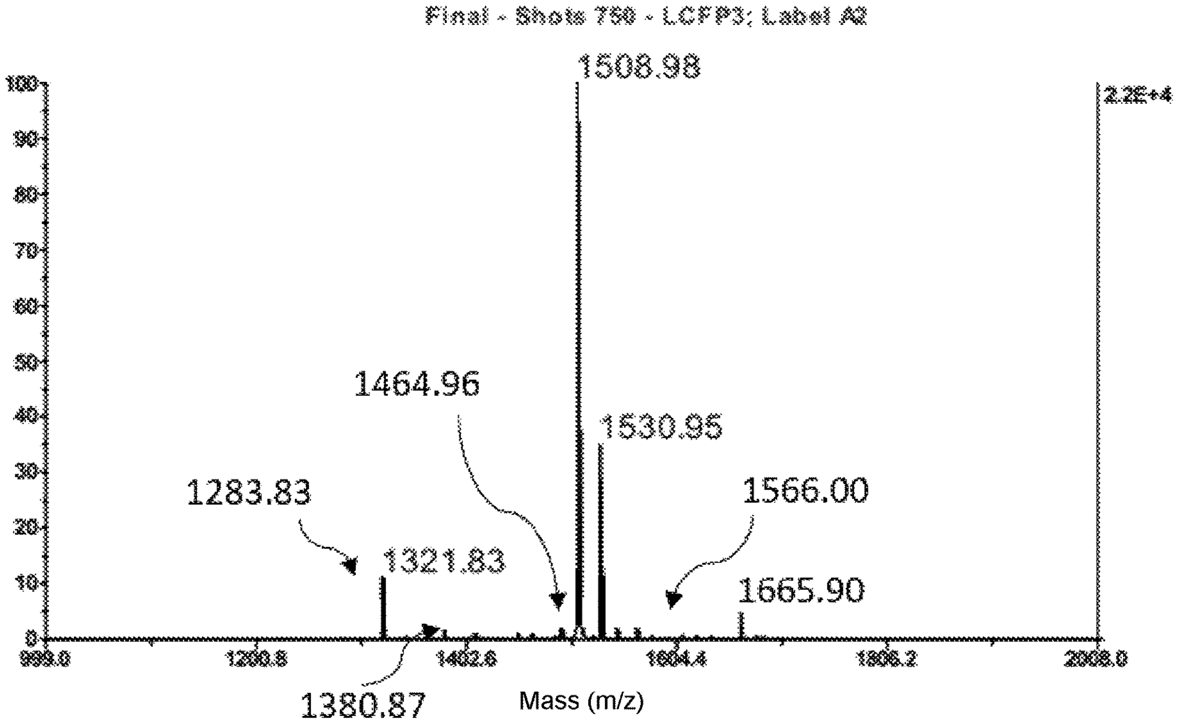
FIGS. 9A-9P show the raw mass-spectrometry results of Gate-Keeper mutants.
Figure 9B:
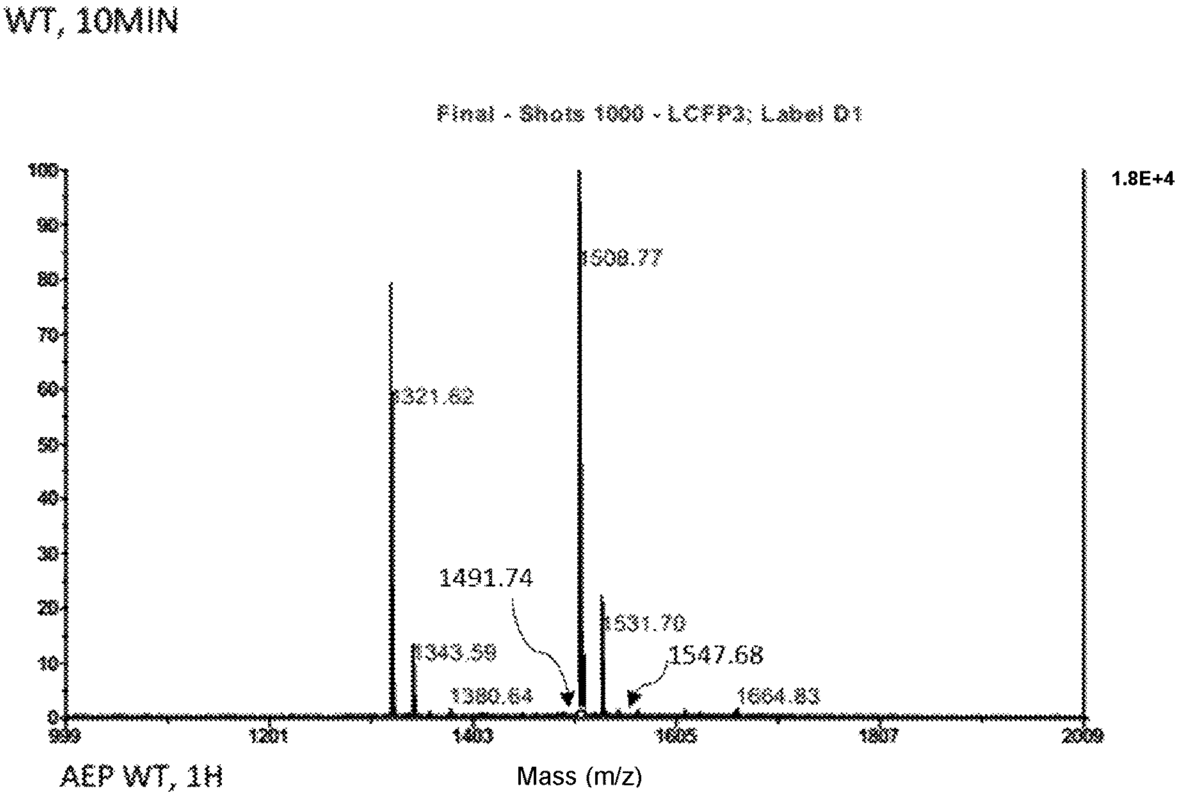
Figure 9C:
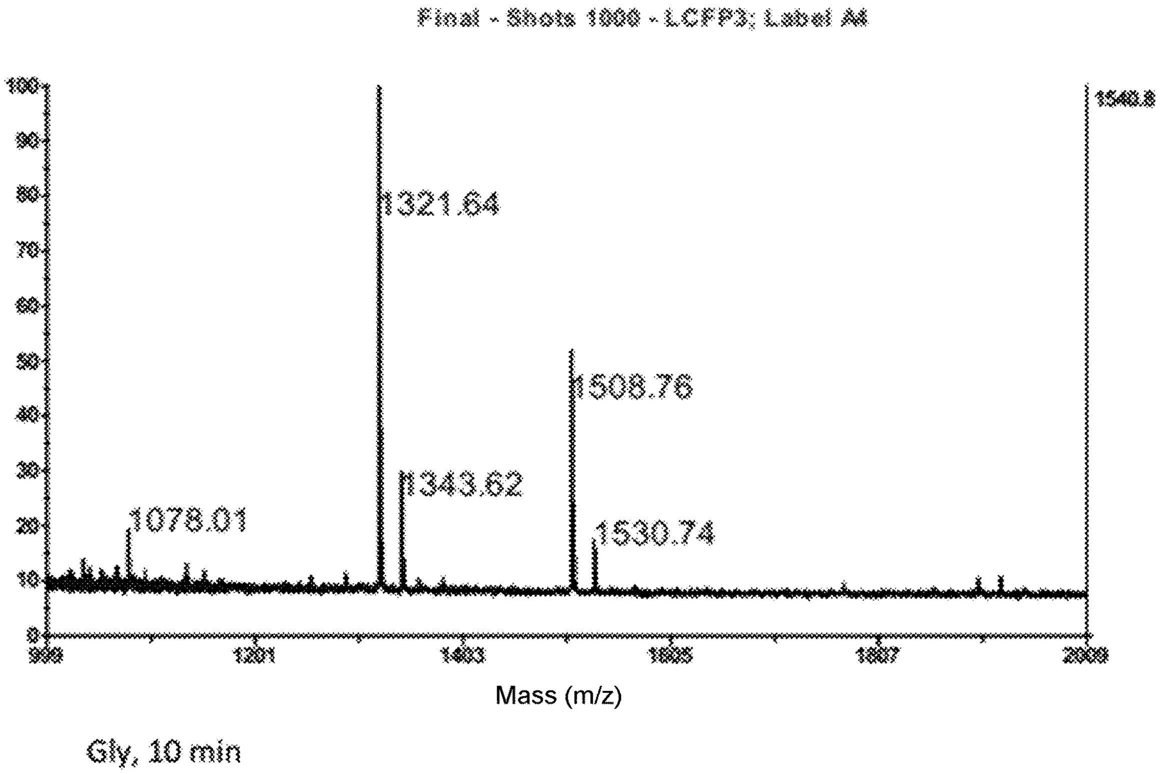
Figure 9D:
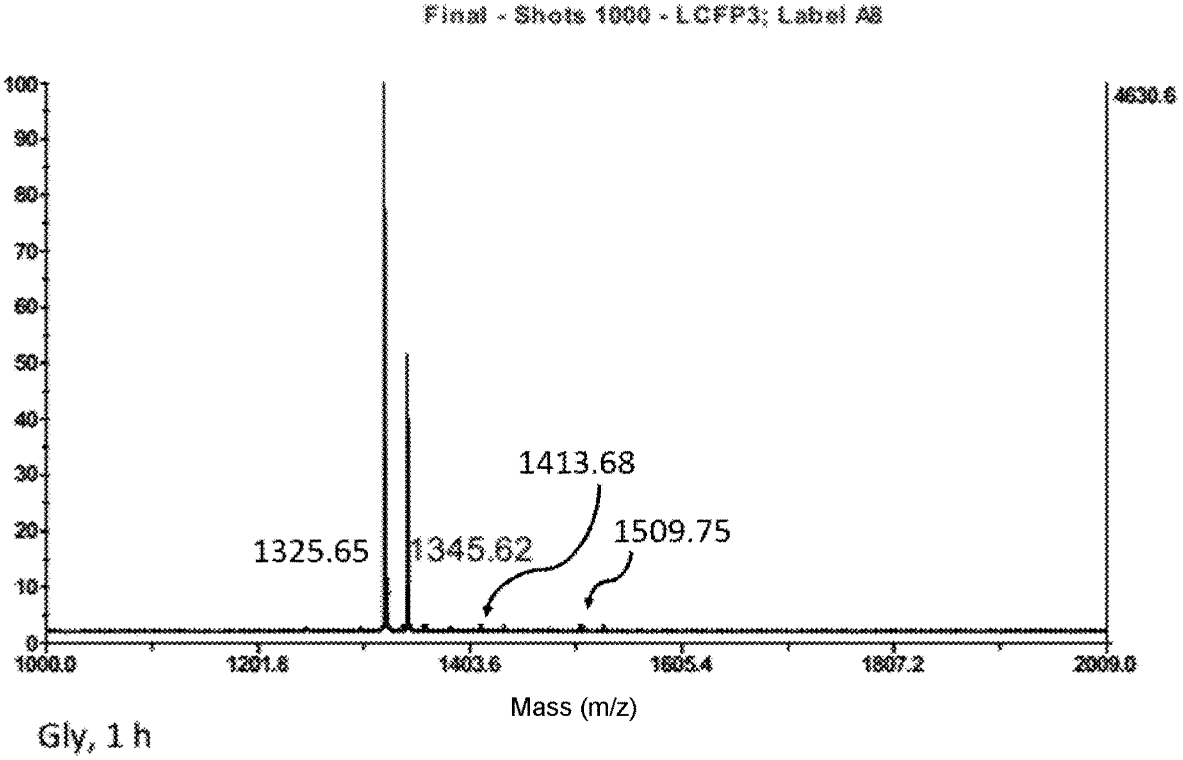
Figure 9E:
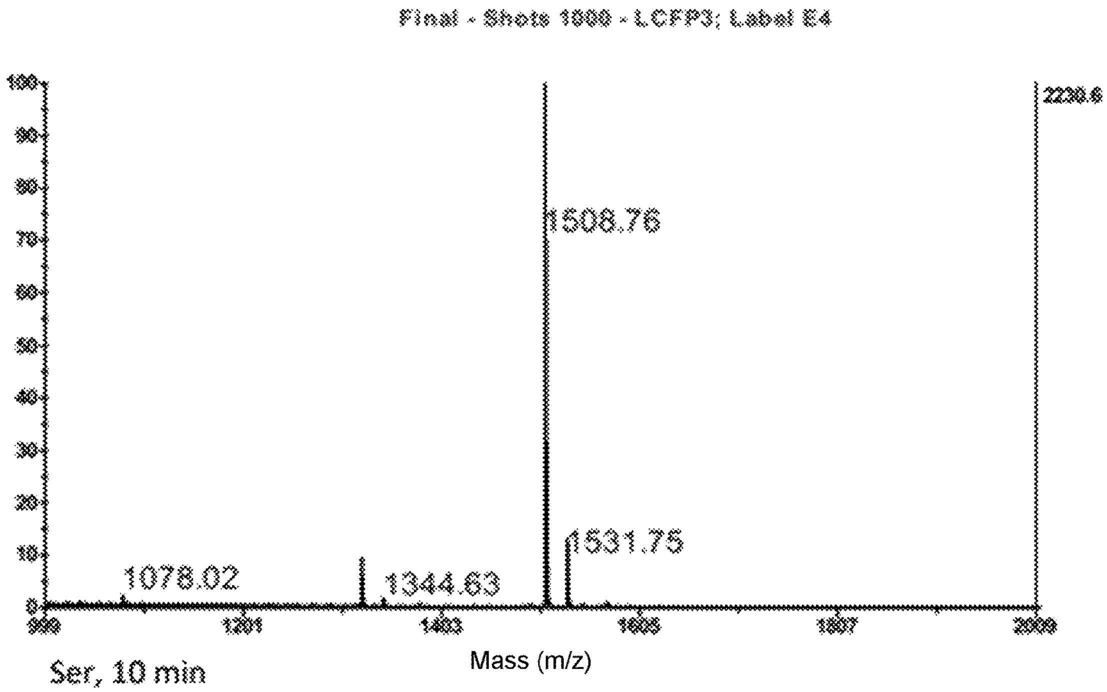
Figure 9F:
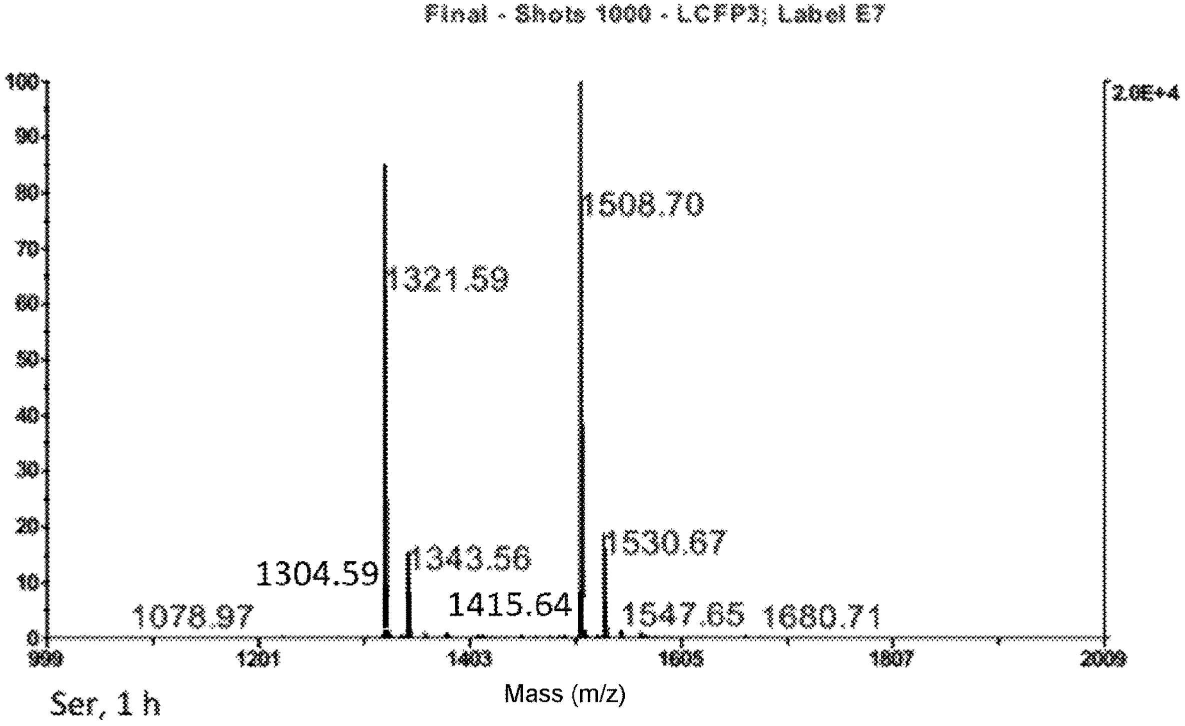
Figure 9G:
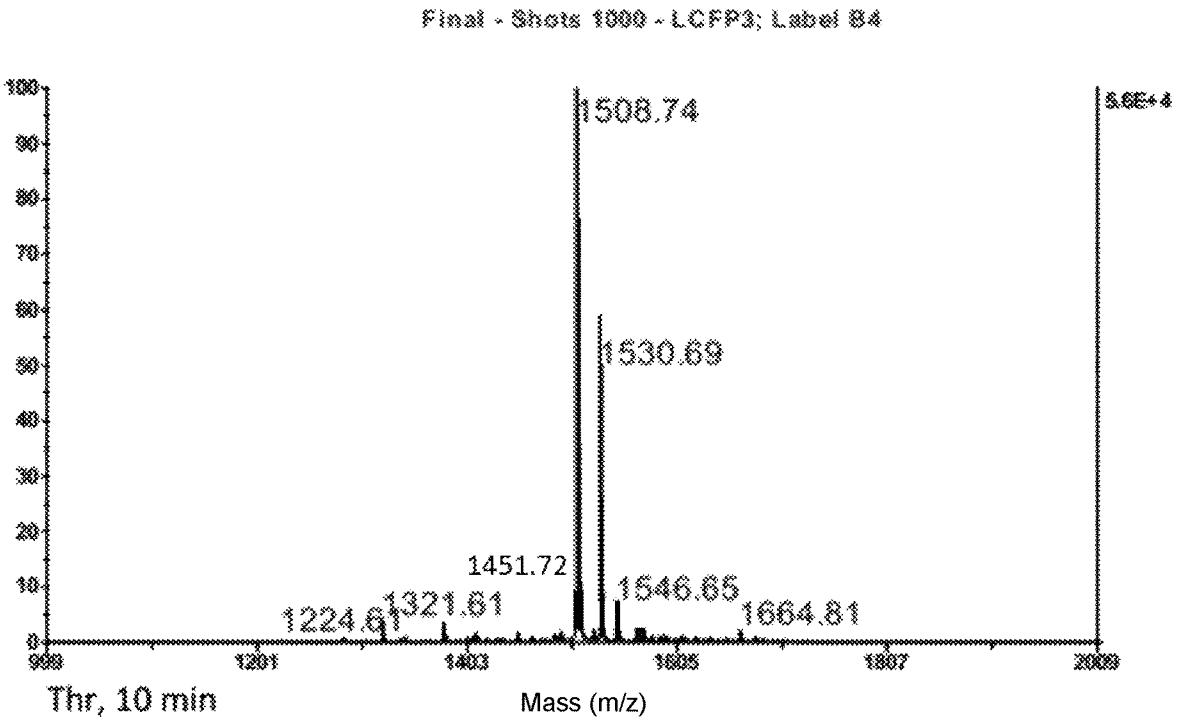
Figure 9H:
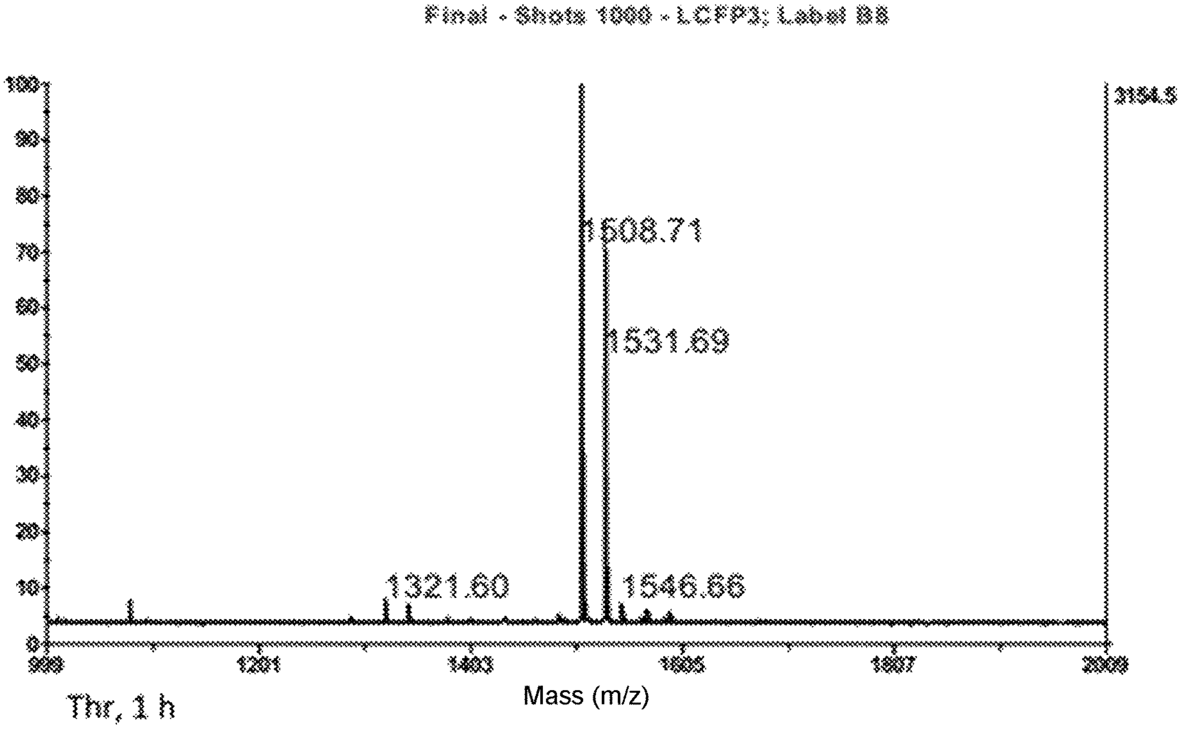
Figure 9I:
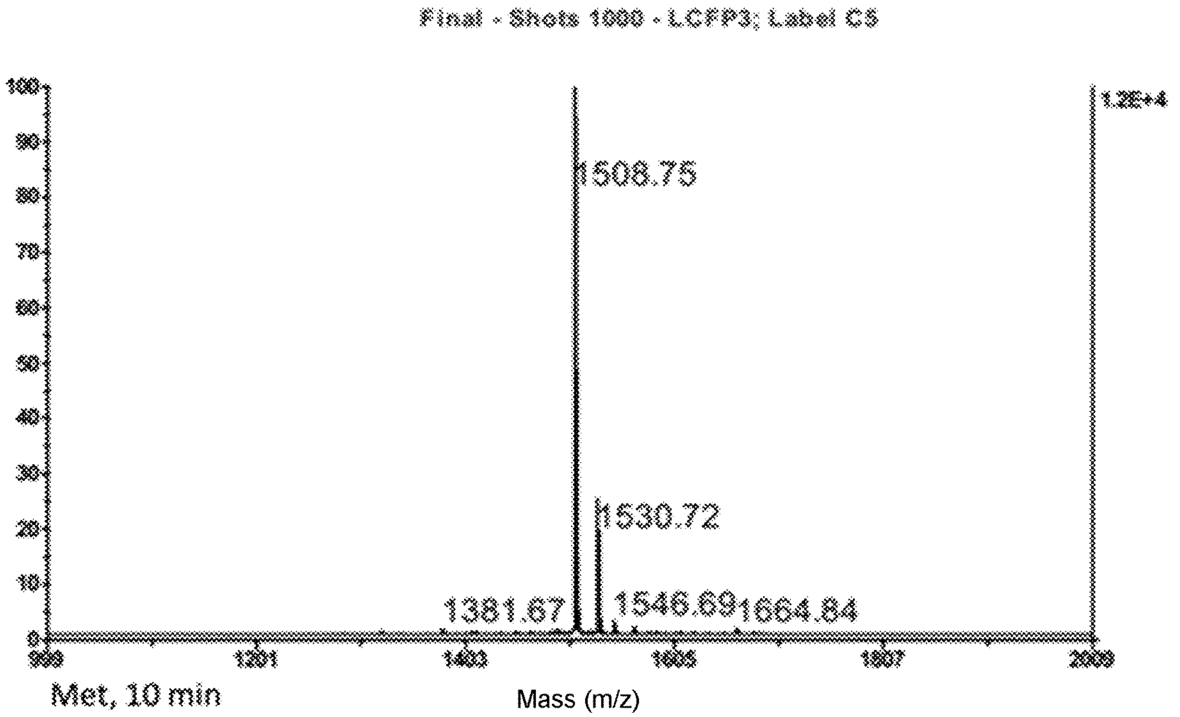
Figure 9J:
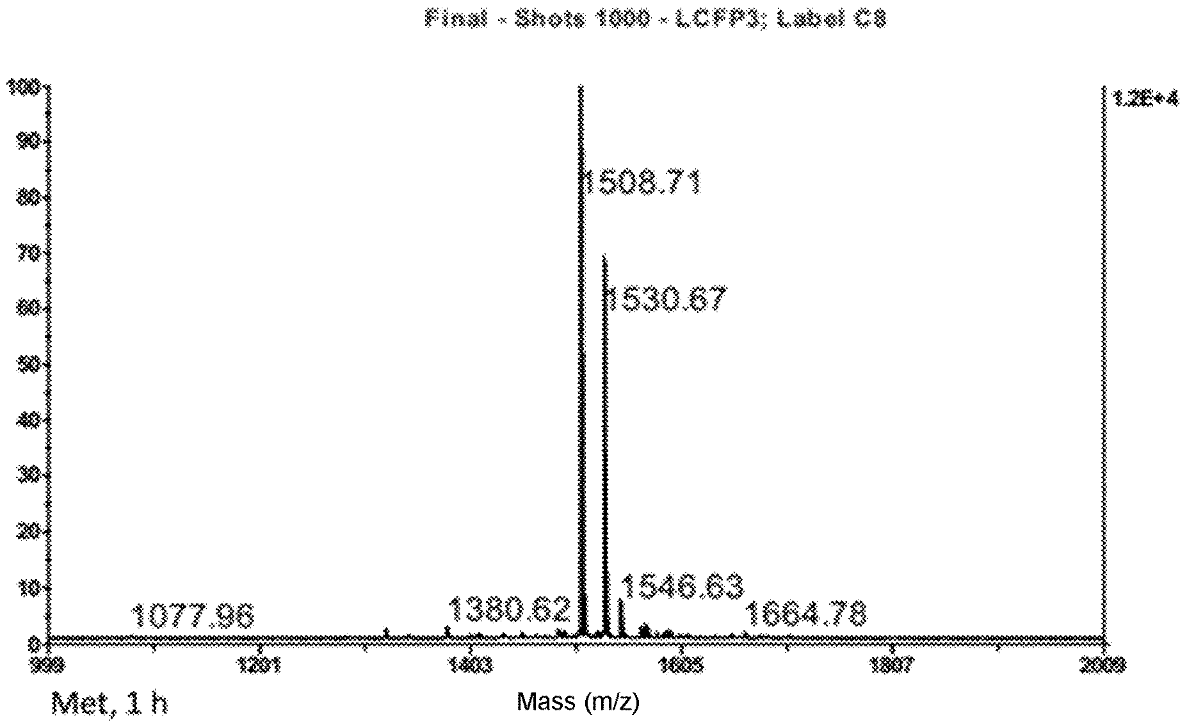
Figure 9K:
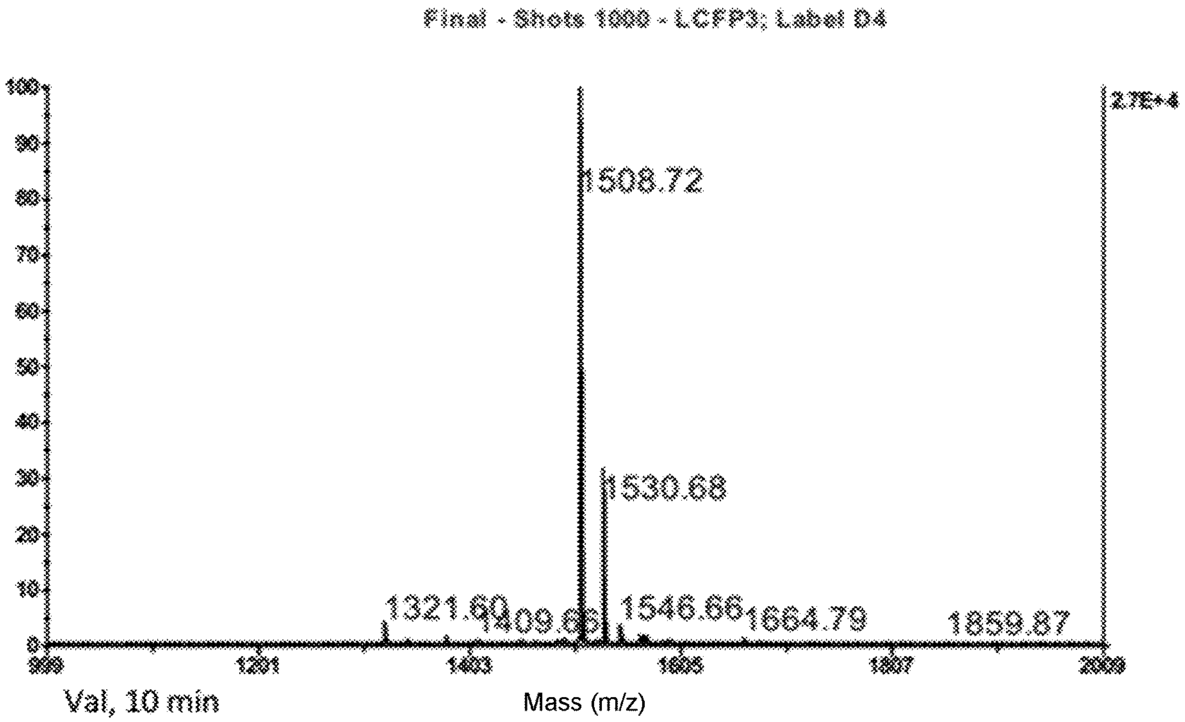
Figure 9L:
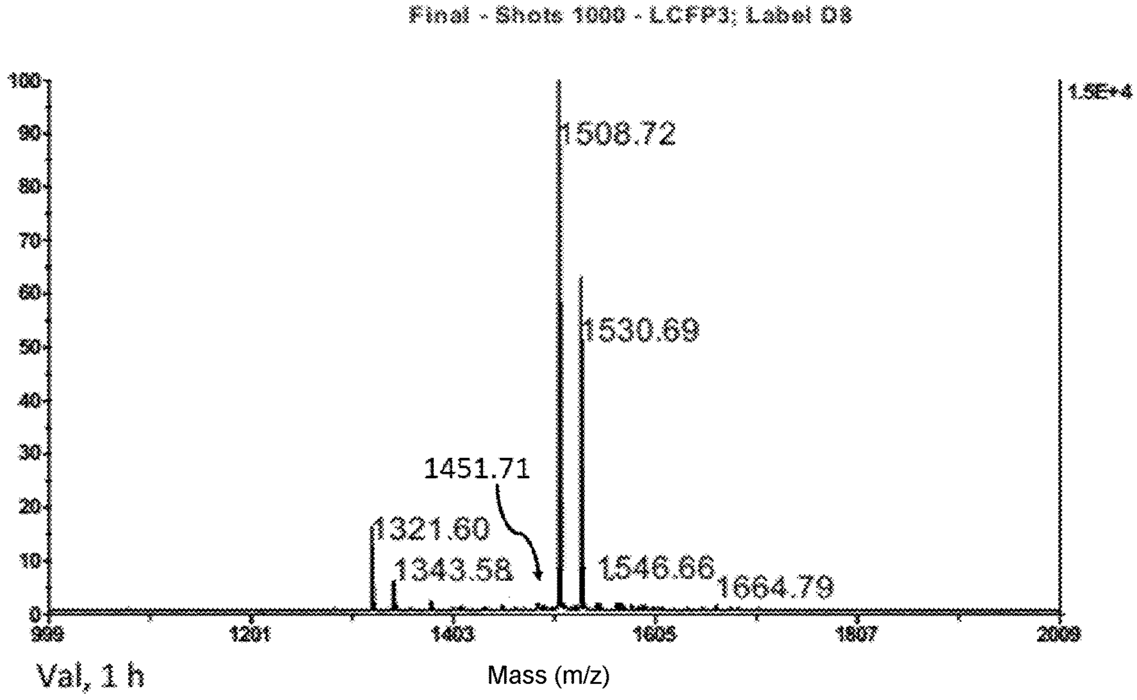
Figure 9M:
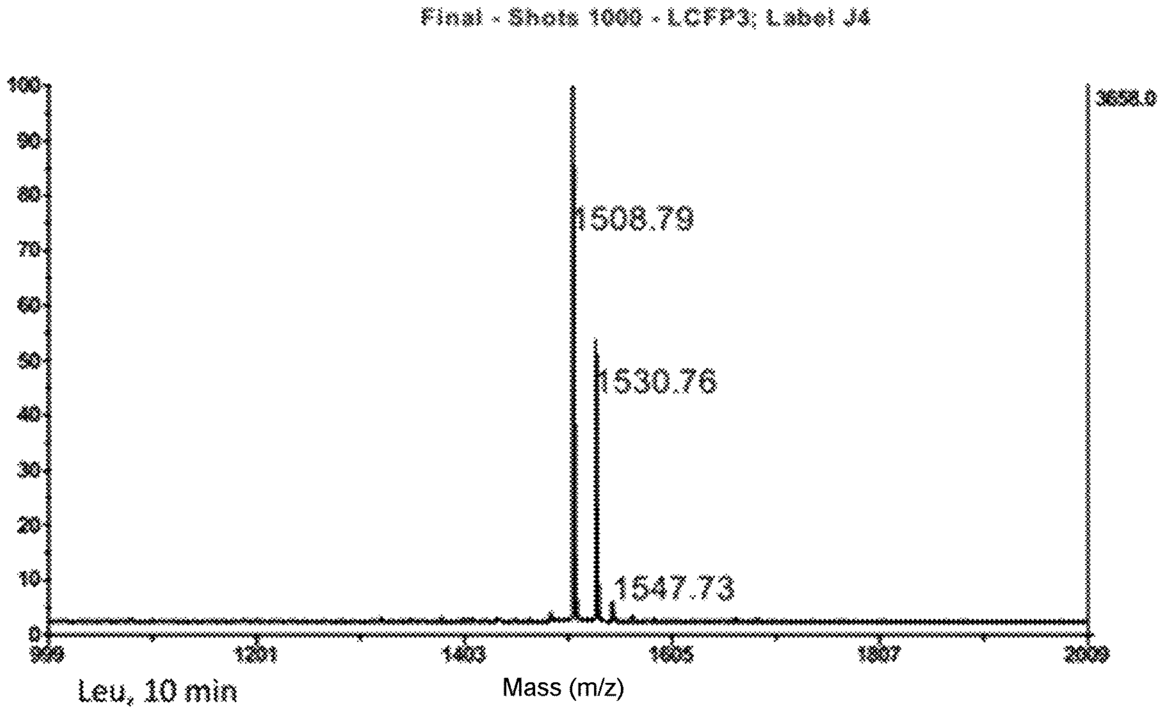
Figure 9N:
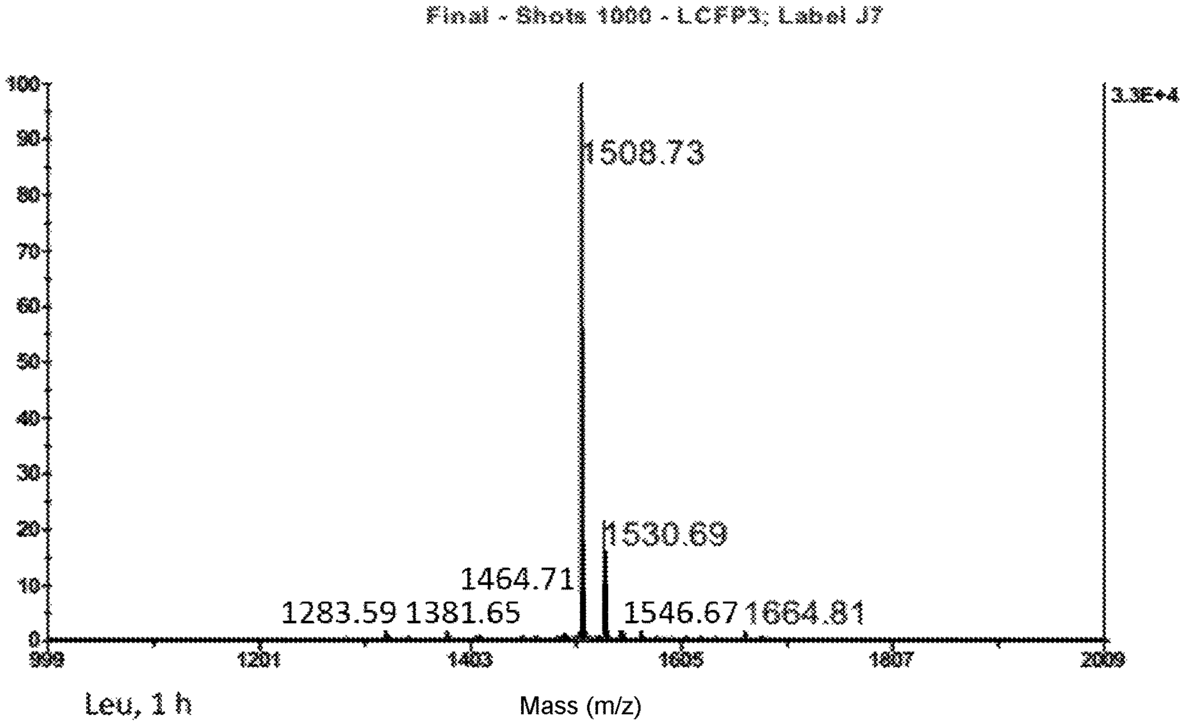
Figure 9O:
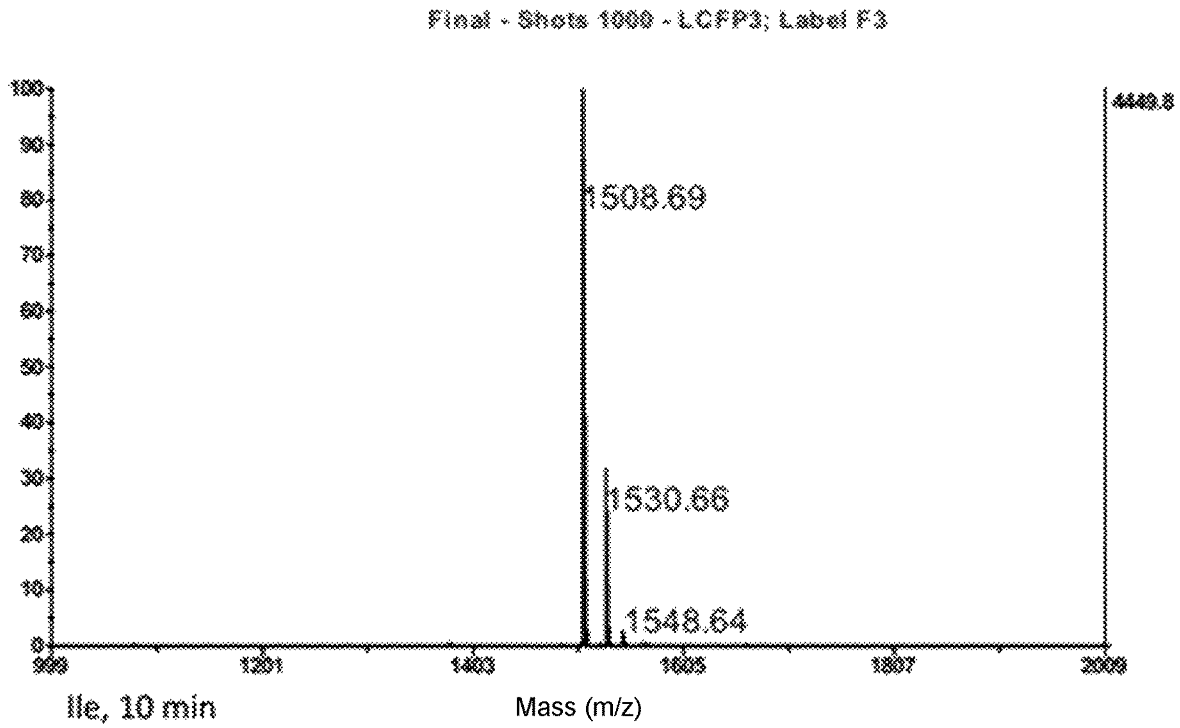
Figure 9P:
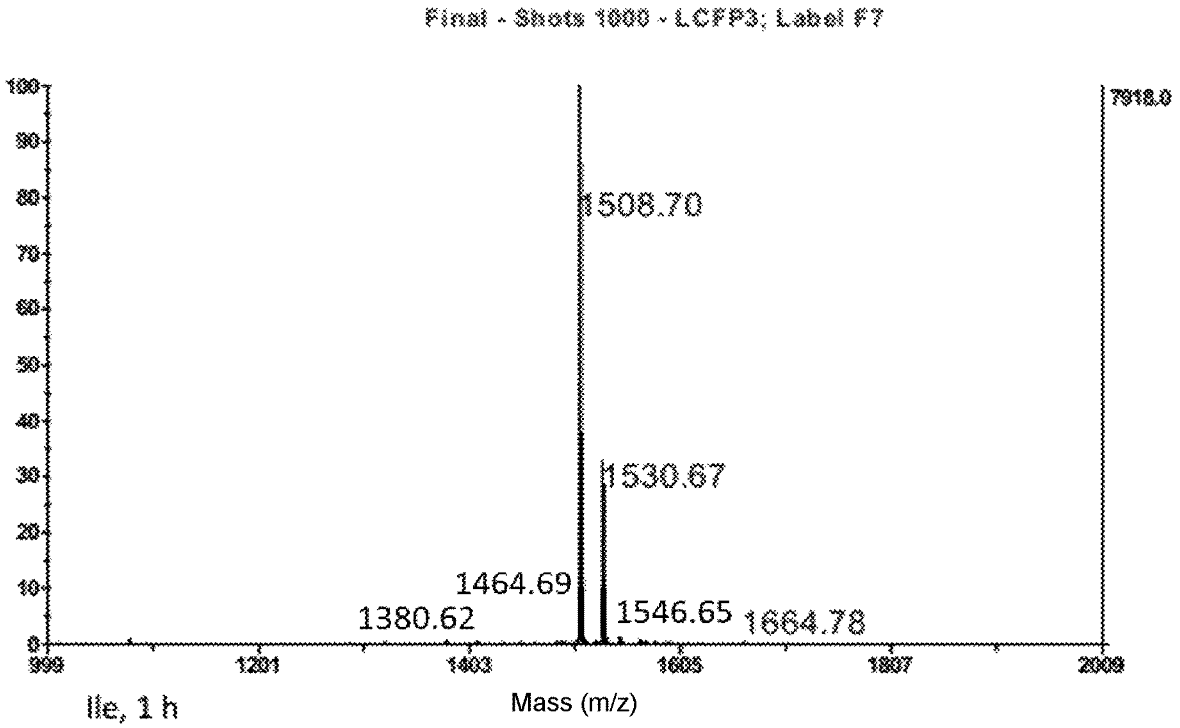

Remarkably Cys247Ala demonstrated improved enzymatic properties over the parent wild-type OaAEP1 protein: its $k_{cat}$ approximately 160 times higher than WT OaAEP1b, makes it an attractive tool for a variety of challenging protein engineering and labeling applications. The ability of Cys247Ala to ligate ubiquitin with a peptide was first tested. The three residues "Asn-Gly-Leu" were added to the C-terminus of ubiquitin to make it recognizable by Cys247Ala. Another peptide having N-terminal residues GlyLeu was used as the add-on component. At a protein:peptide molar ratio of 1:5, Cys247Ala catalyzed the ligation of more than 90% ubiquitin with the peptide within 10 min (FIG. 6A and FIG. 6B). An amount of 30 nM of Cys247Ala was enough for the reaction compared to 10-30 μM of sortase A typically required to perform productive ligations. To further demonstrate the potential of Cys247Ala, ligations between two well-folded proteins were also tested. Ubiquitin having the same "Asn-Gly-Leu" modification at its C-terminal end and a N-terminal modified SNAP (NEB) tag protein were used as substrates. Using 5 μM of SNAP tag protein and 8 ubiquitin, 100 nM Cys247Ala was able to ligate more than 60% of the individual substrate proteins into a ligated single polypeptide product, indicating that the catalyzed protein ligation is highly efficient and irreversible (FIG. 6A and FIG. 6B). Protein ligation can be performed within minutes at neutral pH and at room temperature. Remarkably, the efficiency of Cys247Ala to catalyze the ligation of two folded proteins is comparable to its ability to ligate one protein with a peptide, suggesting that its open binding site can accommodate two bulky protein substrates without hindering the ligation process. Control ligation experiments showed that protein ligation activity could only be observed in the presence of the Cys247Ala protein, but not with the OaAEP1 wild type construct (FIG. 6A and FIG. 6B). This further demonstrated the important role played by the gatekeeper residue in regulating access to protein substrate.

Both sortase A and butelase 1 have been used to perform peptide ligations. However, both enzymes suffered from several disadvantages. Sortase A requires $Ca^{2+}$, is slow and recognizes a longer—more flexible—C-terminal sequence (LPXTG). Although through extensive mutagenesis studies, several mutants were identified improving its kinetics, the catalysis was still quite inefficient in ligating two well-folded proteins (Chen, I., B. M. Don, and D. R. Liu, Proc Natl Acad Sci USA, 2011. 108(28): p. 11399-404). In contrast, butelase 1 extracted from plant, is extremely efficient and has a shorter recognition amino acids sequence (NHV) (Nguyen, G. K., et al., Nat Chem Biol, 2014. 10(9): p. 732-8). However, optimization and engineering of the recombinant construct of Butelase 1 still remains challenging because of the difficulty to produce an active recombinant enzyme. Here, to the knowledge of the inventors the first X-ray crystallographic structure of OaAEP1 was reported that can serve as a template to understand the family of plant AEP ligases and will facilitate the design of faster protein ligases with alternative substrate specificities. Our structure reveals the mode through which self-cleavage activation is achieved in AEP-like ligases and also points to key residues and structural features accounting for the functional divergence among AEP-like proteins: AEPs that act primarily as proteases lack the flat surface near the catalytic pocket conducive to ligation, while AEP-like proteins that are efficient ligases have a wide and open surface able to accommodate the incoming amine group. These structural observations led us to engineer a modified ligase Cys247Ala with improved biochemical properties, which can efficiently ligate proteins. Given its fast ligation catalytic kinetics, it is believed that the present Cys247Ala recombinant protein ligase can be employed to perform attractive biotechnological applications both for protein/peptide synthesis and specific protein labeling (Guimaraes, C. P., et al., Nat Protoc, 2013. 8(9): p. 1787-99; Swee, L. K., et al., Proc Natl Acad Sci USA, 2013. 110(4): p. 1428-33; Theile, C. S., et al., Nat Protoc, 2013. 8(9): p. 1800-7; Witte, M. D., et al., Nat Protoc, 2013. 8(9): p. 1808-19; Wagner, K., et al., Proc Natl Acad Sci USA, 2014. 111(47): p. 16820-5; Nguyen, G. K., et al., Angew Chem Int Ed Engl, 2015. 54(52): p. 15694-8; Nguyen, G. K., et al., J Am Chem Soc, 2015. 137(49): p. 15398-401).

Example 2: Quicklase OaAEP1 Homologues Identified by NCBI-BLAST

A Blast search of the amino acid sequence of SEQ ID NO:1 was carried out by submitting the sequence to the NCBI blast server using standard blast criteria. Top hits as displayed in FIGS. 12A and 12B were selected for sequence analysis. All of them were found to contain the conserved structural motif of residues 247-264 of OaAEP1b.

Example 3: AEP_C13CO4 (SEQ ID NO:8) is a Peptide Ligase Having the Activity of OaAEP1 Cys247Ala (SEQ ID NO:1)

Figure 13:
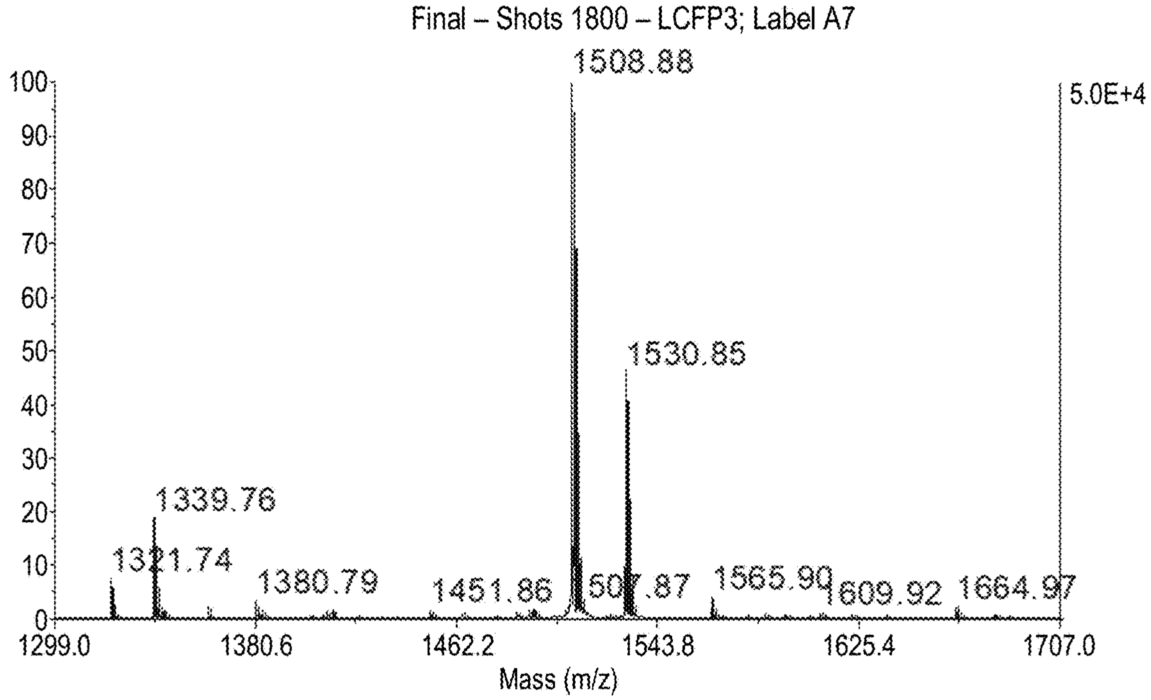
FIG. 13 shows that AEP_C13CO4 having the amino acid sequence set forth in SEQ ID NO:8 is a peptide ligase having the activity of OaAEP1 Cys247Ala (SEQ ID NO:1).
Figure 14B:
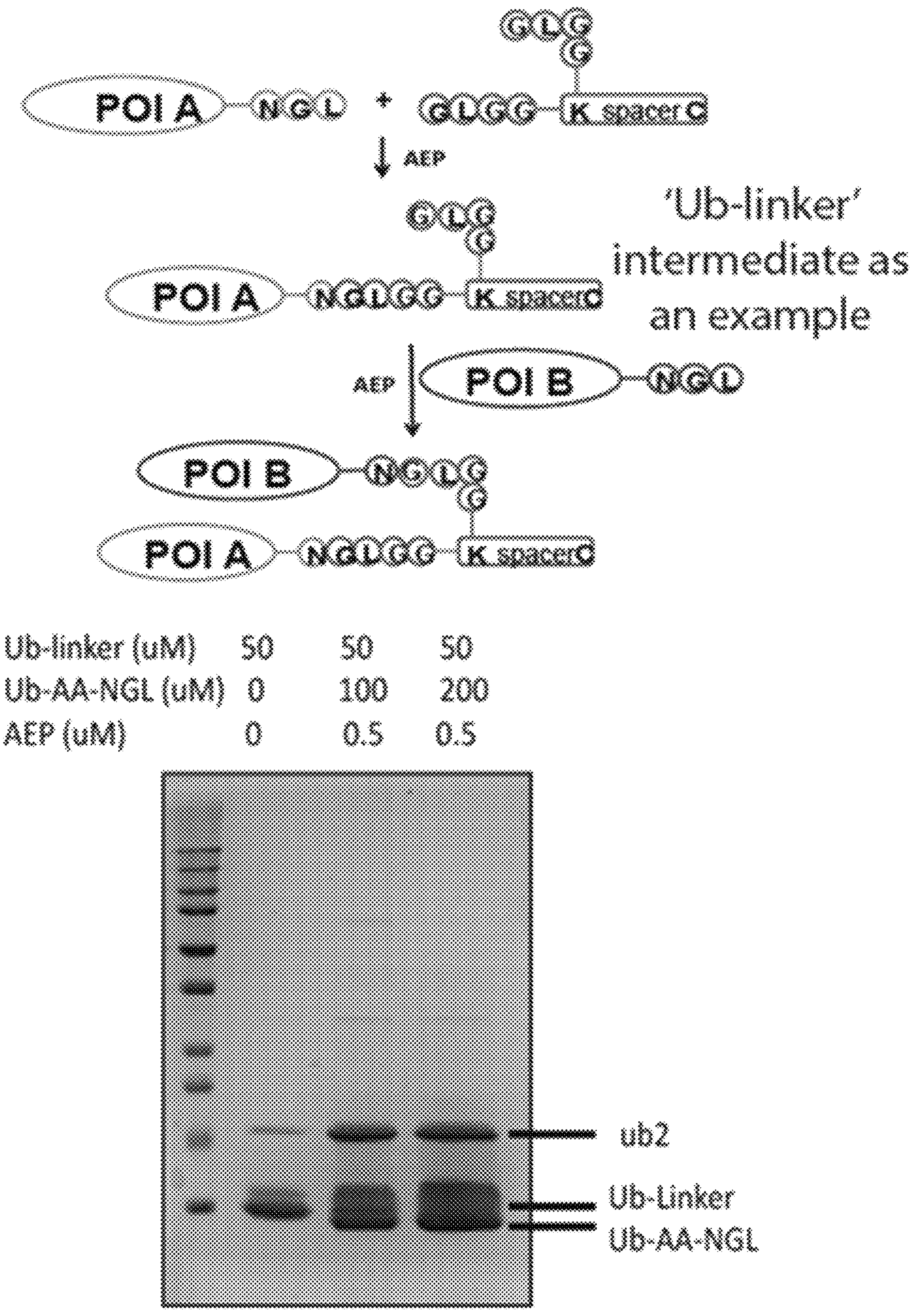
FIG. 14B shows schemes for scaffold-based two-step heterodimerization.
Figure 14C:
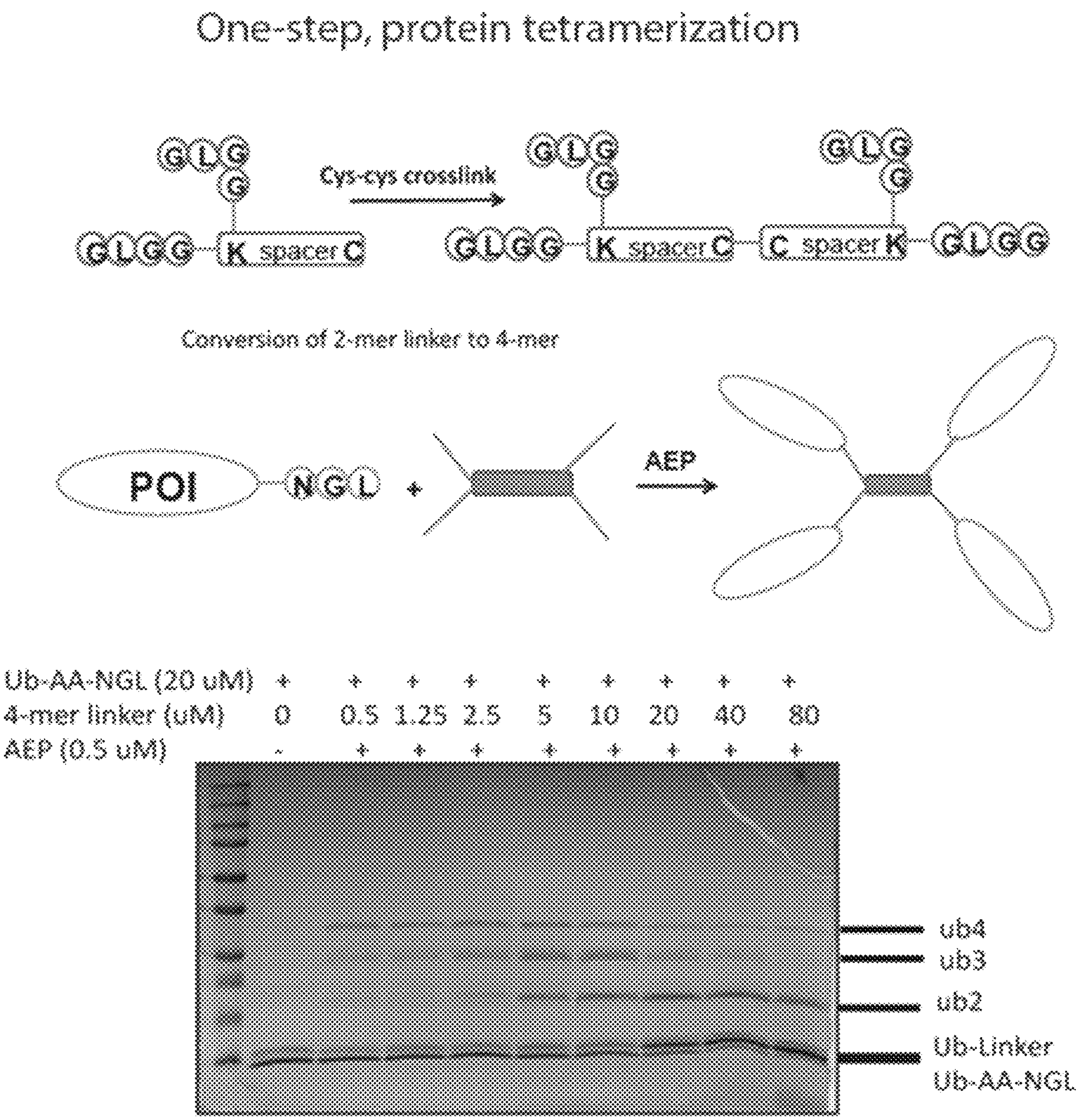
FIG. 14C shows schemes for scaffold-based one-step tetramerization.
Figure 14D:
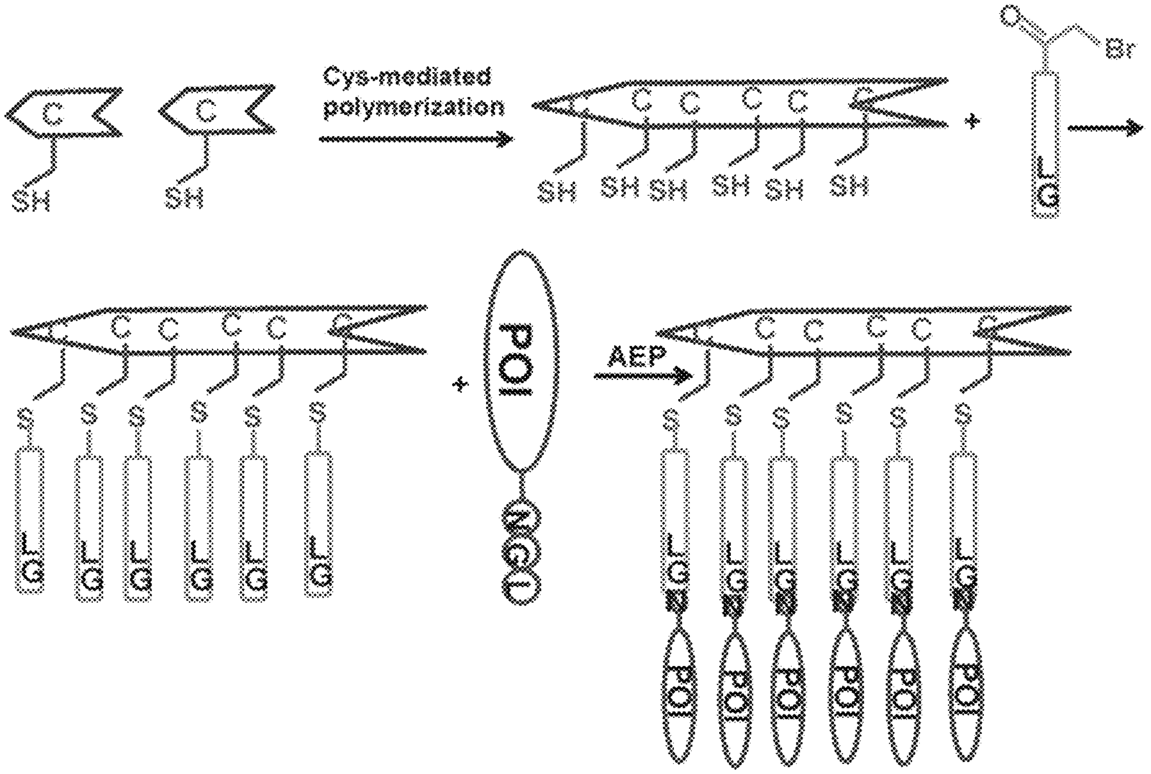
FIG. 14D shows schemes for modular ultra-oligomerization. Additionally shown are schemes for preparing (FIG. 14E, FIG. 14F) NGL head-to-head dimers, (FIG. 14G) GL linker dimers and tetramers, (FIG. 14H) NGL multimers, and (FIG. 14I) GL multimers.
Figure 14E:
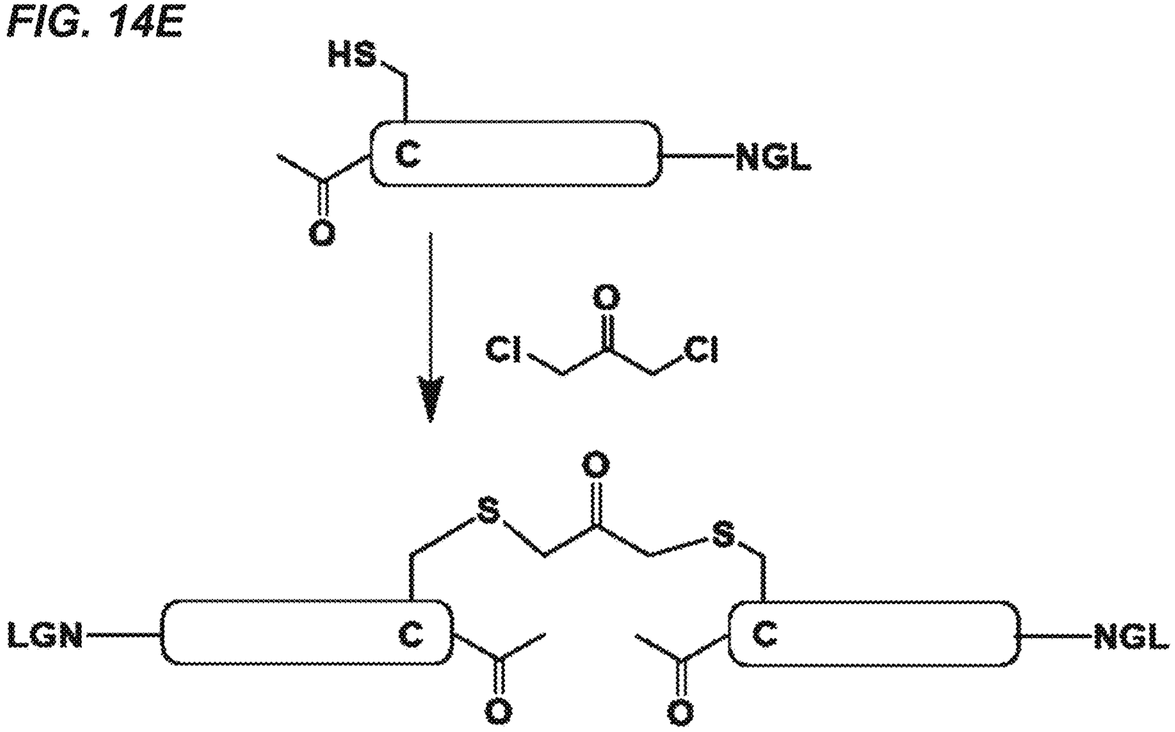
FIG. 14A shows schemes for scaffold-based one-step homodimerization.
Figure 14F:
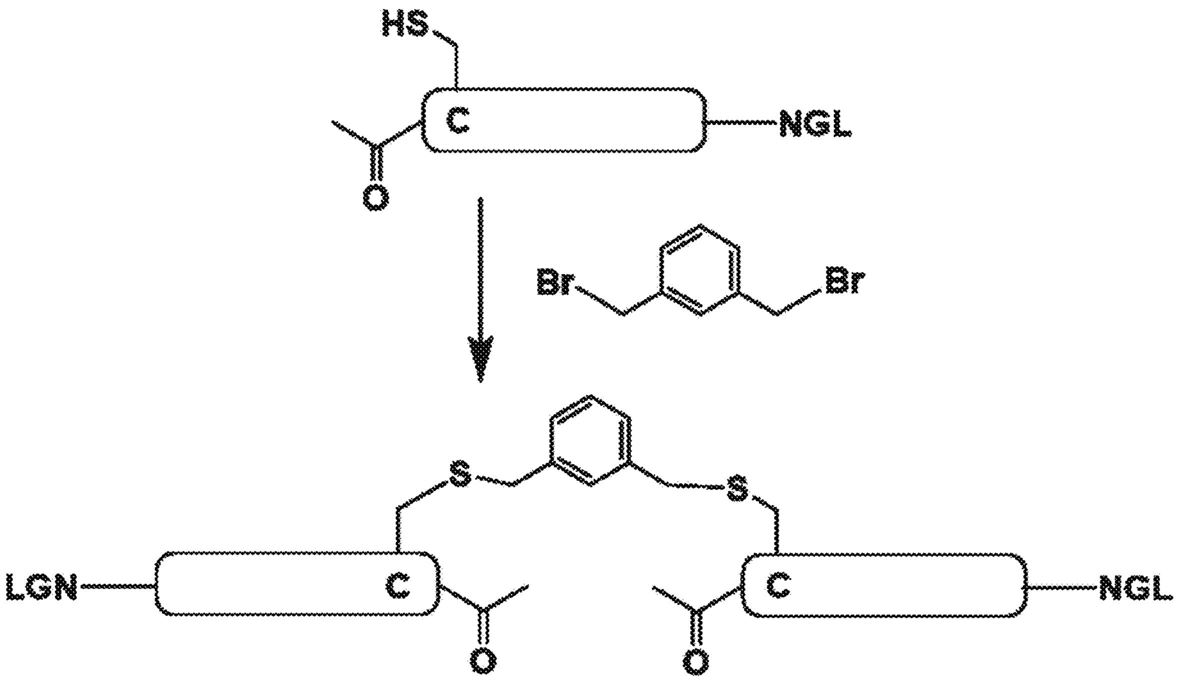
Figure 14G:
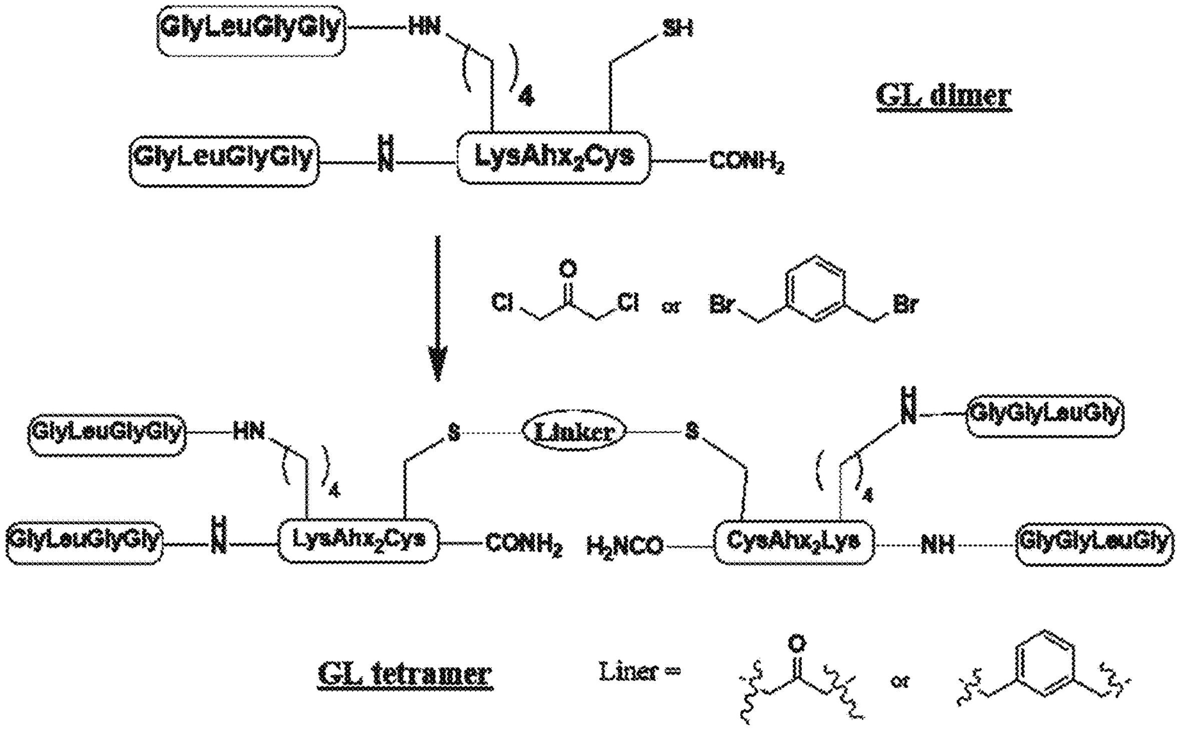
Figure 14H:
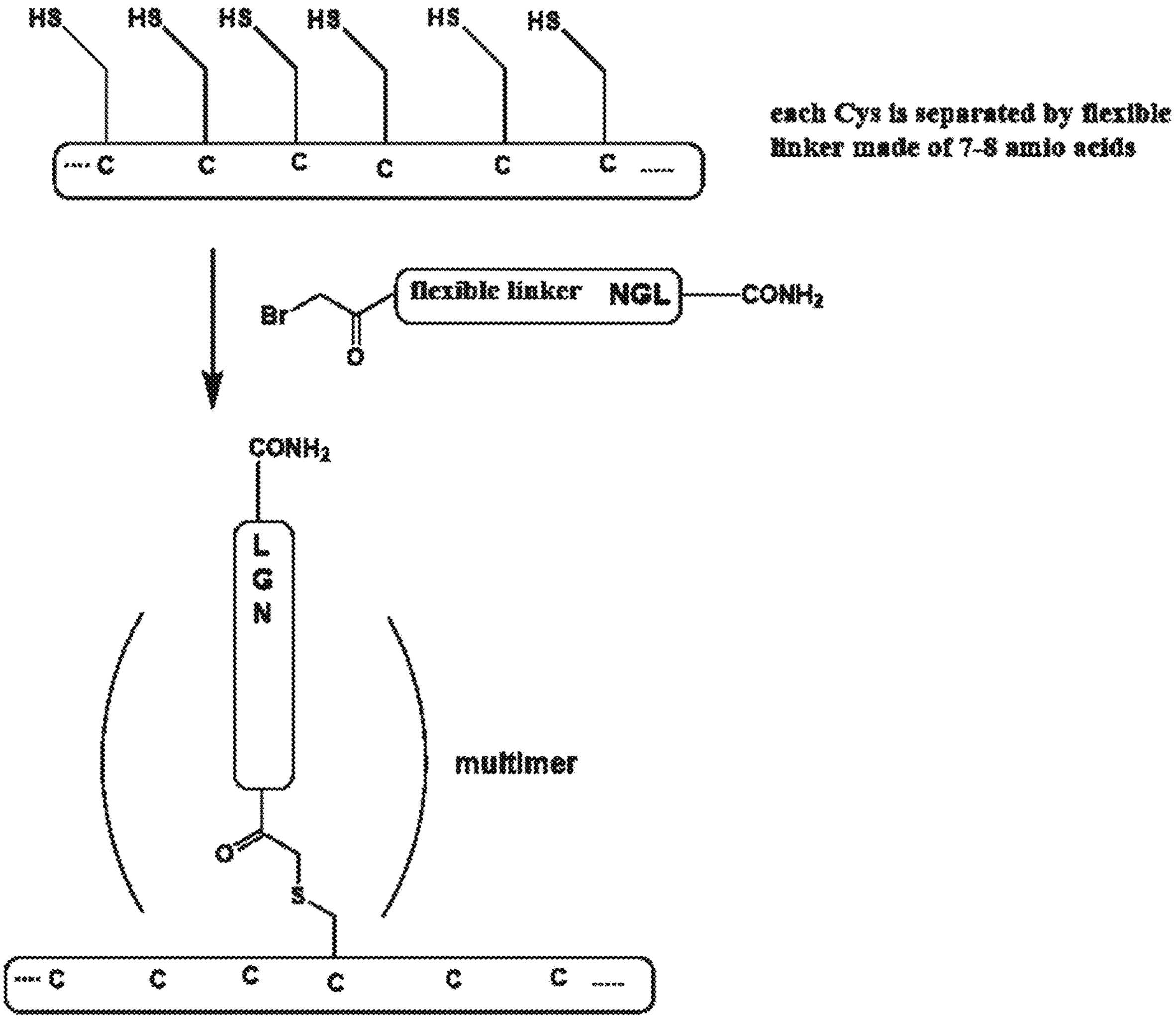
Figure 14I:
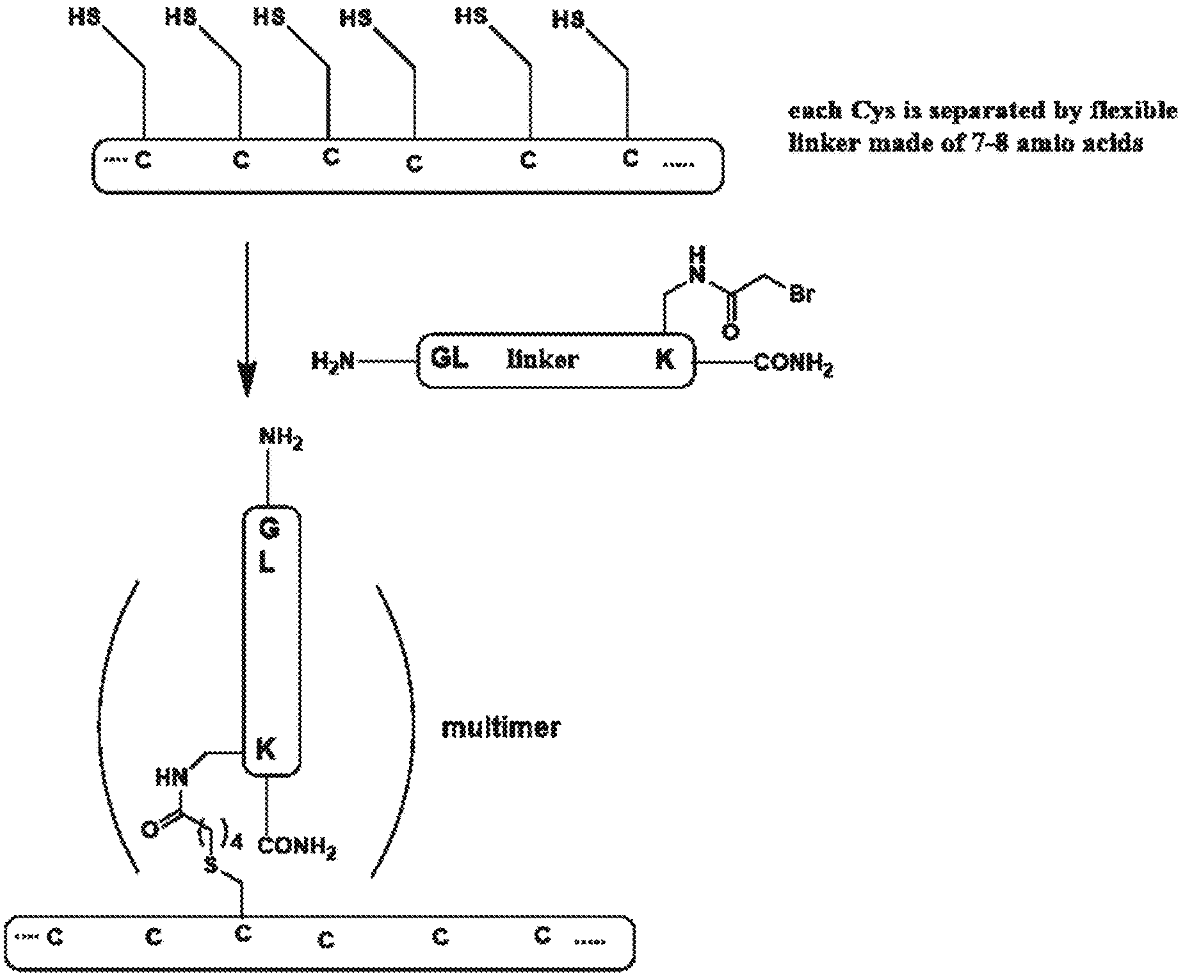

Based on the prediction of the sequence alignment, AEP_C13CO4 contained the conserved structural motif identical to Quicklase (247-264). This indicated that AEP_C13CO4 might be functional protein ligase. The cDNA of AEP_C13CO4 was then subsequently synthesized and subcloned into pet28b in a similar way as Quicklase. This new potential ligase was then expressed, purified and activated in the same way as Quicklase, and exhibited both proteolytic and protein ligation activities. Although the wild type of AEP_C13CO4 is not an ideal protein ligase, with much slower enzymatic catalytic efficiency as Quicklase, and having significant byproducts of proteolytic reactions (FIG. 13), it appears to a good starting point for further engineering of an alternative protein ligase.

Example 4: QuicklaseOaAEP1-Catalyzed Peptide Dimerization, Oligomerization, and Multimerization In relation to the schemes illustrated in FIGS. 14A-14I, the following exemplary experiments were carried out:

FIG. 14A:

The branched 2-mer linker peptide was synthesized based on standard Fmoc-Solid Phase Peptide Synthesis (SPPS) chemistry on Rink Amide MBHA resin (GL Biochem, Shanghai, China). The branch was introduced by incorporation of Fmoc-L-Lys(Fmoc)-OH. After removing of Fmoc groups at both α- and ε-amino groups, the remaining amino acids (GLGG) were introduced according to the standard Fmoc-SPPS procedure.

For one-step homodimerization reaction, 50 μM of C-terminal NGL-tagged Protein of Interest (POI-NGL), Ub-AA-NGL in this case, was reacted with various concentrations of 2-mer linker ranging from 0-200 μM catalyzed by 0.5 μM of AEP at room temperature. The reaction was monitored by SDS-PAGE after 1 h.

FIG. 14B:

For two-step heterodimerization strategy, the first step was the enzyme (0.5 μM) catalyzed reaction between POIA-NGL (50 μM) with excessive amount of 2-mer linker (200 μM) to enable only one branch of the dimer linker was labelled. After reaction, the POIA-linker was isolated by removing 2-mer linker peptide through buffer exchange with 3500 MW cut off concentrator.

For the second ligation step, POIB-NGL (100, 200 μM) was reacted with POIA-linker (50 μM) catalyzed by 0.5 μM of AEP to get the final heterodimer product.

FIG. 14C:

To generate the 4-mer linker, the 2-mer linker was dimerized through crosslinking of the C-terminal cysteine residue. See figure g for the reaction detail.

One-step protein tetramerization was achieved by AEP catalyzed reaction between POI-NGL and the 4-mer linker. With ubiquitin as an example, to optimize the ligation reaction, 20 μM of Ub-AA-NGL (POI-NGL) was ligated with various concentrations (0-80 μM) of 4-mer linker in the presence of 0.5 μM of AEP at pH 7.4, room temperature. After 1 h, the reaction was analyzed by SDS-PAGE, which indicated that maximal amount of Ub-tetramer was yielded when 2.5-5 μM of 4-mer linker was used.

FIG. 14D:

To achieve protein ultra-oligomerization, the oligomer peptide platform was first synthesized via two steps: i) a peptide containing multiple cysteine residues which were separated by flexible spacer of 7-8 amino acids was synthesized directly or through native chemical ligation; ii) the cysteine residues in the peptide was then alkylated by a bromoacetyl peptide with a free N-terminal GL residues for AEP catalyzed ligation later. After producing the oligomer linker, AEP catalyzed reaction between POI-NGL and the oligomer linker was performed to generated the protein ultra-oligomer.

FIGS. 14E, 14F:

Schemes for the generation of 2-mer-NGL linker used for protein head-to-head dimerization:

The synthesis of 2-mer-NGL liner was achieved via S-alkylation of the N-terminal acetylated cysteine residue of the monomer-NGL peptide by either 1,3-dichloroacetone or m-Xylylene dibromide (Sigma-aldrich). Briefly, monomer-NGL peptide was dissolved in a buffer containing 20 mM TrisHCl, 150 mM NaCl, 5 mM TCEP, pH 8.0 at a final concentration of 1 mg/mL. 1 eq. of 1,3-dichloroacetone or m-Xylylene dibromide was added into the solution. After 3 h reaction under dark condition, the desired 2-mer-NGL linker was isolated by HPLC purification with C18-reverse phase column.

FIG. 14G:

Schemes for the generation of GL-tetramer linker used for protein tail-to-tail tetramerization:

The synthesis of GL-tetramer linker was achieved via S-alkylation of the C-terminal cysteine residue of the GL-dimer linker peptide by either 1,3-dichloroacetone or m-Xylylene dibromide. Briefly, GL-dimer peptide was dissolved in a buffer containing 20 mM TrisHCl, 150 mM NaCl, 5 mM TCEP, pH 8.0 at a final concentration of 1 mg/mL. 1 eq. of 1,3-dichloroacetone or m-Xylylene dibromide was added into the solution. After 3 h reaction under dark condition, the desired GL-tetramer linker was isolated by HPLC purification with C18-reverse phase column.

FIG. 14H:

Scheme for the generation of NGL-oligomer linker used for protein head-to-head oligomerization: NGL-oligomer linker platform was synthesized via the S-alkylation reaction between a peptide containing multiple cysteine residues which were separated by flexible spacer of 7-8 amino acids and another N-terminal bromoacetyl peptide with C-terminal NGL residues for AEP catalyzed ligation later. For the alkylation reaction, briefly, 1 mg/mL of cysteinyl peptide was reacted with 1.5 mg/mL of bromoacetyl peptide in buffer containing 20 mM TrisHCl, 150 mM NaCl, 5 mM TCEP, pH 8.0, at room temperature avoid of light. After 2 hours, the desired NGL-oligomer linker was isolated by HPLC purification with C18-reverse phase column.

FIG. 14I:

Scheme for the generation of GL-oligomer linker used for protein tail-to-tail oligomerization:

GL-oligomer linker platform was synthesized via the S-alkylation reaction between a peptide containing multiple cysteine residues which were separated by flexible spacer of 7-8 amino acids and another bromoacetyl peptide (bromoacetyl attached to lysine side chain) with N-terminal GL residues for AEP catalyzed ligation later. For the alkylation reaction, briefly, 1 mg/mL of cysteinyl peptide was reacted with 1.5 mg/mL of bromoacetyl peptide in buffer containing 20 mM TrisHCl, 150 mM NaCl, 5 mM TCEP, pH 8.0, at room temperature avoid of light. After 2 hours, the desired GL-oligomer linker was isolated by HPLC purification with C18-reverse phase column.

Example 5: QuicklaseOaAEP1-Catalyzed Cell Surface Labeling

Figure 15B:
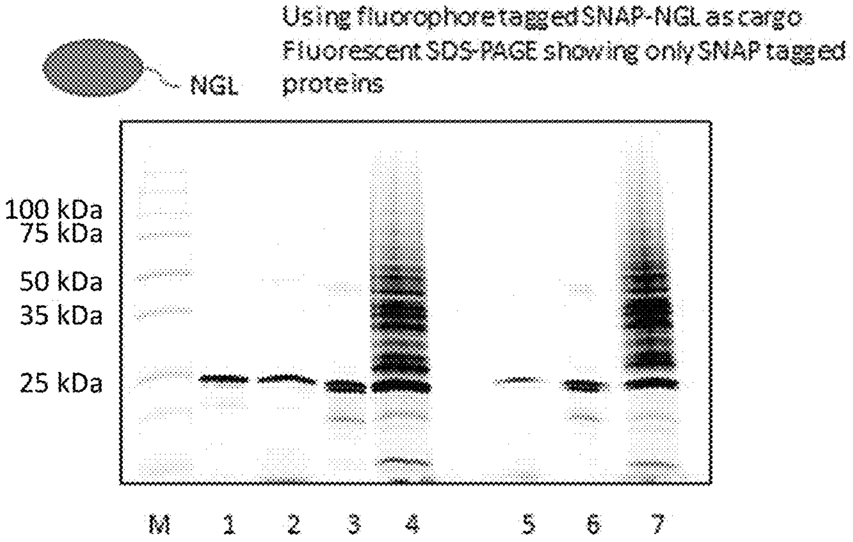
FIG. 15B shows fluorecently tagged SNAP (New England Biolabs) protein was conjugated to the intrinsic cellular surface proteins of two different cell lines, RAW cell (human macrophage cell line) and HEK293T (human epithelial cell line). 10 μM modified SNAP protein (with additional C-terminal NGL residues, lane 1 sample) with or without (lane 2 and lane 5 samples) coincubation of 0.1 μM Quicklase were added to cell culture, pre-washed with PBS buffer. After 30 minutes~1 hour incubation, cells were rinsed with additional PBS buffer (lane 3 and lane 6 were first wash samples), two times. The remaining cell was harvested and lysed with SDS loading buffer (lane 4 and 7 samples). All samples were examined using SDS-PAGE, and only the covalently fluorescently tagged SNAP protein carried the signal on the gel, which were shown as dark bands in (b). Additional bands in lane 4 and 7 indicated that significant amount of intrinsic proteins in RAW and HEK283T cells were conjugated with SNAP protein, in a Quicklase dependant way.
Figure 15C:
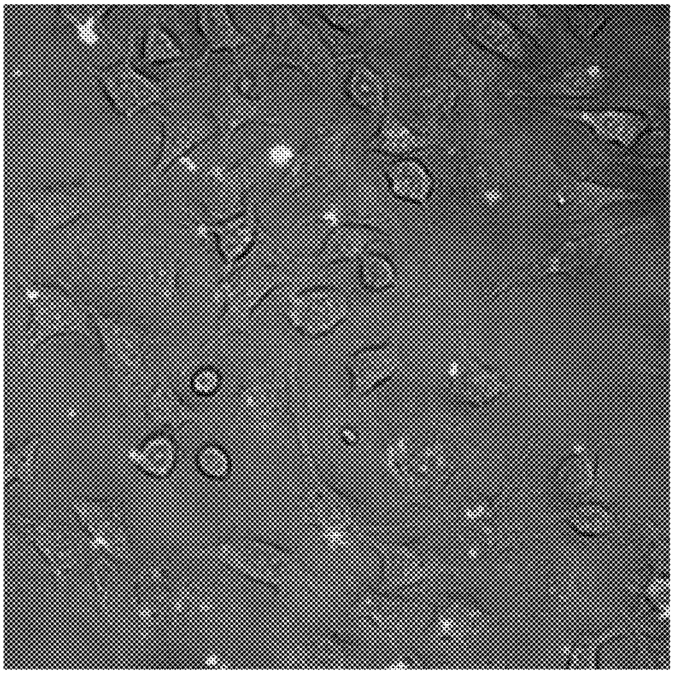
FIG. 15C shows surface modified RAW cells were examined using a fluorescent microscope, bright spots on the cellular surface indicated successful surface labelling of intrinsic cellular membrane. Certain intrinsic proteins with amino acids residue sequences closely related to formula III could be recognized as Quicklase, due to its superior enzymatic activity and broader sequence recognition ability.

In relation to FIGS. 15A and 15B, the following exemplary experiments were carried out:

0.1 to 1 μM of OaAEP1 Cys247Ala was added to cellular culture in standard cell culture conditions. 1-20 μM labeling protein tags were added to the reaction afterwards, and incubated for 30-45 mins at 37° C. and standard culturing condition, before both excess enzymes and labelling tags were washed away. Triple washed cellular fractions were harvested to perform the fluorescent SDS-PAGE analysis to determine the labelling efficiency.

In the case of imaging analysis, the images were acquired using Nikon Ti microscope or equivalent (Nikon) with the laser source X-Cite 120 (Excelitas), or equivalent, and digital camera C11440 (Hamamatsu), or equivalent. The programme with which cells were viewed and photographed was MetaMorph (Molecular Devices) or equivalent. Images were compiled using Image J, or equivalent.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other embodiments are within the following claims. In addition, where features or aspects of the invention are described in terms of Markush groups, those skilled in the art will recognize that the invention is also thereby described in terms of any individual member or subgroup of members of the Markush group.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," containing", etc., shall be read expansively and without limitation. The word "comprise" or variations such as "comprises" or "comprising" will accordingly be understood to imply the inclusion of a stated integer or groups of integers but not the exclusion of any other integer or group of integers. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The content of all documents and patent documents cited herein is incorporated by reference in their entirety.

What is claimed is:

1. A peptide ligase having peptide ligase activity and comprising or consisting of:

(a) an amino acid sequence that shares at least 80% sequence identity with the amino acid sequence as set forth in SEQ ID NO: 1, provided that said peptide ligase comprises the amino acid sequence set forth in SEQ ID NO: 2 at the positions corresponding to residues 247-264 of SEQ ID NO: 1, and the amino acid at position 247 is alanine; or (b) a fragment of the amino acid sequence of (a) provided that said fragment comprises the amino acid sequence set forth in SEQ ID NO: 2 at the positions corresponding to residues 247-264 of SEQ ID NO: 1, and the amino acid at position 247 is alanine, and wherein the fragment is at least 150 amino acids in length; or (c) an amino acid sequence comprising the fragment of (b), wherein said peptide ligase is not the wild-type OaAEP1 having the amino acid sequence set forth in SEQ ID NO: 3 or butelase 1 having the amino acid sequence set forth in SEQ ID NO: 4.

2. The peptide ligase of claim 1, wherein the peptide ligase comprises or consists of an amino acid sequence that shares at least 90% sequence identity with the amino acid sequence as set forth in SEQ ID NO: 1, provided that said peptide ligase comprises the amino acid sequence set forth in SEQ ID NO: 2 at the positions corresponding to residues 247-264 of SEQ ID NO: 1, and the amino acid at position 247 is alanine.

3. The peptide ligase of claim 1, wherein the peptide ligase comprises or consists of an amino acid sequence that shares at least 95% sequence identity with the amino acid sequence as set forth in SEQ ID NO: 1, provided that said peptide ligase comprises the amino acid sequence set forth in SEQ ID NO: 2 at the positions corresponding to residues 247-264 of SEQ ID NO: 1, and the amino acid at position 247 is alanine.

4. The peptide ligase of claim 1, wherein the peptide ligase comprises or consists of the amino acid sequence set forth in SEQ ID NO: 1.

5. The peptide ligase of claim 1, wherein the fragment of the amino acid sequence of (a) is at least 200 amino acids in length.

6. The peptide ligase of claim 1, wherein the fragment of the amino acid sequence of (a) is at least 250 amino acids in length.

7. The peptide ligase of claim 1, wherein the peptide ligase has at least 50% of the peptide ligase activity of the peptide ligase having the amino acid sequence of SEQ ID NO: 1.

8. The peptide ligase of claim 1, wherein the peptide ligase has at least 70% of the peptide ligase activity of the peptide ligase having the amino acid sequence of SEQ ID NO: 1.

9. The peptide ligase of claim 1, wherein the peptide ligase has at least 90% of the peptide ligase activity of the peptide ligase having the amino acid sequence of SEQ ID NO: 1.

* * * * *